US010500304B2

(12) United States Patent
Armbruster et al.

(10) Patent No.: US 10,500,304 B2
(45) Date of Patent: Dec. 10, 2019

(54) FILMS AND METHODS OF MANUFACTURE

(71) Applicant: DePuy Synthes Products, Inc., Raynham, MA (US)

(72) Inventors: David A. Armbruster, West Chester, PA (US); James Dwyer, West Chester, PA (US); Jeffrey Chomyn, Maurrieta, CA (US); Sean H. Kerr, Oreland, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/725,586

(22) Filed: Oct. 5, 2017

(65) Prior Publication Data

US 2018/0028714 A1 Feb. 1, 2018

Related U.S. Application Data

(62) Division of application No. 14/899,570, filed as application No. PCT/US2014/041662 on Jun. 10, 2014, now abandoned.

(60) Provisional application No. 61/837,716, filed on Jun. 21, 2013.

(51) Int. Cl.
| | |
|---|---|
| *A61L 24/00* | (2006.01) |
| *A61L 31/06* | (2006.01) |
| *A61L 31/14* | (2006.01) |
| *A61L 31/16* | (2006.01) |
| *A61F 2/30* | (2006.01) |
| *B32B 3/26* | (2006.01) |
| *A61B 17/80* | (2006.01) |
| *A61K 9/70* | (2006.01) |
| *A61B 17/00* | (2006.01) |

(52) U.S. Cl.
CPC .......... *A61L 24/0015* (2013.01); *A61B 17/80* (2013.01); *A61B 17/8057* (2013.01); *A61B 17/8085* (2013.01); *A61F 2/30907* (2013.01); *A61K 9/7007* (2013.01); *A61L 31/06* (2013.01); *A61L 31/14* (2013.01); *A61L 31/16* (2013.01); *B32B 3/266* (2013.01); *A61B 2017/00526* (2013.01); *A61F 2002/30677* (2013.01); *A61F 2310/0097* (2013.01); *A61F 2310/00389* (2013.01); *A61L 2430/02* (2013.01); *B32B 2535/00* (2013.01)

(58) Field of Classification Search
CPC .. A61K 9/7007; A61K 9/0024; A61K 31/192; A61K 31/4045; A61K 31/405; A61K 31/5575; A61K 47/42; A61K 47/46; A61K 9/0051; A61K 9/0056; A61K 9/06; A61K 9/2027; A61L 15/24; A61L 31/10; A61L 15/44; A61L 2300/00; A61L 2300/416; A61L 2300/42; A61L 2300/606; A61L 2300/63; A61L 31/16
See application file for complete search history.

(56) References Cited

U.S. PATENT DOCUMENTS

| | | | |
|---|---|---|---|
| 3,155,095 | A | 11/1964 | Brown |
| 3,719,736 | A | 3/1973 | Woodruff |
| 3,949,037 | A | 4/1976 | Volent |
| 4,148,871 | A | 4/1979 | Pitt et al. |
| 4,297,993 | A | 11/1981 | Harle |
| 4,587,268 | A | 5/1986 | Pfirrmann |
| 4,605,414 | A | 8/1986 | Czajka |
| 4,605,730 | A | 8/1986 | Shalaby et al. |
| 4,659,700 | A | 4/1987 | Jackson |
| 4,730,726 | A | 3/1988 | Holzwarth |
| 4,774,091 | A | 9/1988 | Yamahira et al. |
| 4,863,444 | A | 9/1989 | Blomer |
| 4,888,023 | A | 12/1989 | Averill et al. |
| 5,021,241 | A | 6/1991 | Yamahira et al. |
| 5,084,050 | A | 1/1992 | Draenert |
| 5,093,319 | A | 3/1992 | Higham et al. |

(Continued)

FOREIGN PATENT DOCUMENTS

| | | |
|---|---|---|
| AU | 2004202878 A1 | 7/2004 |
| CN | 1206353 A | 1/1999 |

(Continued)

OTHER PUBLICATIONS

Zhang et al., Biodegradable Controlled Antibiotic Release Devices for Osteomyelitis: Optimization of Release Properties, Journal of Pharmacy and Pharmacology, Sep. 1994, vol. 46, Issue 9.
Written Opinion of the International Searching Authority for Application No. PCT/US2006/40038, dated Sep. 25, 2007, 6 pages.
Von Plocki et al., "Biodegradable Sleeves for Metal Implants to Prevent Implant-Associated Infection: An Experimental In Vivo Study in Sheep", Vet Surg., Apr. 2012, 41(3), 410-421, Epub Jan. 12, 2012.
U.S. Application Filed on Oct. 13, 2005 by Kerr et al., U.S. Appl. No. 60/726,808.
Trampuz et al., "Diagnosis and Treatment of Infections Associated with Fracture-Fixation Devices", Injury, May 2006, 37, Suppl 2, S59-S66.

(Continued)

*Primary Examiner* — Audrea B Coniglio
(74) *Attorney, Agent, or Firm* — BakerHostetler

(57) ABSTRACT

Embodiments of the present disclosure are directed to perforated polymer films and methods of making the same. In some embodiments, the films are for use with implantable medical devices. In one embodiment there is a flexible body including a polymer film having a first surface and an opposing second surface, the film having a plurality of apertures extending from the first surface to the second surface and a plurality of raised lips protruding from the first surface such that each of the plurality of apertures is surrounded by a one of the plurality of raised lips. In one embodiment, the film comprises a single layer, and in another embodiment, the film can comprise a plurality of layers. In certain embodiments, the film can comprise an adhesive layer. In another embodiment, one or more of the layers may be a drug containing layer and/or a rate controlling layer for drug release.

15 Claims, 43 Drawing Sheets

(56) References Cited

U.S. PATENT DOCUMENTS

| | | |
|---|---|---|
| 5,100,668 A | 3/1992 | Edelman et al. |
| 5,104,266 A | 4/1992 | Daryoush et al. |
| 5,147,400 A | 9/1992 | Kaplan et al. |
| 5,260,066 A | 11/1993 | Wood et al. |
| 5,268,178 A | 12/1993 | Calhoun et al. |
| 5,281,221 A | 1/1994 | Tadych |
| 5,324,519 A * | 6/1994 | Dunn .................. A61K 9/0024 424/426 |
| 5,326,356 A | 7/1994 | Della Valle et al. |
| 5,383,928 A | 1/1995 | Ledergerber |
| 5,456,721 A | 10/1995 | Legrand |
| 5,458,653 A | 10/1995 | Shearer et al. |
| 5,462,563 A | 10/1995 | Shearer et al. |
| 5,468,253 A | 11/1995 | Bezwada et al. |
| 5,489,305 A | 2/1996 | Morgan |
| 5,507,814 A | 4/1996 | Gilbert et al. |
| 5,521,193 A | 5/1996 | Flynn et al. |
| 5,549,676 A | 8/1996 | Johnson |
| 5,567,431 A | 10/1996 | Vert et al. |
| 5,571,204 A | 11/1996 | Nies |
| 5,637,113 A | 6/1997 | Tartaglia et al. |
| 5,656,605 A | 8/1997 | Hansson et al. |
| 5,679,299 A | 10/1997 | Gilbert et al. |
| 5,693,085 A | 12/1997 | Buirge et al. |
| 5,713,904 A | 2/1998 | Errico et al. |
| 5,716,981 A | 2/1998 | Hunter et al. |
| 5,725,570 A | 3/1998 | Heath |
| 5,755,720 A | 5/1998 | Mikhail |
| 5,795,584 A | 8/1998 | Totakura et al. |
| 5,798,113 A | 8/1998 | Dionne et al. |
| 5,800,519 A | 9/1998 | Sandock |
| 5,800,544 A | 9/1998 | Demopulos et al. |
| 5,800,828 A | 9/1998 | Dionne et al. |
| 5,800,829 A | 9/1998 | Dionne et al. |
| 5,824,088 A | 10/1998 | Kirsch |
| 5,834,001 A | 11/1998 | Dionne et al. |
| 5,855,906 A | 1/1999 | McClay |
| 5,869,077 A | 2/1999 | Dionne et al. |
| 5,871,767 A | 2/1999 | Dionne et al. |
| 5,873,906 A | 2/1999 | Lau et al. |
| 5,874,099 A | 2/1999 | Dionne et al. |
| 5,876,432 A | 3/1999 | Lau et al. |
| 5,919,225 A | 7/1999 | Lau et al. |
| 5,919,235 A | 7/1999 | Husson et al. |
| 5,947,893 A | 9/1999 | Agrawal et al. |
| 5,955,095 A | 9/1999 | Gentile et al. |
| 5,984,926 A | 11/1999 | Jones |
| 6,001,123 A | 12/1999 | Lau |
| 6,013,104 A | 1/2000 | Kampner |
| 6,015,429 A | 1/2000 | Lau et al. |
| 6,017,362 A | 1/2000 | Lau |
| 6,063,395 A | 5/2000 | Markkula et al. |
| 6,071,567 A | 6/2000 | Castelli et al. |
| 6,083,523 A | 7/2000 | Dionne et al. |
| 6,117,442 A | 9/2000 | Markkula et al. |
| 6,143,029 A | 11/2000 | Rippstein |
| 6,143,033 A | 11/2000 | Paul et al. |
| 6,165,202 A | 12/2000 | Kokish et al. |
| 6,165,210 A | 12/2000 | Lau et al. |
| 6,180,052 B1 | 1/2001 | Ouellette et al. |
| 6,193,746 B1 | 2/2001 | Strecker |
| 6,221,097 B1 | 4/2001 | Wang et al. |
| 6,232,869 B1 | 5/2001 | Choi |
| 6,235,869 B1 | 5/2001 | Roby et al. |
| 6,248,112 B1 | 6/2001 | Gambale et al. |
| 6,254,627 B1 | 7/2001 | Freidberg |
| 6,258,125 B1 | 7/2001 | Paul et al. |
| 6,277,084 B1 | 8/2001 | Abele et al. |
| 6,280,411 B1 | 8/2001 | Lennox |
| 6,287,291 B1 | 9/2001 | Bigus et al. |
| 6,287,331 B1 | 9/2001 | Heath |
| 6,287,628 B1 | 9/2001 | Hossainy et al. |
| 6,287,638 B1 | 9/2001 | Castelli et al. |
| 6,290,721 B1 | 9/2001 | Heath |
| 6,299,894 B1 | 10/2001 | Markkula et al. |
| 6,306,166 B1 | 10/2001 | Barry et al. |
| 6,322,804 B1 | 11/2001 | Dionne et al. |
| 6,331,186 B1 | 12/2001 | Wang et al. |
| 6,331,188 B1 | 12/2001 | Lau et al. |
| 6,337,088 B1 | 1/2002 | Gentile et al. |
| 6,350,284 B1 | 2/2002 | Tormala et al. |
| 6,379,381 B1 | 4/2002 | Hossainy et al. |
| 6,383,190 B1 | 5/2002 | Preissman |
| 6,419,694 B1 | 7/2002 | Sandock |
| 6,432,141 B1 | 8/2002 | Stocks et al. |
| 6,443,980 B1 | 9/2002 | Wang et al. |
| 6,447,522 B2 | 9/2002 | Gambale et al. |
| 6,451,003 B1 | 9/2002 | Prosl et al. |
| 6,451,050 B1 | 9/2002 | Rudakov et al. |
| 6,468,300 B1 | 10/2002 | Freidberg |
| 6,476,079 B1 | 11/2002 | Jukarainen et al. |
| 6,482,235 B1 | 11/2002 | Lambrecht et al. |
| 6,491,720 B1 | 12/2002 | Vallana et al. |
| 6,494,898 B1 | 12/2002 | Roby et al. |
| 6,497,709 B1 | 12/2002 | Heath |
| 6,503,556 B2 | 1/2003 | Harish et al. |
| 6,503,954 B1 | 1/2003 | Bhat et al. |
| 6,517,570 B1 | 2/2003 | Lau et al. |
| 6,520,984 B1 | 2/2003 | Garrison et al. |
| 6,545,097 B2 | 4/2003 | Pinchuk et al. |
| 6,547,812 B1 | 4/2003 | Hu |
| 6,554,863 B2 | 4/2003 | Paul et al. |
| 6,569,180 B1 | 5/2003 | Sirhan et al. |
| 6,592,569 B2 | 7/2003 | Bigus et al. |
| 6,592,885 B2 | 7/2003 | Phaneuf et al. |
| 6,596,296 B1 | 7/2003 | Nelson et al. |
| 6,602,290 B2 | 8/2003 | Esnouf et al. |
| 6,607,544 B1 | 8/2003 | Boucher et al. |
| 6,613,072 B2 | 9/2003 | Lau et al. |
| 6,632,235 B2 | 10/2003 | Weikel et al. |
| 6,641,587 B2 | 11/2003 | Scribner et al. |
| 6,645,241 B1 | 11/2003 | Strecker |
| 6,660,038 B2 | 12/2003 | Boyer, II et al. |
| 6,666,880 B1 | 12/2003 | Chiu et al. |
| 6,692,498 B1 | 2/2004 | Niiranen et al. |
| 6,706,058 B2 | 3/2004 | Hierlemann et al. |
| 6,713,119 B2 | 3/2004 | Hossainy et al. |
| 6,716,216 B1 | 4/2004 | Boucher et al. |
| 6,716,444 B1 | 4/2004 | Castro et al. |
| 6,719,773 B1 | 4/2004 | Boucher et al. |
| 6,726,691 B2 | 4/2004 | Osorio et al. |
| 6,746,483 B1 | 6/2004 | Bojarski et al. |
| 6,749,626 B1 | 6/2004 | Bhat et al. |
| 6,759,054 B2 | 7/2004 | Chen et al. |
| 6,767,369 B2 | 7/2004 | Boyer, II et al. |
| 6,790,224 B2 | 9/2004 | Gerberding |
| 6,790,228 B2 | 9/2004 | Hossainy et al. |
| RE38,614 E | 10/2004 | Paul et al. |
| 6,818,247 B1 | 11/2004 | Chen et al. |
| 6,827,743 B2 | 12/2004 | Eisermann et al. |
| 6,840,770 B2 | 1/2005 | Nusskern et al. |
| 6,855,770 B2 | 2/2005 | Pinchuk et al. |
| 6,863,530 B2 | 3/2005 | McDevitt |
| 6,863,692 B2 | 3/2005 | Meulink |
| 6,883,520 B2 | 4/2005 | Lambrecht et al. |
| 6,884,427 B1 | 4/2005 | Barrows |
| 6,899,719 B2 | 5/2005 | Reiley et al. |
| 6,908,624 B2 | 6/2005 | Hossainy et al. |
| 6,946,143 B2 | 9/2005 | Kim et al. |
| 6,953,560 B1 | 10/2005 | Castro et al. |
| 6,960,351 B2 | 11/2005 | Dionne et al. |
| 6,979,341 B2 | 12/2005 | Scribner et al. |
| 6,981,991 B2 | 1/2006 | Ferree |
| 6,986,788 B2 | 1/2006 | Paul et al. |
| 7,001,390 B2 | 2/2006 | Gebhardt et al. |
| 7,014,659 B2 | 3/2006 | Boyer, II et al. |
| 7,025,791 B2 | 4/2006 | Levine et al. |
| 7,037,332 B2 | 5/2006 | Kutryk et al. |
| 7,041,308 B2 | 5/2006 | Shalaby et al. |
| 7,056,577 B1 | 6/2006 | Bruce et al. |
| 7,070,613 B2 | 7/2006 | Weber et al. |
| 7,087,082 B2 | 8/2006 | Paul et al. |
| 7,087,087 B2 | 8/2006 | Boyer et al. |
| 7,101,392 B2 | 9/2006 | Heath |

(56) References Cited

U.S. PATENT DOCUMENTS

| | | |
|---|---|---|
| 7,108,717 B2 | 9/2006 | Freidberg |
| 7,115,146 B2 | 10/2006 | Boyer et al. |
| 7,122,058 B2 | 10/2006 | Levine et al. |
| 7,131,986 B2 | 11/2006 | Sirhan et al. |
| 7,137,993 B2 | 11/2006 | Acosta et al. |
| 7,147,656 B2 | 12/2006 | Andreas et al. |
| 7,153,306 B2 | 12/2006 | Ralph et al. |
| 7,153,307 B2 | 12/2006 | Scribner et al. |
| 7,168,605 B2 | 1/2007 | Walak |
| 7,169,405 B2 | 1/2007 | Trieu |
| 7,175,873 B1 | 2/2007 | Roorda et al. |
| 7,182,779 B2 | 2/2007 | Acosta et al. |
| 7,192,448 B2 | 3/2007 | Ferree |
| 7,198,047 B2 | 4/2007 | Lambrecht et al. |
| 7,208,008 B2 | 4/2007 | Clarke |
| 7,238,168 B2 | 7/2007 | Sirhan et al. |
| 7,247,313 B2 | 7/2007 | Roorda et al. |
| 7,252,671 B2 | 8/2007 | Scribner et al. |
| 7,261,720 B2 | 8/2007 | Stevens et al. |
| 7,267,694 B2 | 9/2007 | Levine et al. |
| 7,270,668 B2 | 9/2007 | Andreas et al. |
| 7,279,008 B2 | 10/2007 | Brown et al. |
| 7,279,175 B2 | 10/2007 | Chen et al. |
| 7,294,146 B2 | 11/2007 | Chew et al. |
| 7,296,998 B2 | 11/2007 | Bartee et al. |
| 7,300,456 B2 | 11/2007 | Andreas et al. |
| 7,300,465 B2 | 11/2007 | Paul et al. |
| 7,309,350 B2 | 12/2007 | Landreville et al. |
| 7,311,727 B2 | 12/2007 | Mazumder et al. |
| 7,329,285 B2 | 2/2008 | Levine et al. |
| 7,347,873 B2 | 3/2008 | Paul et al. |
| 7,347,875 B2 | 3/2008 | Levine et al. |
| 7,351,255 B2 | 4/2008 | Andreas |
| 7,357,812 B2 | 4/2008 | Andreas et al. |
| 7,402,172 B2 | 7/2008 | Chin et al. |
| 7,407,512 B2 | 8/2008 | Bojarski et al. |
| 7,458,990 B2 | 12/2008 | Chieng |
| 7,465,318 B2 | 12/2008 | Sennett et al. |
| 7,473,277 B2 | 1/2009 | Boyer, II et al. |
| 7,491,234 B2 | 2/2009 | Palasis et al. |
| 7,503,936 B2 | 3/2009 | Trieu |
| 7,504,125 B1 | 3/2009 | Pacetti et al. |
| 7,550,012 B2 | 6/2009 | Lavelle |
| 7,553,539 B2 | 6/2009 | Bruce et al. |
| 7,578,834 B2 | 8/2009 | Abdou |
| 7,608,114 B2 | 10/2009 | Levine et al. |
| 7,611,481 B2 | 11/2009 | Cleary et al. |
| 7,618,432 B2 | 11/2009 | Pedersen et al. |
| 7,618,448 B2 | 11/2009 | Schmitz et al. |
| 7,618,647 B2 | 11/2009 | Weber et al. |
| 7,622,146 B2 | 11/2009 | Roorda et al. |
| 7,622,530 B2 | 11/2009 | Pinchuk et al. |
| 7,666,216 B2 | 2/2010 | Hogendijk et al. |
| 7,678,068 B2 | 3/2010 | Levine et al. |
| 7,682,647 B2 | 3/2010 | Hossainy et al. |
| 7,686,781 B2 | 3/2010 | Vinten-Johansen |
| 7,691,401 B2 | 4/2010 | Castro et al. |
| 7,695,446 B2 | 4/2010 | Levine et al. |
| 7,698,111 B2 | 4/2010 | Abrahao et al. |
| 7,704,545 B2 | 4/2010 | Kantor |
| 7,731,750 B2 | 6/2010 | Bojarski et al. |
| 7,740,657 B2 | 6/2010 | Brown et al. |
| 7,744,620 B2 | 6/2010 | Pedersen et al. |
| 7,758,535 B2 | 7/2010 | Levine et al. |
| 7,758,642 B2 | 7/2010 | Bojarski et al. |
| 7,758,881 B2 | 7/2010 | Dugan |
| 7,766,861 B2 | 8/2010 | Levine et al. |
| 7,766,973 B2 | 8/2010 | Levine et al. |
| 7,771,382 B2 | 8/2010 | Levine et al. |
| 7,785,615 B2 | 8/2010 | Dave et al. |
| 7,789,915 B2 | 9/2010 | Lavelle et al. |
| 7,803,183 B2 | 9/2010 | Kutryk et al. |
| 7,988,732 B2 | 8/2011 | Bojarski et al. |
| 8,900,620 B2 | 12/2014 | Fulmer et al. |
| 9,381,683 B2 | 7/2016 | Armbruster et al. |
| 9,579,260 B2 | 2/2017 | Fulmer et al. |
| 2001/0039456 A1 | 11/2001 | Boyer et al. |
| 2002/0055749 A1 | 5/2002 | Esnouf et al. |
| 2002/0062147 A1 | 5/2002 | Yang |
| 2002/0187260 A1 | 12/2002 | Sheppard et al. |
| 2003/0088307 A1 | 5/2003 | Shulze et al. |
| 2003/0093111 A1 | 5/2003 | Ken et al. |
| 2003/0107149 A1 | 6/2003 | Yang et al. |
| 2003/0149466 A1 | 8/2003 | Gerberding |
| 2004/0093058 A1 | 5/2004 | Cottone et al. |
| 2004/0093062 A1 | 5/2004 | Glastra |
| 2004/0146546 A1 | 7/2004 | Gravett et al. |
| 2004/0225359 A1 | 11/2004 | Bojarski et al. |
| 2004/0267347 A1 | 12/2004 | Cervantes |
| 2004/0267354 A1 | 12/2004 | Ringeisen et al. |
| 2005/0019404 A1 | 1/2005 | Sung et al. |
| 2005/0129732 A1 | 6/2005 | Rubsamen |
| 2005/0159805 A1 | 7/2005 | Weber et al. |
| 2005/0181977 A1 | 8/2005 | Hunter et al. |
| 2005/0209629 A1 | 9/2005 | Kerr et al. |
| 2005/0209704 A1 | 9/2005 | Maspero et al. |
| 2005/0246021 A1 | 11/2005 | Ringeisen et al. |
| 2005/0261782 A1 | 11/2005 | Hoganson |
| 2005/0278011 A1 | 12/2005 | Peckham |
| 2006/0093646 A1 | 5/2006 | Cima et al. |
| 2006/0234061 A1 | 10/2006 | Buckel et al. |
| 2006/0259122 A1 | 11/2006 | Eliseev |
| 2006/0263355 A1 | 11/2006 | Quan et al. |
| 2006/0276906 A1 | 12/2006 | Hoag et al. |
| 2006/0286137 A1 | 12/2006 | Sandhu et al. |
| 2007/0038299 A1 | 2/2007 | Stone et al. |
| 2007/0118211 A1 | 5/2007 | Gazza |
| 2007/0141103 A1 | 6/2007 | Benedict et al. |
| 2007/0142892 A1 | 6/2007 | Dave et al. |
| 2007/0198040 A1 | 8/2007 | Buevich et al. |
| 2007/0213801 A1 | 9/2007 | Kutryk et al. |
| 2007/0255422 A1 | 11/2007 | Wei et al. |
| 2008/0033548 A1 | 2/2008 | Xuenong et al. |
| 2008/0057096 A1 | 3/2008 | Ibsen |
| 2008/0097570 A1 | 4/2008 | Thornton et al. |
| 2008/0107711 A1 | 5/2008 | Shelokov |
| 2008/0112892 A1 | 5/2008 | Veenstra et al. |
| 2008/0125847 A1 | 5/2008 | Krever et al. |
| 2008/0128315 A1 | 6/2008 | Buevich et al. |
| 2008/0132922 A1 | 6/2008 | Buevich et al. |
| 2008/0132992 A1* | 6/2008 | Bates ............... A61F 2/02 623/1.13 |
| 2008/0195218 A1 | 8/2008 | Jones |
| 2008/0241212 A1 | 10/2008 | Moses et al. |
| 2008/0262630 A1 | 10/2008 | Fulmer et al. |
| 2009/0012595 A1 | 1/2009 | Seliktar et al. |
| 2009/0018640 A1 | 1/2009 | State |
| 2009/0062899 A1 | 3/2009 | Dang et al. |
| 2009/0069904 A1 | 3/2009 | Picha |
| 2009/0076449 A1 | 3/2009 | Geis et al. |
| 2009/0076508 A1 | 3/2009 | Weinans et al. |
| 2009/0081276 A1 | 3/2009 | Alsberg et al. |
| 2009/0081278 A1 | 3/2009 | De Graaff et al. |
| 2009/0092654 A1 | 4/2009 | de Juan, Jr. et al. |
| 2009/0118817 A1 | 5/2009 | Sandhu et al. |
| 2009/0130167 A1 | 5/2009 | Shelton et al. |
| 2009/0143851 A1 | 6/2009 | Paul, Jr. |
| 2009/0192474 A1 | 7/2009 | Wei et al. |
| 2009/0192609 A1 | 7/2009 | Klabunde et al. |
| 2009/0198197 A1 | 8/2009 | Bischoff et al. |
| 2009/0227948 A1 | 9/2009 | Ruehrig |
| 2009/0233045 A1 | 9/2009 | Slama et al. |
| 2009/0234453 A1 | 9/2009 | Steinberg |
| 2009/0289395 A1 | 11/2009 | Chou |
| 2010/0004729 A1 | 1/2010 | Chew et al. |
| 2010/0028390 A1 | 2/2010 | Cleary et al. |
| 2010/0028402 A1 | 2/2010 | Dobrovolskaia et al. |
| 2010/0070015 A1 | 3/2010 | Schneider et al. |
| 2010/0211153 A1 | 8/2010 | Cook et al. |
| 2010/0222826 A1 | 9/2010 | Bojarski et al. |
| 2010/0228333 A1 | 9/2010 | Drasler et al. |
| 2010/0233238 A1 | 9/2010 | Tenney et al. |
| 2010/0241214 A1 | 9/2010 | Holzer et al. |
| 2010/0247600 A1 | 9/2010 | Xia et al. |

(56) References Cited

U.S. PATENT DOCUMENTS

| | | | |
|---|---|---|---|
| 2010/0249783 A1* | 9/2010 | Trieu | A61L 31/04 606/76 |
| 2011/0144688 A1 | 6/2011 | Reiss et al. | |
| 2011/0244047 A1 | 10/2011 | Asari et al. | |
| 2011/0268781 A1 | 11/2011 | Cleek et al. | |
| 2011/0282362 A1 | 11/2011 | Bojarski et al. | |
| 2012/0010636 A1 | 1/2012 | Boey et al. | |
| 2012/0016388 A1 | 1/2012 | Houard et al. | |
| 2012/0027833 A1 | 2/2012 | Zilberman | |
| 2013/0129807 A1 | 5/2013 | Devore et al. | |
| 2013/0289621 A1 | 10/2013 | Fulmer et al. | |

FOREIGN PATENT DOCUMENTS

| | | | |
|---|---|---|---|
| CN | 1638743 A | 7/2005 | |
| CN | 101402736 A | 4/2009 | |
| CN | 101437571 | 5/2009 | |
| CN | 101912663 A | 12/2010 | |
| CN | 102958557 A | 3/2013 | |
| DE | 3939363 A1 | 6/1991 | |
| EP | 0013638 A1 | 7/1980 | |
| EP | 0323800 A1 | 7/1989 | |
| EP | 0371819 A2 * | 6/1990 | B32B 7/06 |
| EP | 0371819 A2 | 6/1990 | |
| EP | 0523926 A2 | 1/1993 | |
| EP | 0539751 A1 | 5/1993 | |
| EP | 0578998 A1 | 1/1994 | |
| EP | 0604697 A1 | 7/1994 | |
| EP | 0737703 A2 | 10/1996 | |
| EP | 1216717 A1 | 6/2002 | |
| EP | 1272131 A2 | 1/2003 | |
| EP | 1294323 A2 | 3/2003 | |
| EP | 1374817 A1 | 1/2004 | |
| EP | 1395303 A2 | 3/2004 | |
| EP | 1482996 B1 | 11/2005 | |
| EP | 1812990 A1 | 8/2007 | |
| EP | 1820463 A2 | 8/2007 | |
| EP | 1463463 B1 | 2/2008 | |
| EP | 1913903 A2 | 4/2008 | |
| EP | 2052700 A1 | 4/2009 | |
| EP | 2080603 A1 | 7/2009 | |
| FR | 1181333 A | 6/1959 | |
| FR | 1183333 A | 7/1959 | |
| JP | 02-121652 | 5/1990 | |
| JP | 03-085179 A | 4/1991 | |
| JP | 04-221538 | 8/1992 | |
| JP | 07-044936 B2 | 5/1995 | |
| JP | 07-313586 | 12/1995 | |
| JP | 08-024347 | 1/1996 | |
| JP | 08-224297 | 9/1996 | |
| JP | 09-173364 A | 7/1997 | |
| JP | 09-201330 | 8/1997 | |
| JP | 2002-058741 A | 2/2002 | |
| JP | 2003-527193 A | 9/2003 | |
| JP | 2008-531699 | 8/2008 | |
| JP | 2008-224297 A | 9/2008 | |
| JP | 2008-535700 A | 9/2008 | |
| JP | 2009-511196 A | 3/2009 | |
| JP | 2009-240783 A | 10/2009 | |
| JP | 2011-216178 A | 10/2011 | |
| JP | 2013-005984 A | 1/2013 | |
| RU | 2234419 C2 | 8/2004 | |
| RU | 2300792 C2 | 6/2007 | |
| RU | 77539 U1 | 10/2008 | |
| SU | 683207 A1 | 3/1985 | |
| WO | 98/51240 A1 | 11/1998 | |
| WO | 99/51171 A1 | 10/1999 | |
| WO | 99/62416 A1 | 12/1999 | |
| WO | 00/12147 A1 | 3/2000 | |
| WO | 01/12107 A1 | 2/2001 | |
| WO | 01/32100 A2 | 5/2001 | |
| WO | 01/70135 A2 | 9/2001 | |
| WO | 01/76514 A2 | 10/2001 | |
| WO | 01/97721 A2 | 12/2001 | |
| WO | 02/51463 A2 | 7/2002 | |
| WO | 03/22165 A1 | 3/2003 | |
| WO | 03/59213 A2 | 7/2003 | |
| WO | 20041010854 A2 | 2/2004 | |
| WO | 20051009499 A1 | 2/2005 | |
| WO | 20051049105 A2 | 6/2005 | |
| WO | 20061023261 A2 | 3/2006 | |
| WO | 20061050106 A1 | 5/2006 | |
| WO | 20061108520 A1 | 10/2006 | |
| WO | 20071047420 A2 | 4/2007 | |
| WO | WO2007/047420 A2 * | 4/2007 | A61F 2/02 |
| WO | 20071053022 A2 | 5/2007 | |
| WO | 20071092417 A1 | 8/2007 | |
| WO | 20081121816 A2 | 10/2008 | |
| WO | 20101135440 A1 | 11/2010 | |
| WO | 20131013172 A1 | 1/2013 | |

OTHER PUBLICATIONS

Stile et al., "Synthesis and Characterization of Injectable Poly(N-isopropylacrylamide)-Based Hydrogels That Support Tissue Formation in Vitro", Macromolecules, 32, (1999), 7370-7379.

Second Office Action for Chinese Patent Application No. 200680037881.8 dated Dec. 23, 2011.

Schmidt et al., Antibiotic in vivo/in vitro release, histocompatibility and biodegradation of gentamicin implants based on lactic acid polymers and copolymers, Nov. 1995, Journal of Controlled Release, vol. 37, Issues 1-2, pp. 83-84.

Pineros-Fernandez, A. et al., "Caprosyn*, Another Major Advance in Synthetic Monofilament Absorbable Suture", Journal of Long-Term Effects of Medical Implants, 2004, 14(5), 359-368.

Pandey et al., Characterization of In-vitro Release of Gentamicin from Biodegradable Polymer Thin Films Microstructure-Function Relationship by Confocal Raman Microscopy, Apr. 2015, Journal of Biomedical Materials Research.

Office action dated Oct. 18, 2011 for Japanese Patent Application No. 2008-535700.

Mingeot-Leclercq et al., "Aminoglycosides: Nephrotoxicity", Antimicrobial Agents and Chemotherapy, May 1999, 43 (5), 1003-1012.

Machine Translation of DE 3939363 A1, Jun. 1991, 9 pages.

Lucke, M, et al., "Gentamicin coating of metallic implants reduces implant-related osteomyelitis in rats", Bone; vol. 32, (2003), 521-531.

Kaneko, Y., et al., "Synthesis and Swelling—deswelling kinetics of poly(N-isopropylacrylamide) hydrogels grafted with LCST modulated polymers", Journal of Biomaterials Science Polymer Edition 10(11) (1999),1079-1091.

Japanese Application No. 2002-506661, Official Notice of Reason for the Final Rejection dated Jul. 11, 2008, (w/ English Translation), 4 pgs.

Japanese Application No. 2002-506661, Notice of the Reason for the Rejection dated Feb. 27, 2008, (w/ English Translation), 7 pgs.

International Search Report for Application No. PCT/US2006/40038, dated Sep. 25, 2007, 5 pages.

International Patent Application No. PCT/US2012/071708: International Search Report and Written Opinion dated Jun. 5, 2013, 22 pages.

International Application Serial No. PCT/US06/40038, International Preliminary Report on Patentability dated Sep. 3, 2008, 7 pages.

Huang et al., On the importance and mechanisms of burst release in matrix-controlled drug delivery systems, Jun. 2001, Journal of Controlled Release, vol. 73, Issues 2-3, pp. 121 -136.

Gupta et al., Cefoperazone sodium impregnated polycaprolactone composite implant for osteomyelitis, Indian J. Pharm Sci, Jul.-Aug. 2009, 71(4) 377-381.

Gosau et al., "Release of Gentamicin Sulphate From Biodegradable PLGA-Implants Produced by Hot Melt Extrusion", Pharmazie, 2010.

Fredenberg et al., The mechanisms of drug release in polyl(lactic-co-glycolic acid)-based delivery systems—A review, Aug. 2011, International Journal of Pharmaceutics, vol. 415, Issues 1-2, pp. 34-52.

(56) References Cited

OTHER PUBLICATIONS

Final Office Action for Japanese Patent Application No. 2008-535700 dated May 24, 2012.
European Patent Application No. 04750971.6, Communication dated Jun. 12, 2008, 5 pages.
Dorta et al., Potential applications of PLGA film-implants in modulating in vitro drugs release, Nov. 2002, International Journal of Pharmaceutics, vol. 248, Issues 1-2, pp. 149-156.
Darouiche, "Treatment of Infections Associated with Surgical Implants", The New England Journal of Medicine, Apr. 2004, 350(14), 1422-1429.
Bailey, "A Meta-Analysis of Extended-Interval Dosing Versus Multiple Daily Dosing of Aminoglycosides", Clinical Infectious Diseases, May 1997, 24, 786-795.
Aviv et al., "Gentamicin-Loaded Bioresorbable Films for Prevention of Bacterial Infections Associated with Orthopedic Implants", Journal of Biomedical Materials Research Part 1, Mar. 2007, 10 pages.
Louis et al., "Resorbable Mesh as a Containment System in Reconstruction of the Atrophic Mandible Fracture", J Oral Maxillofac Surg, 62, pp. 719-723, Jun. 2004.

\* cited by examiner

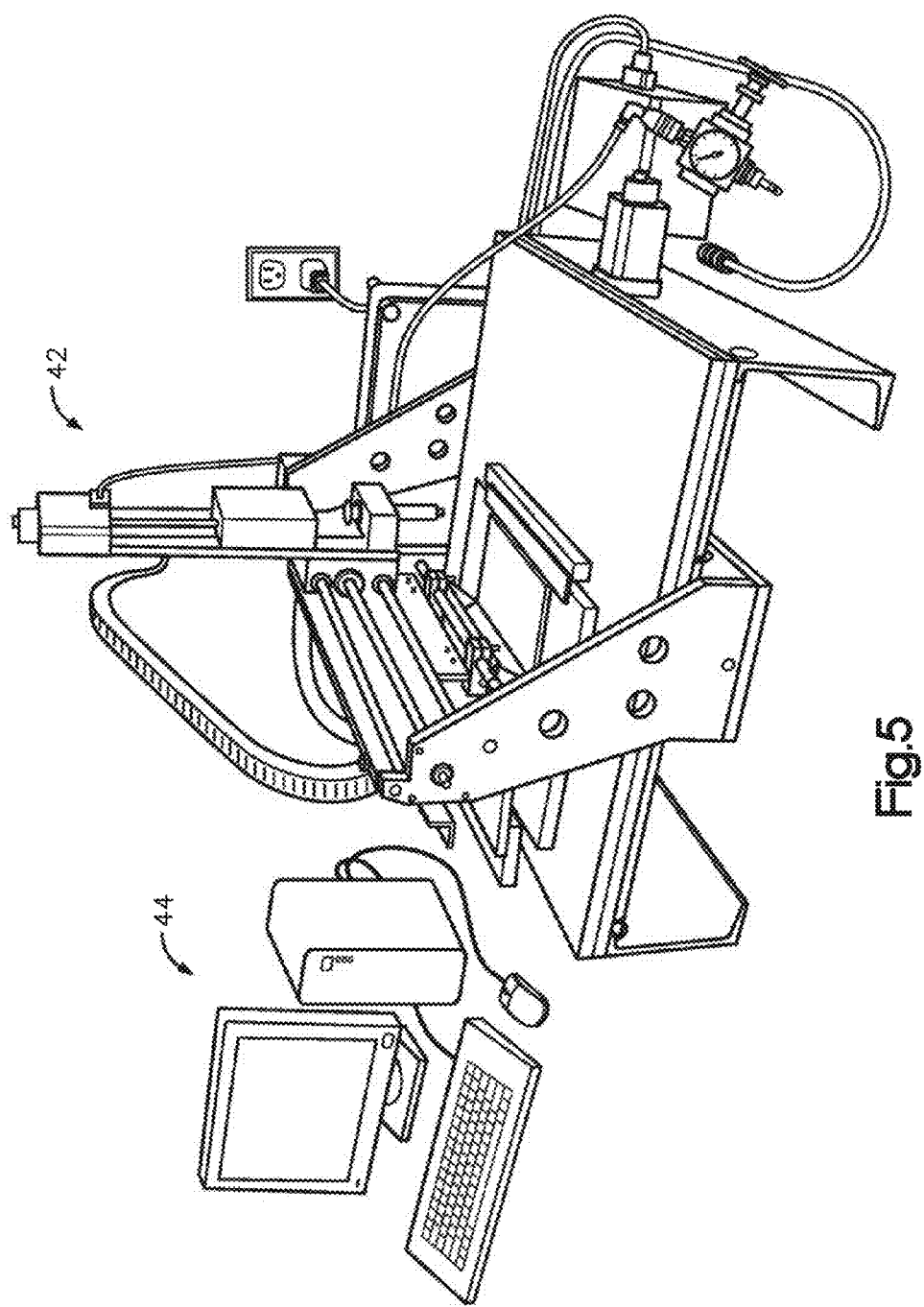

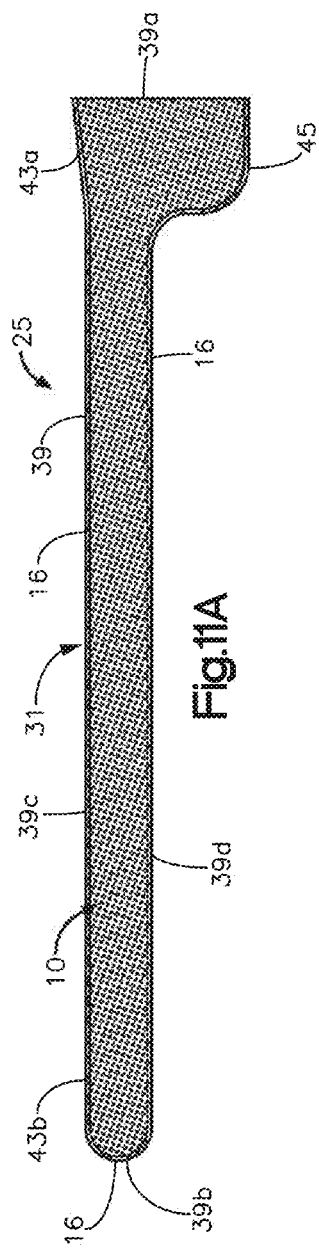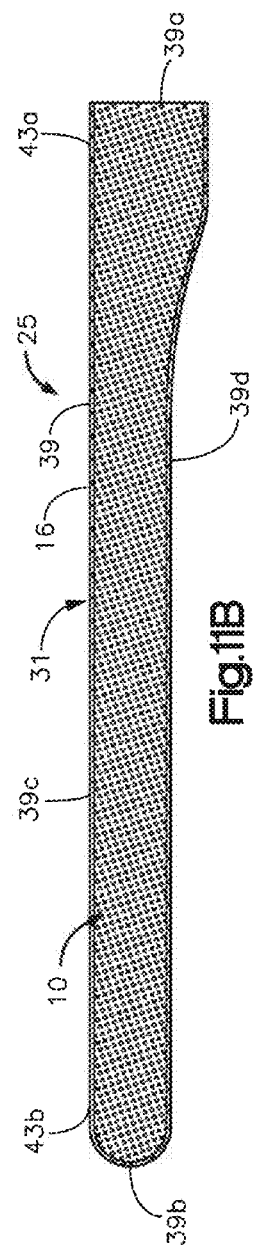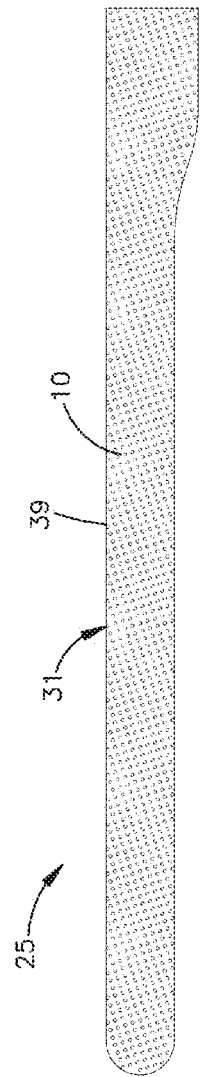

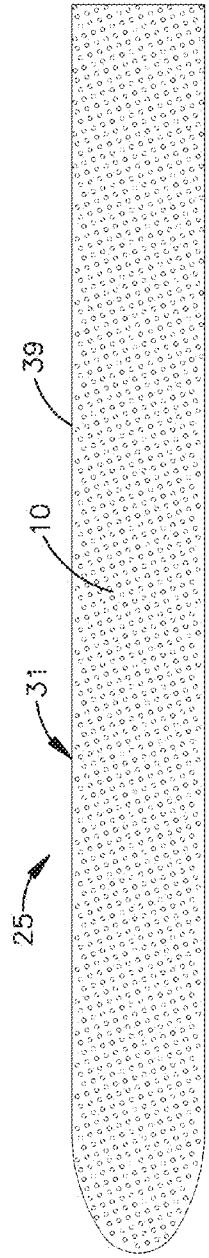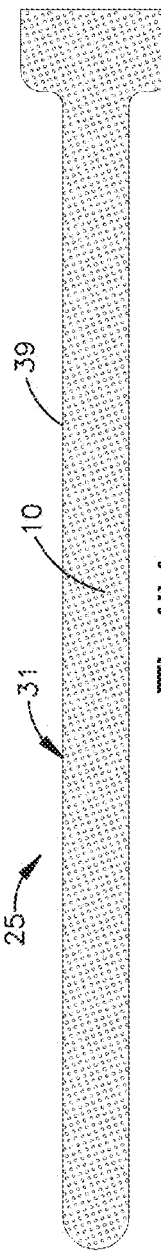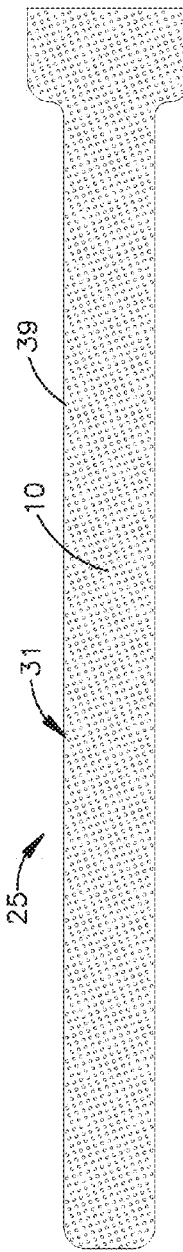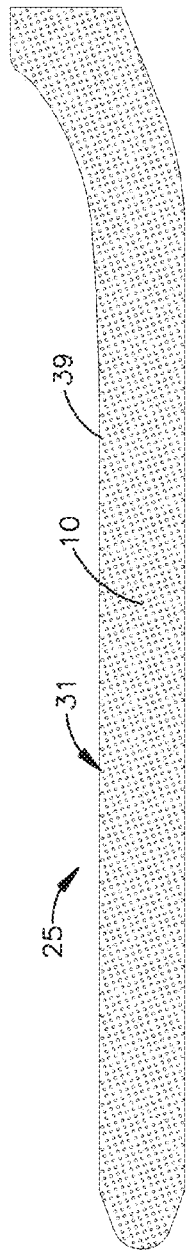

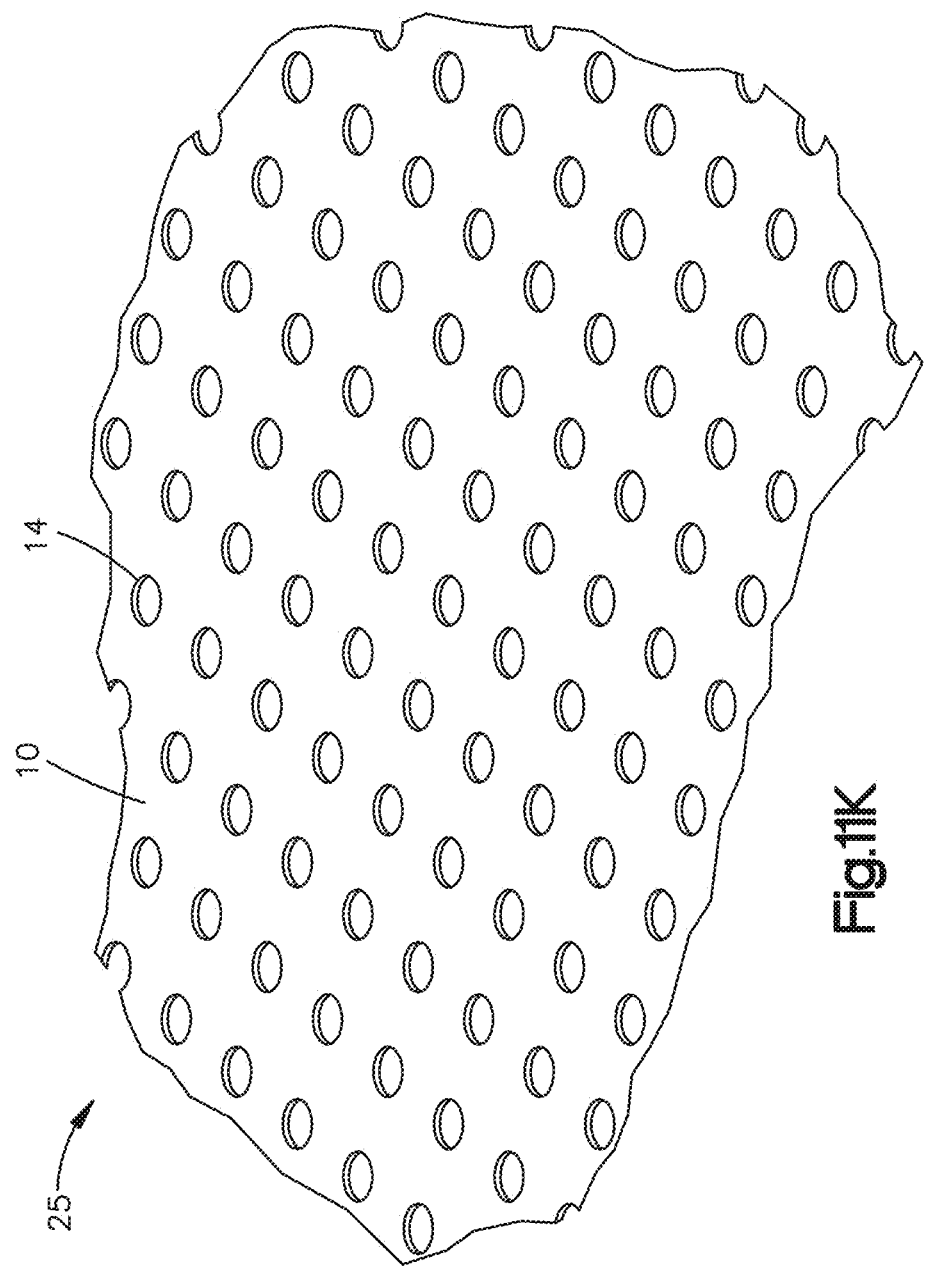

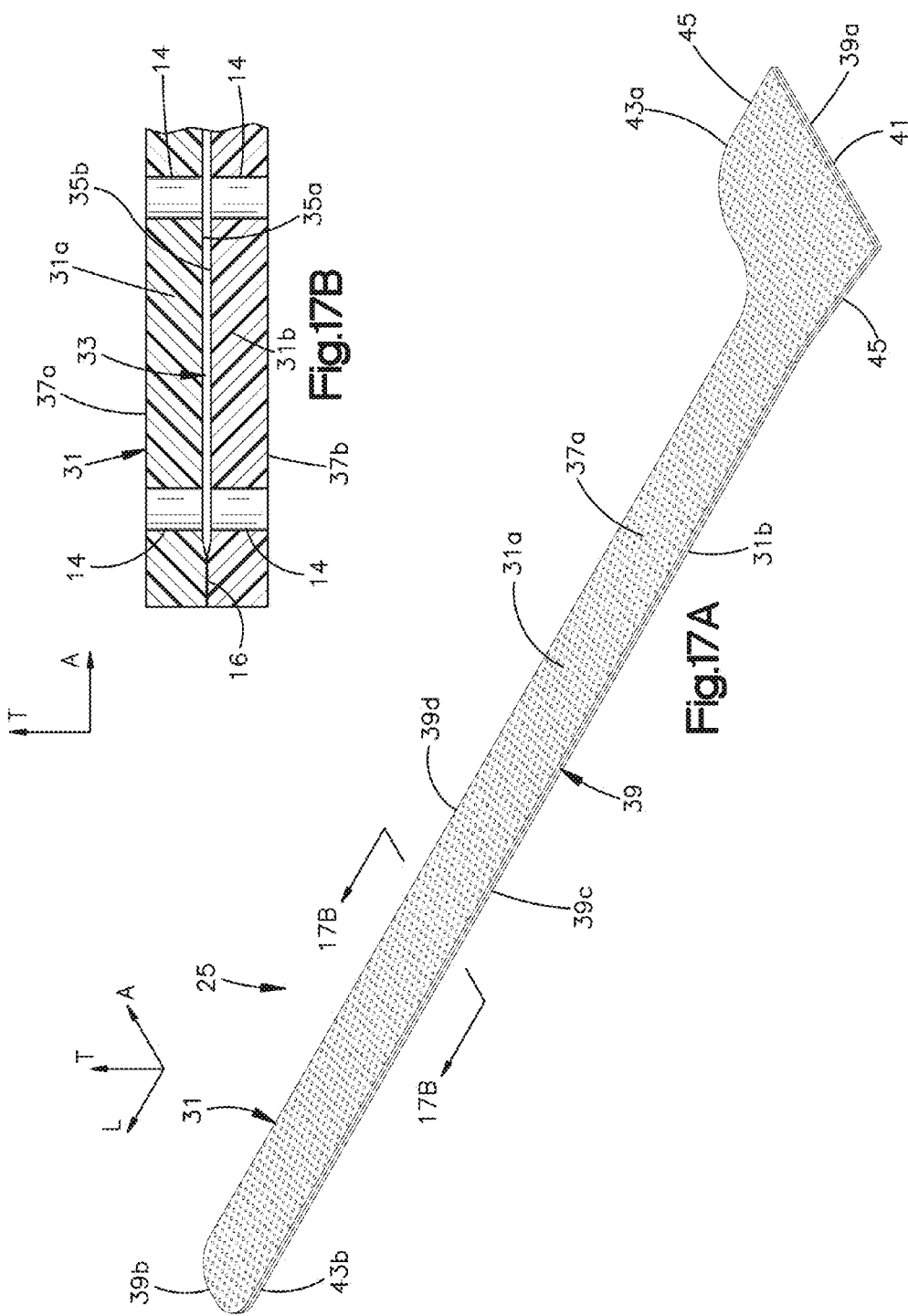

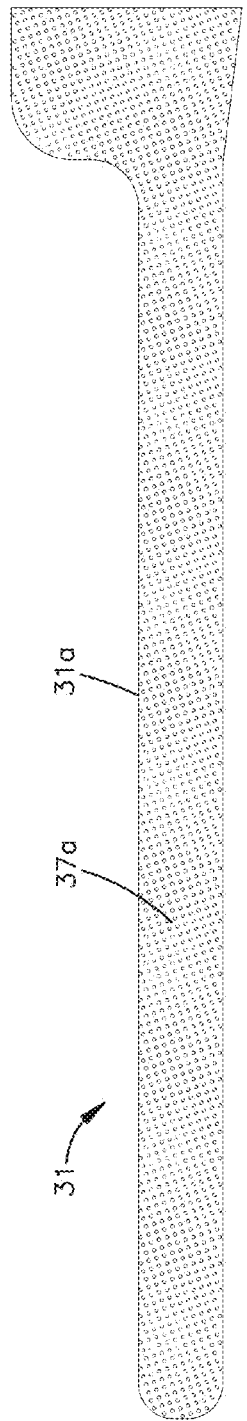
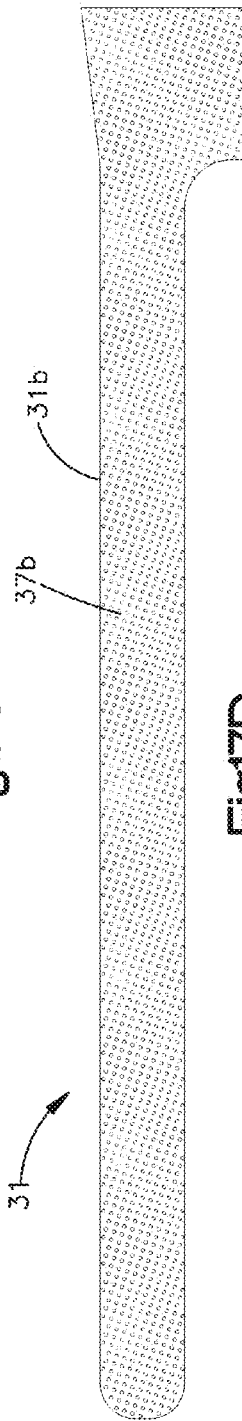
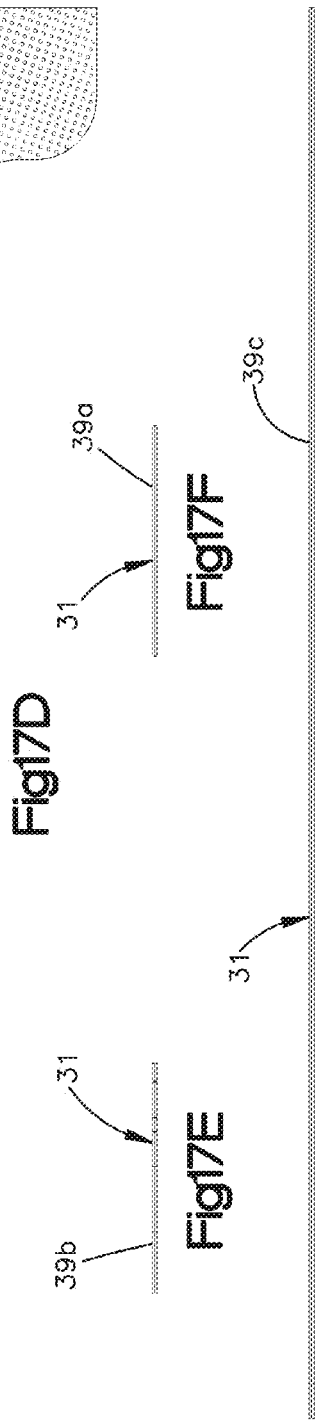
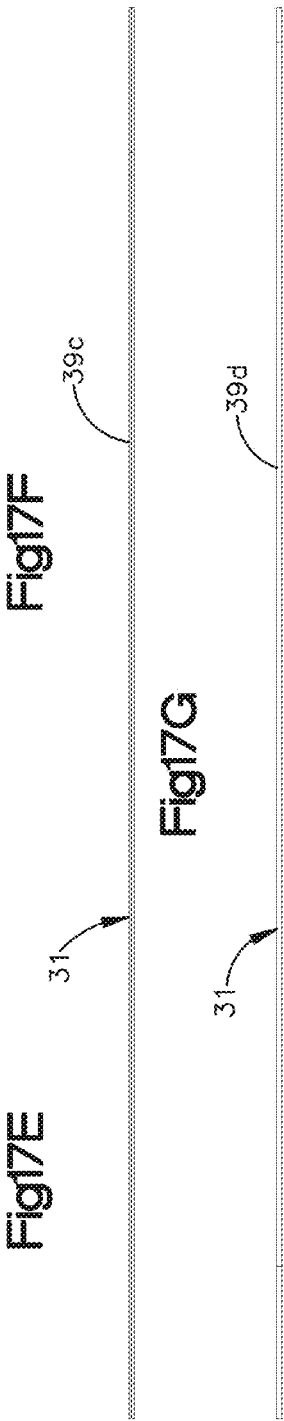
Fig17C  Fig17D  Fig17E  Fig17F  Fig17G  Fig17H

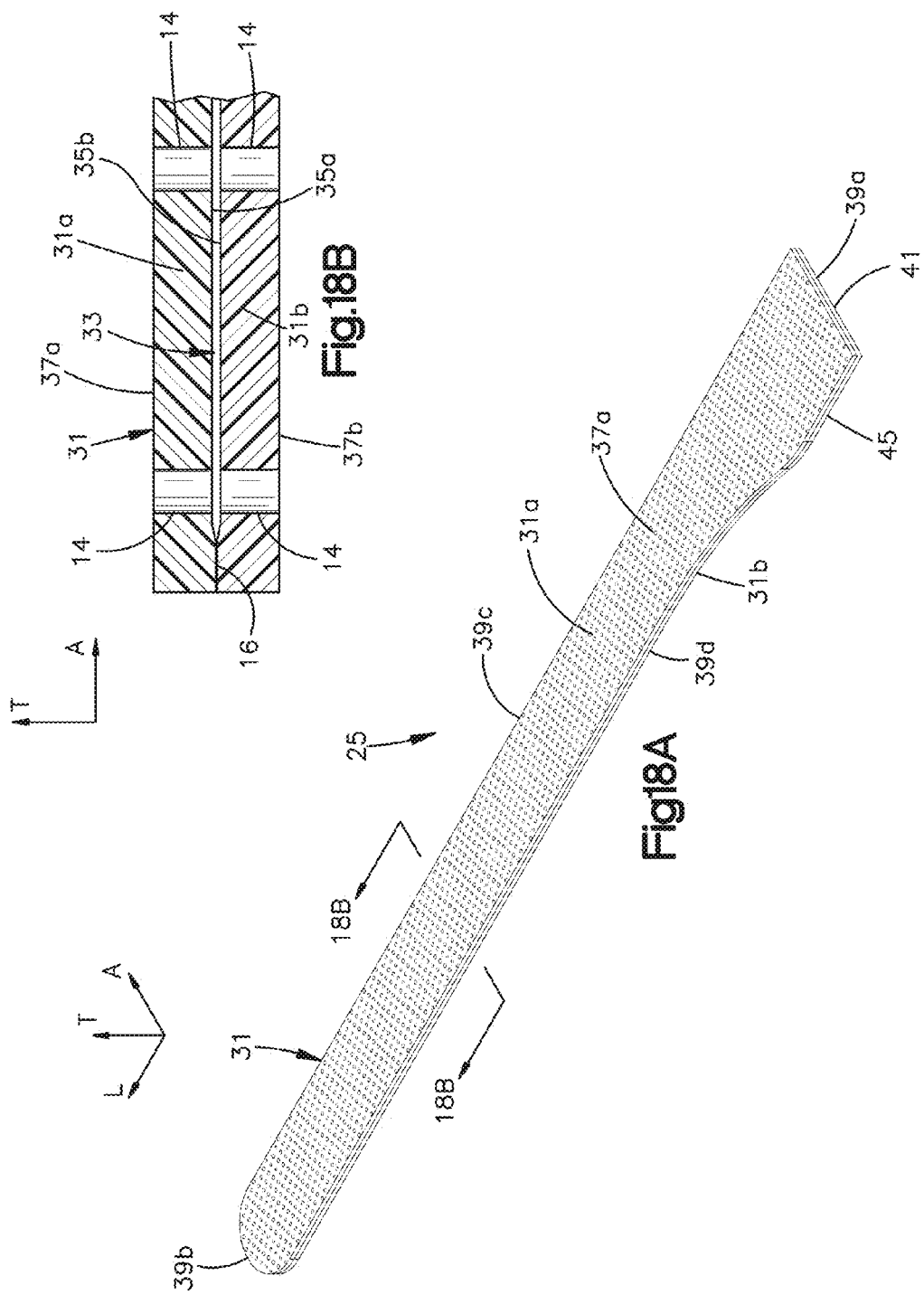

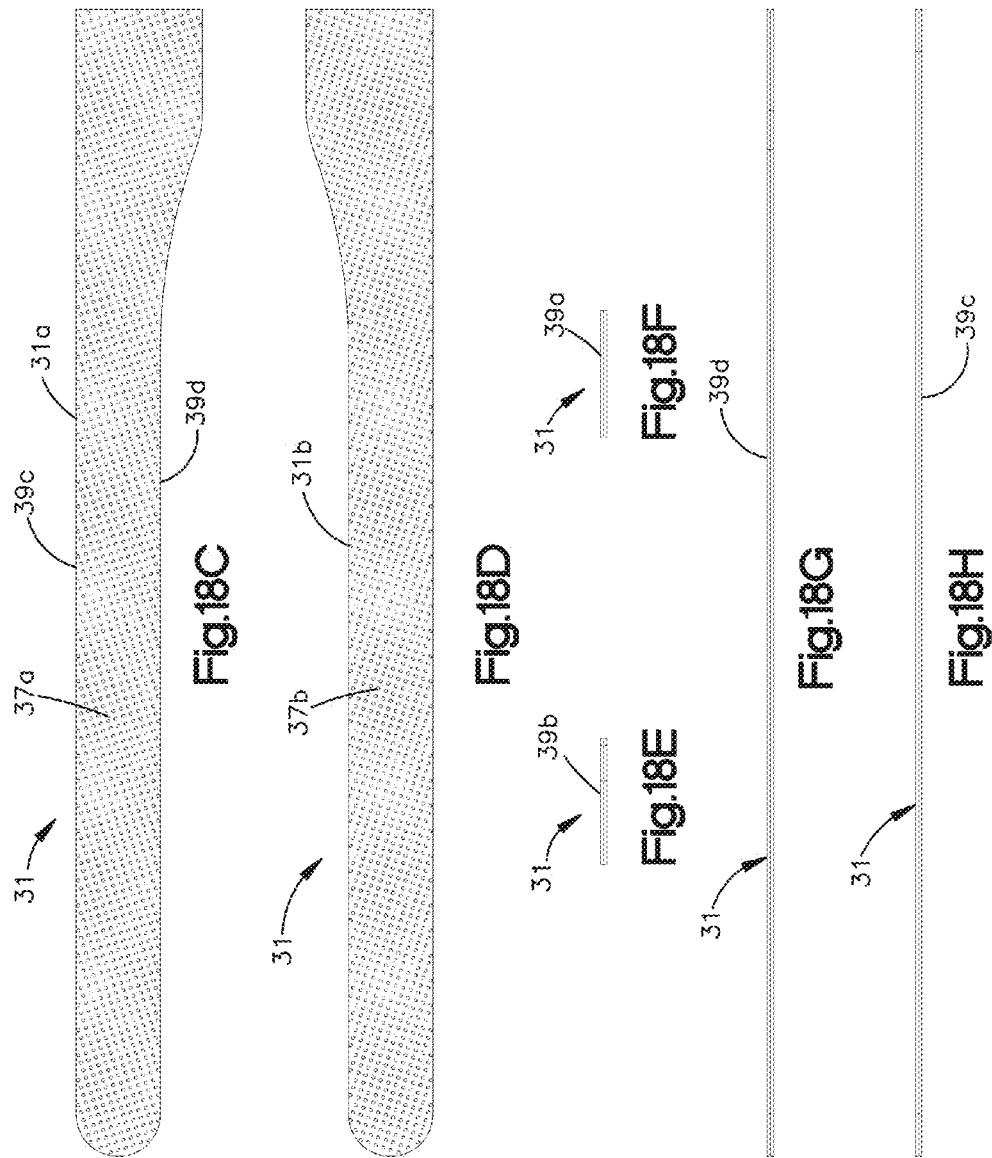

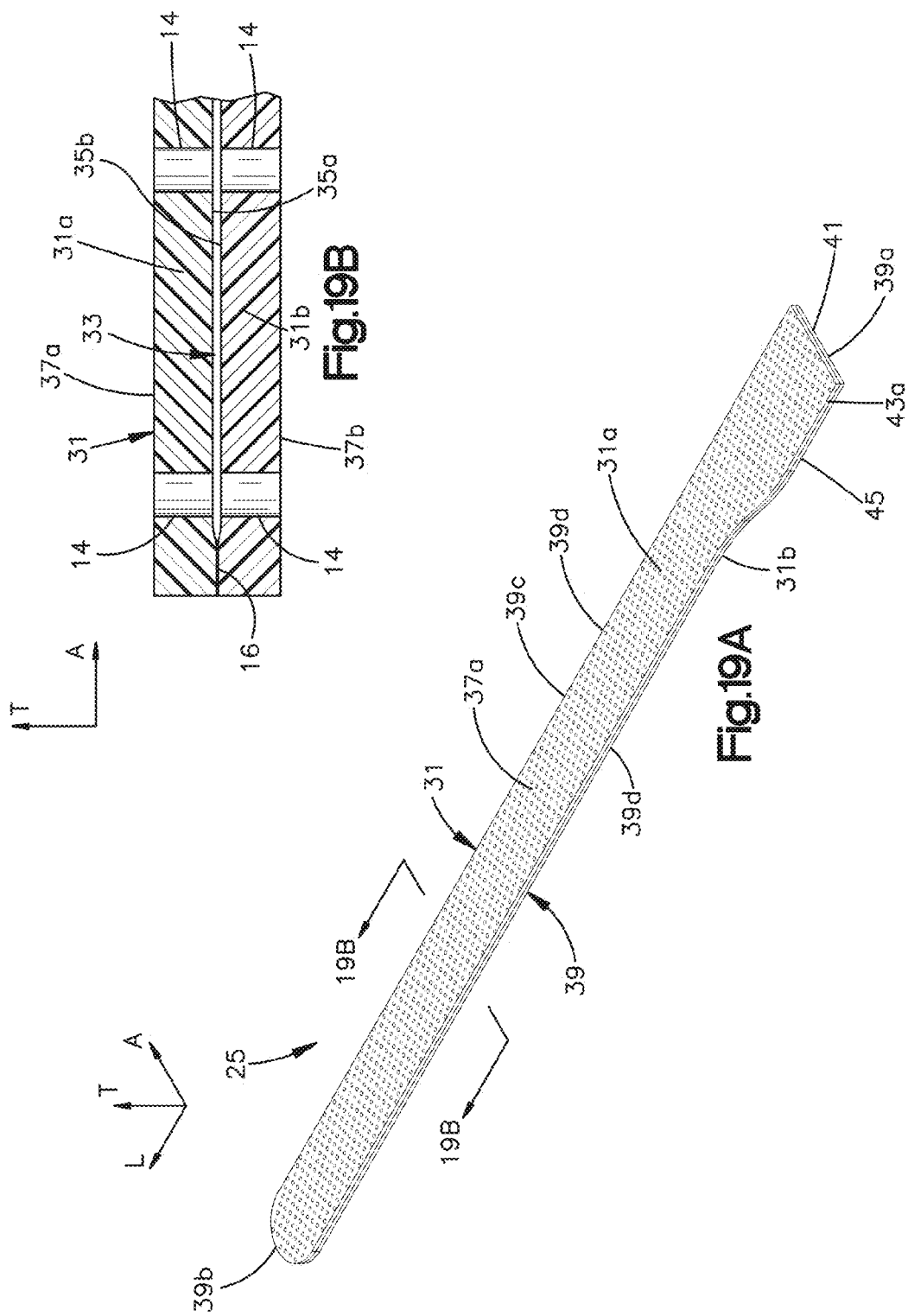

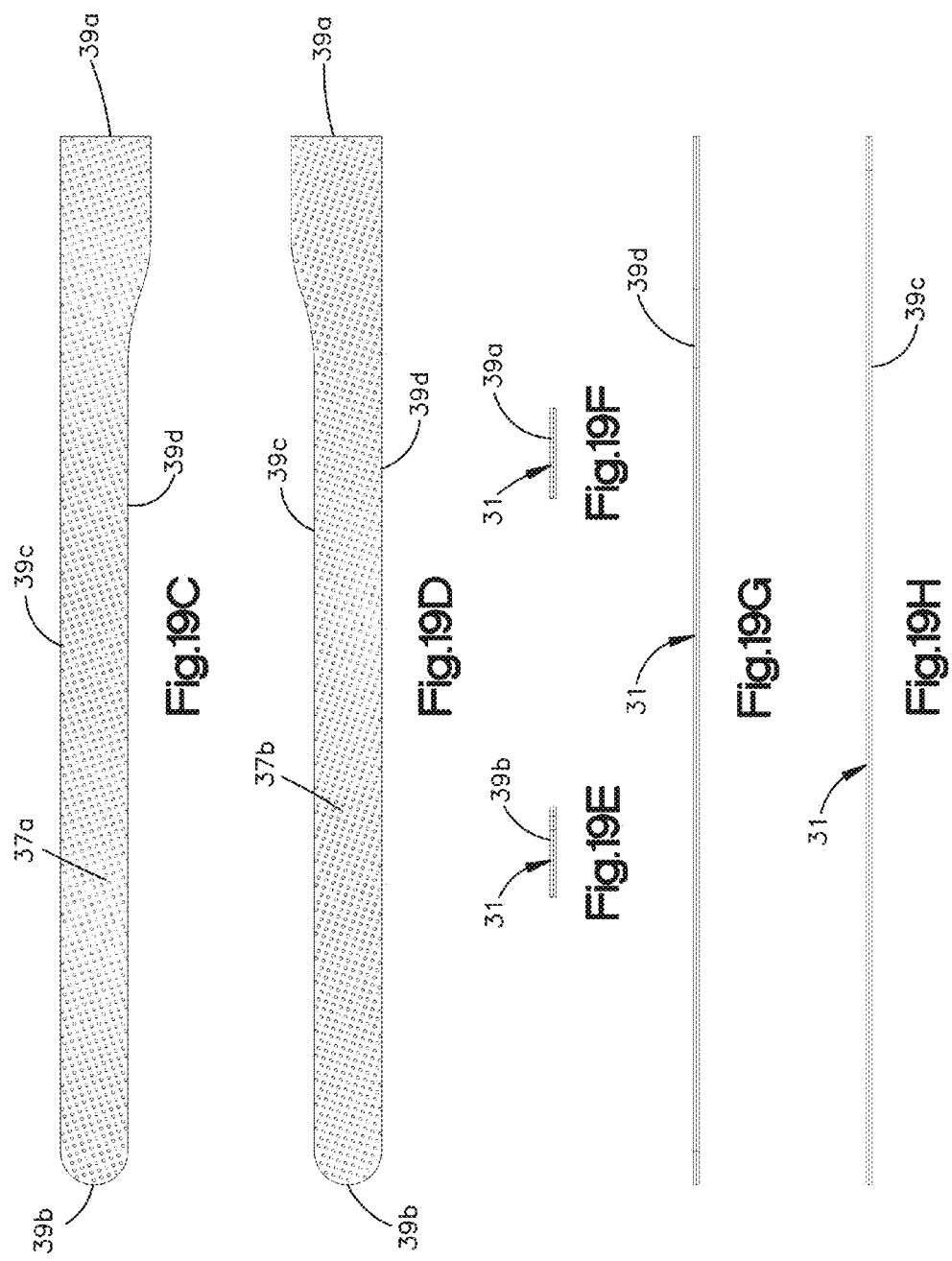

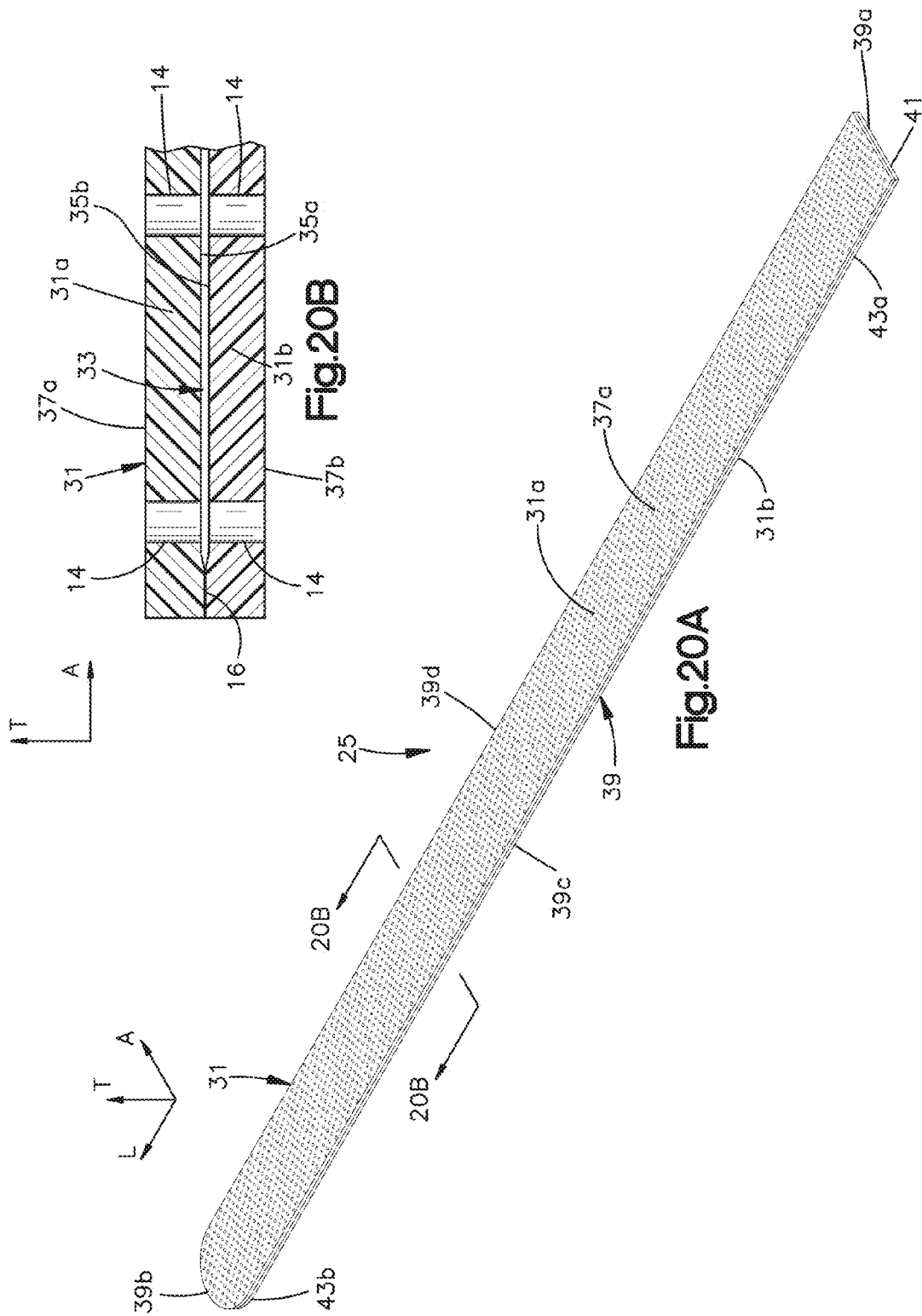

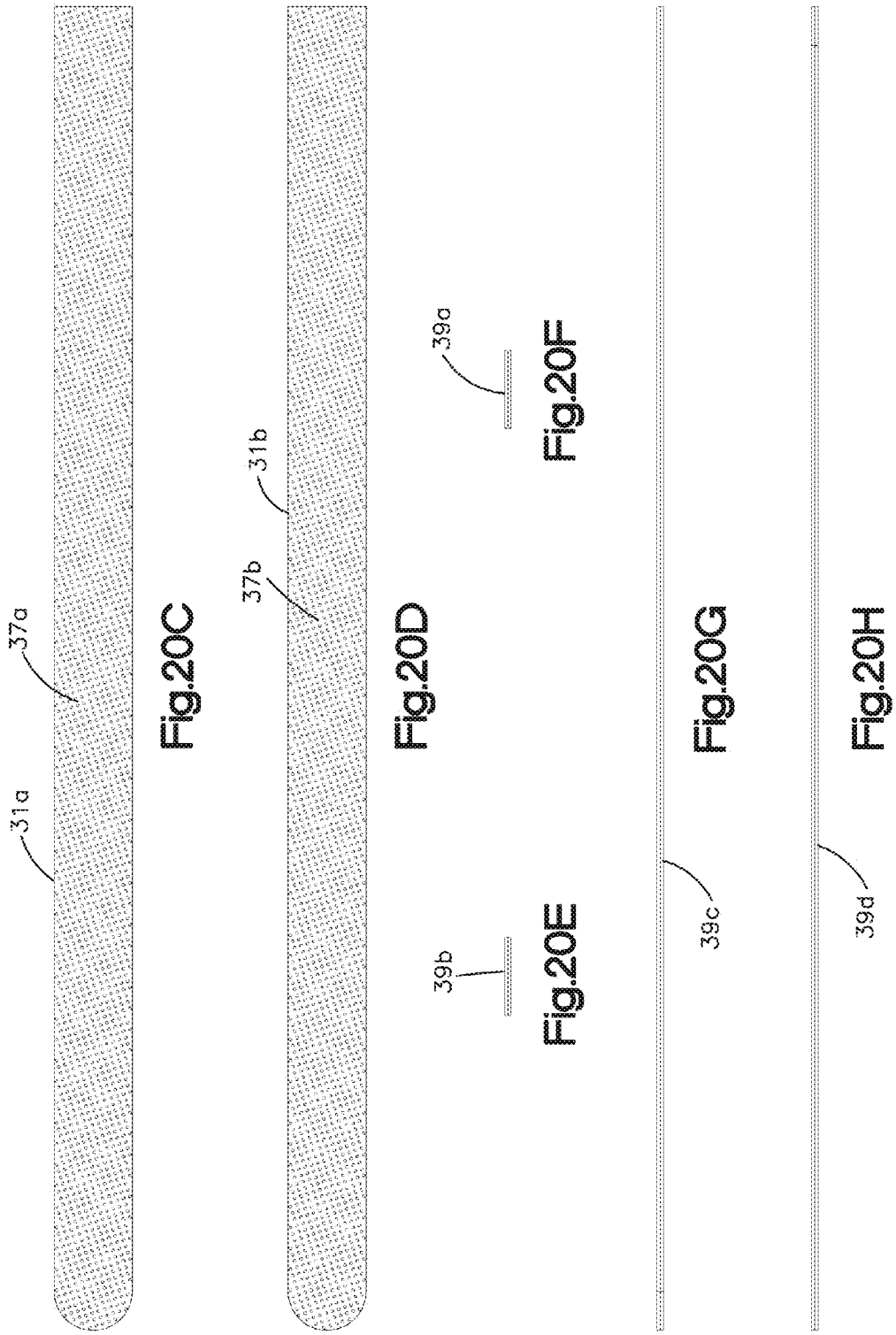

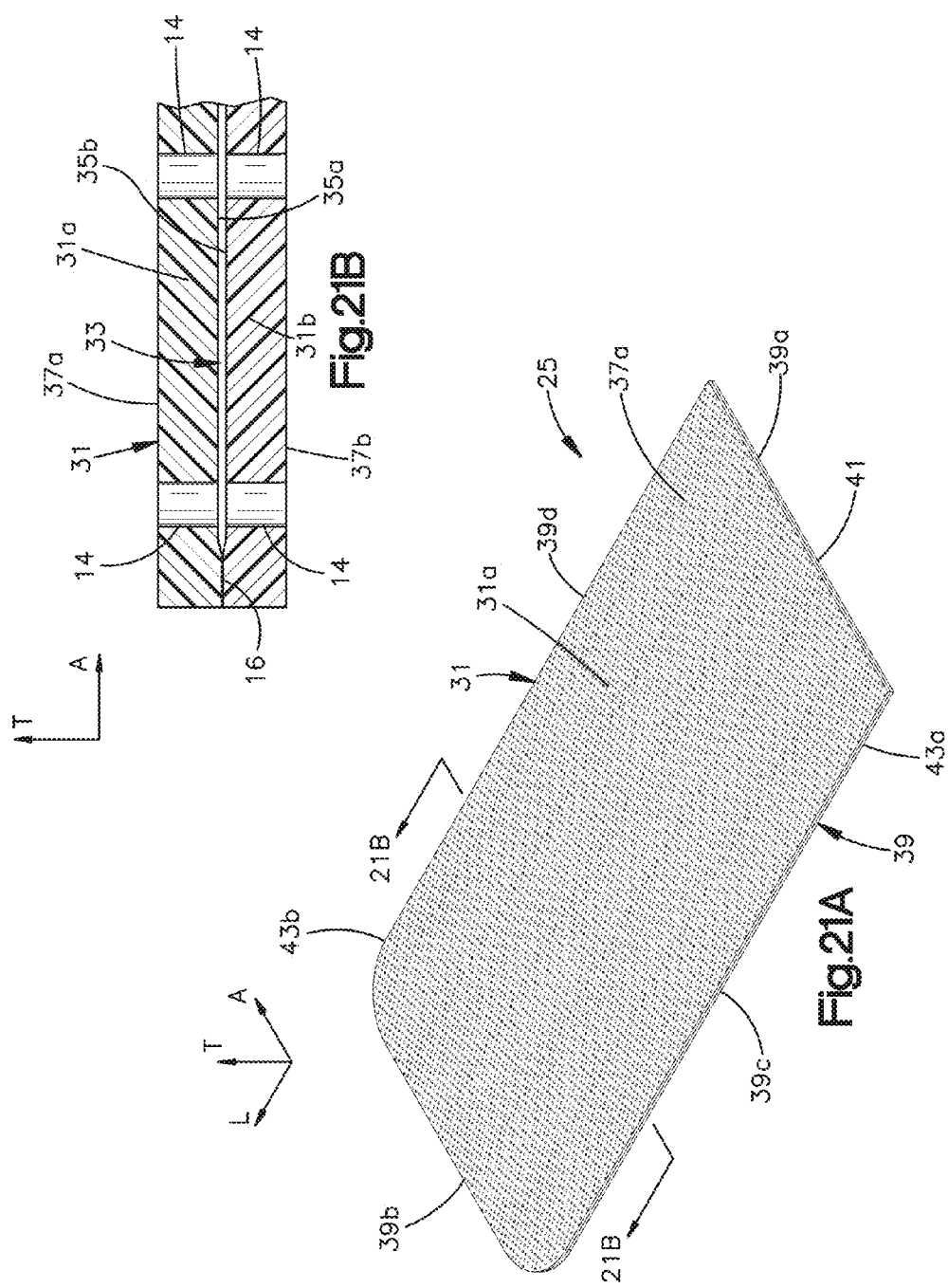

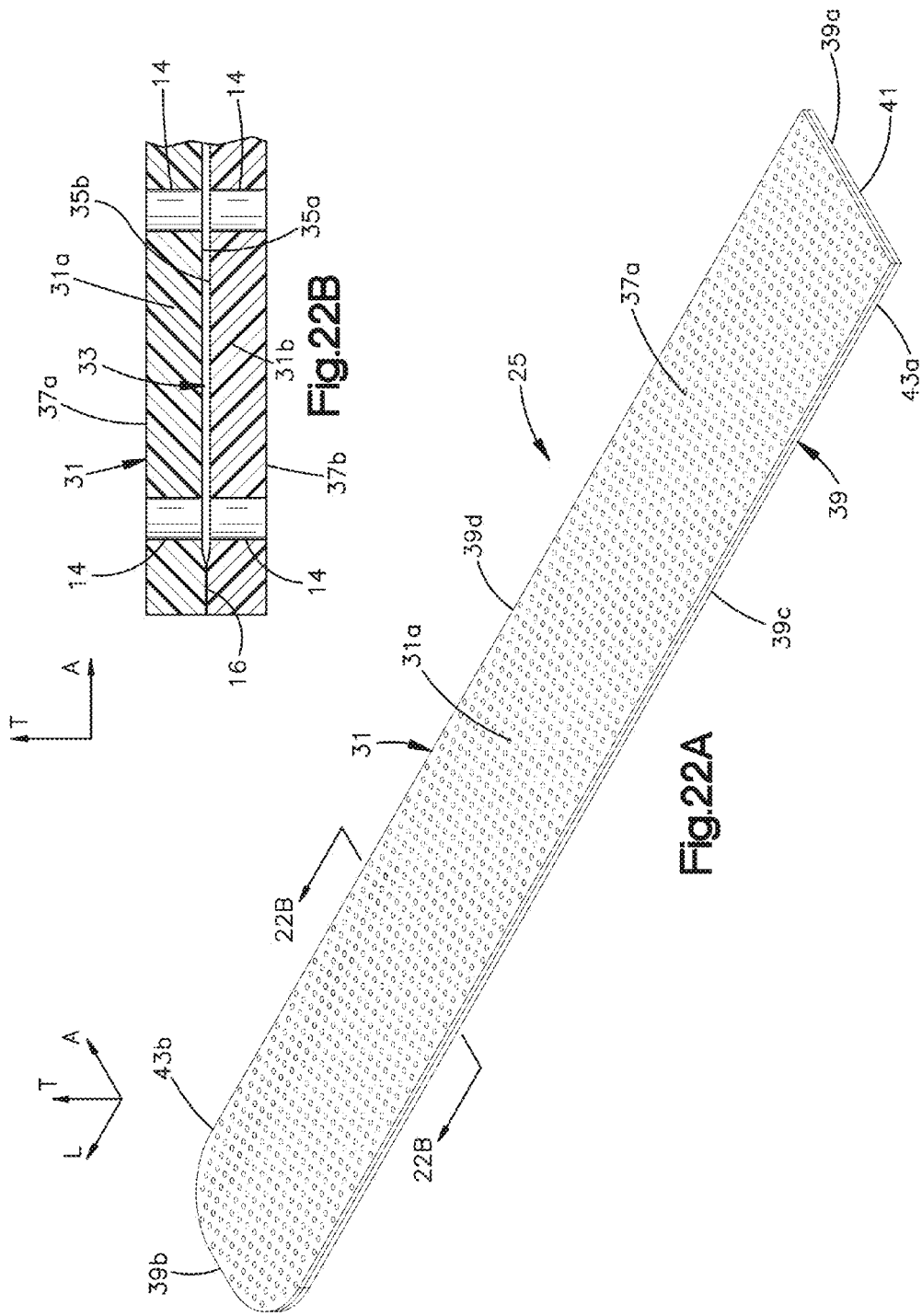

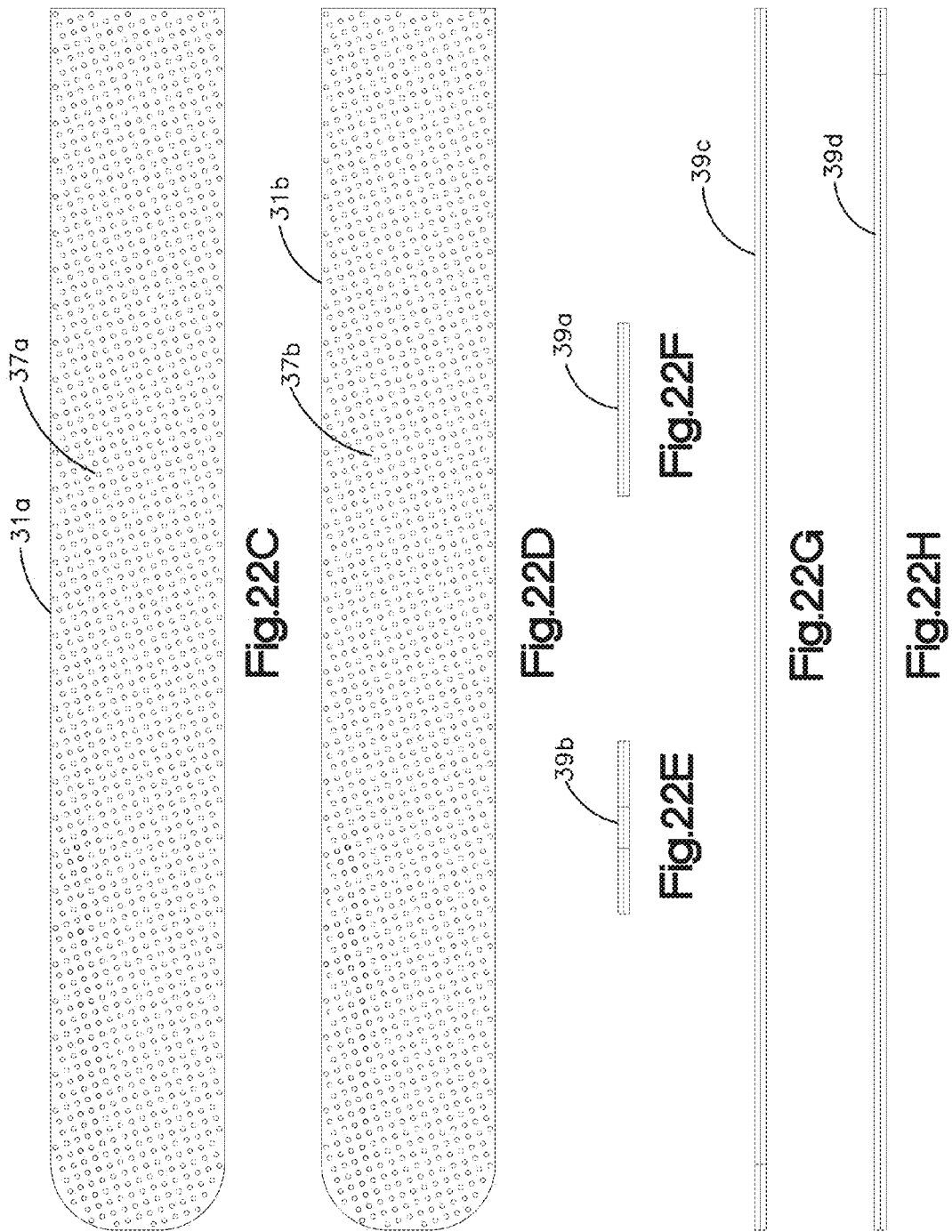

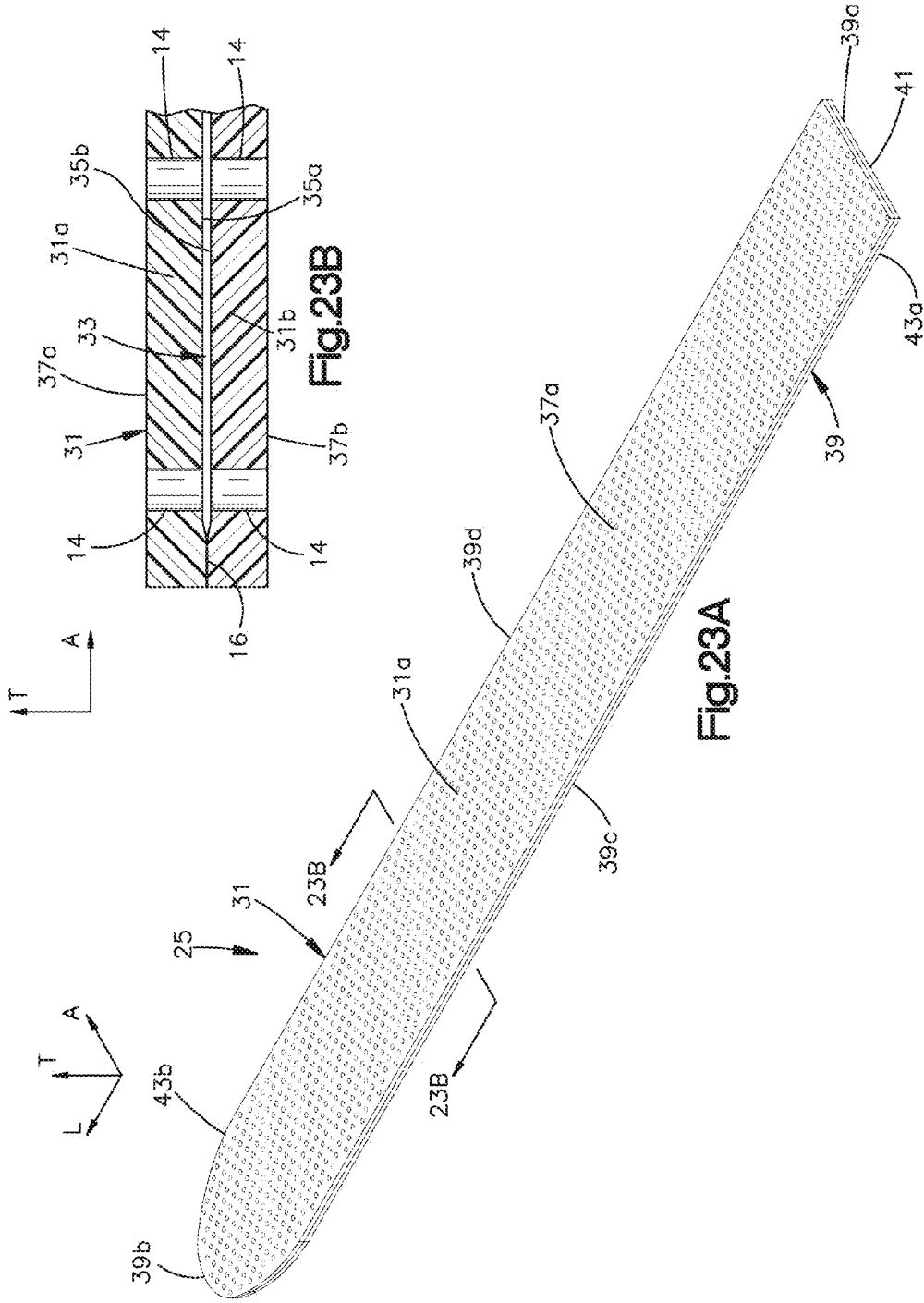

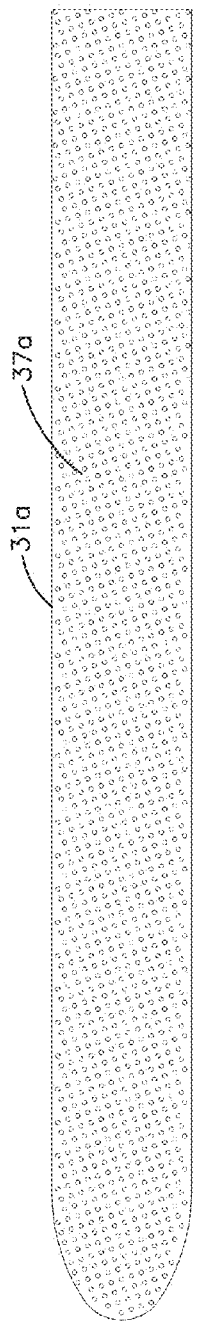
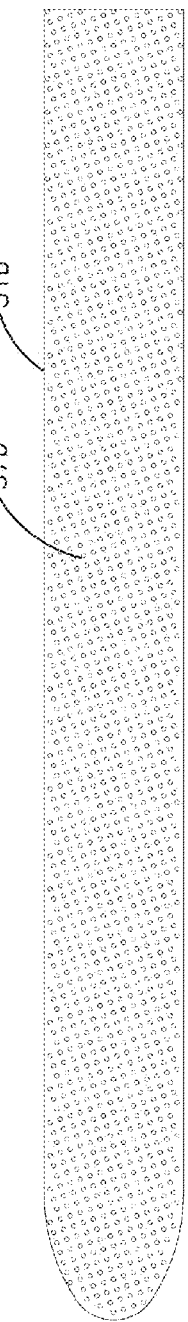
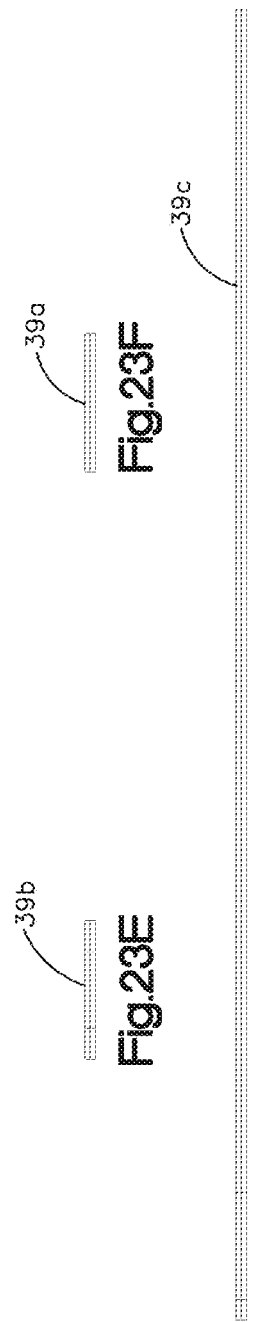
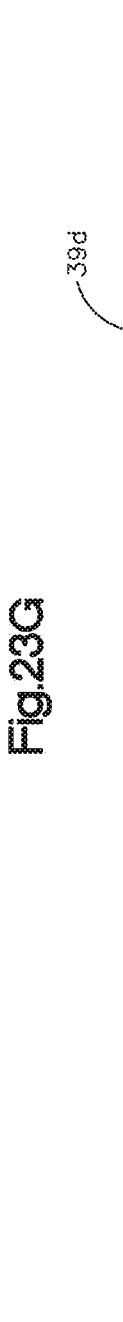

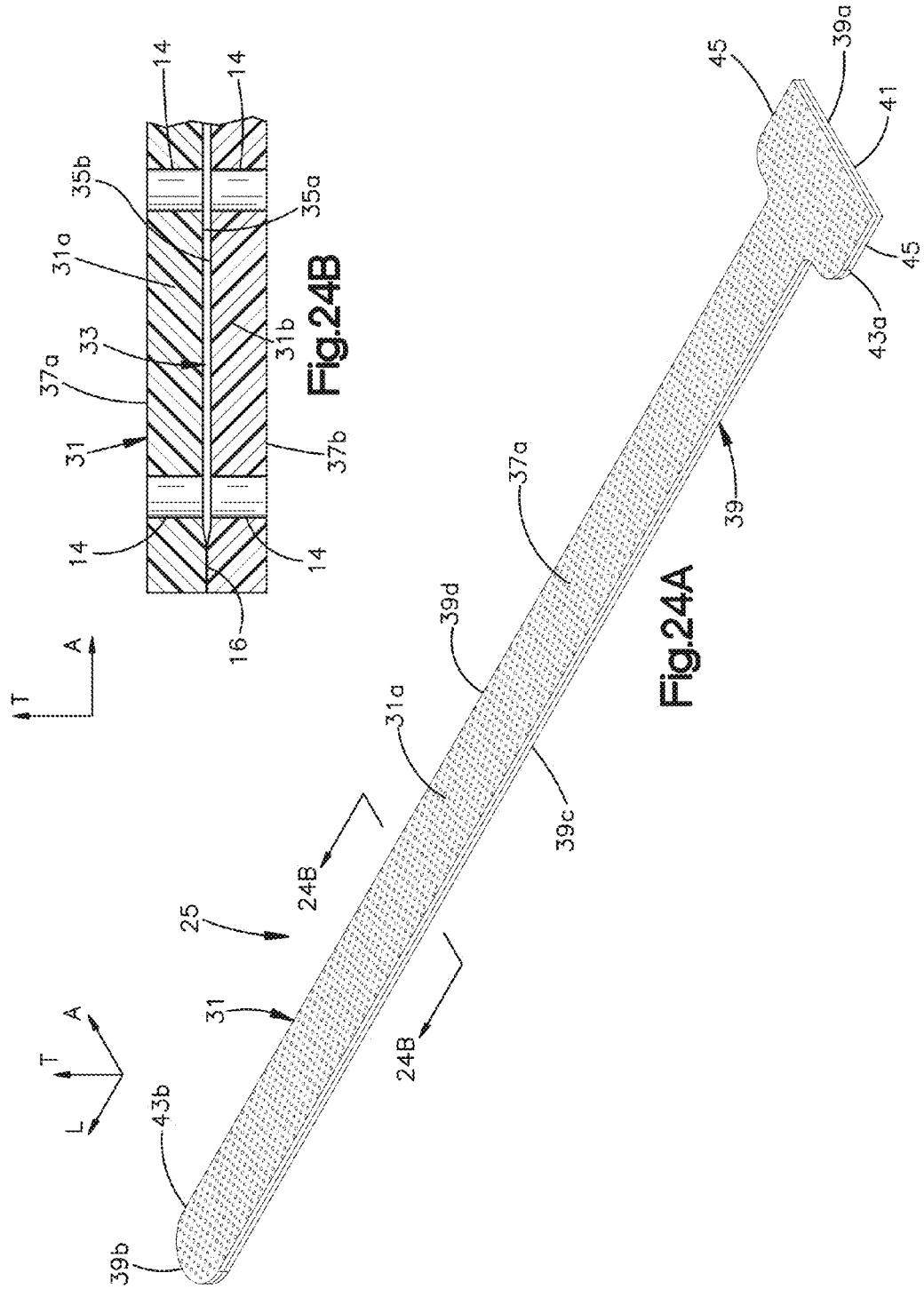

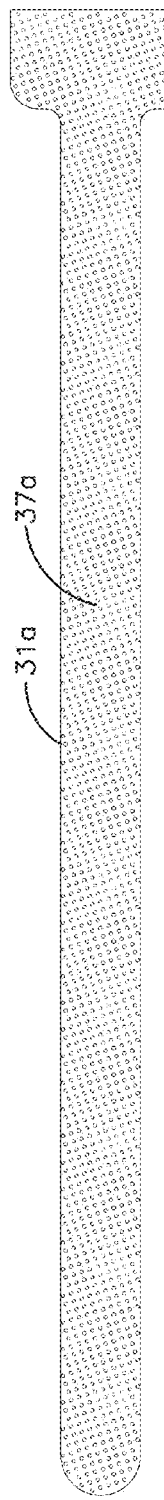
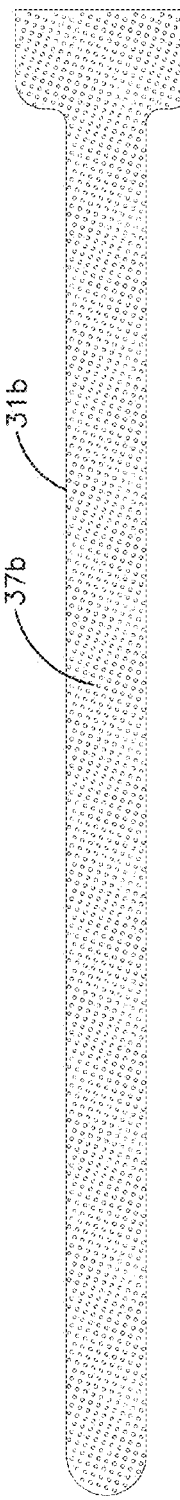
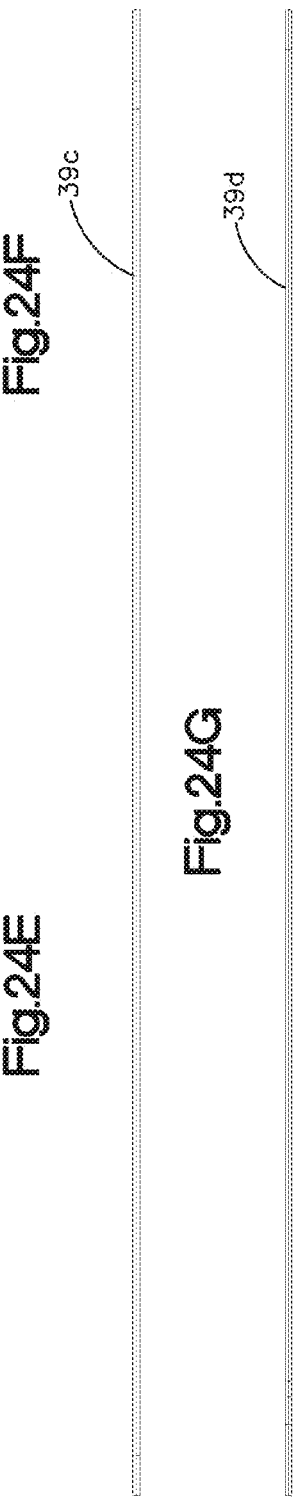
Fig.24C, Fig.24D, Fig.24E, Fig.24F, Fig.24G, Fig.24H

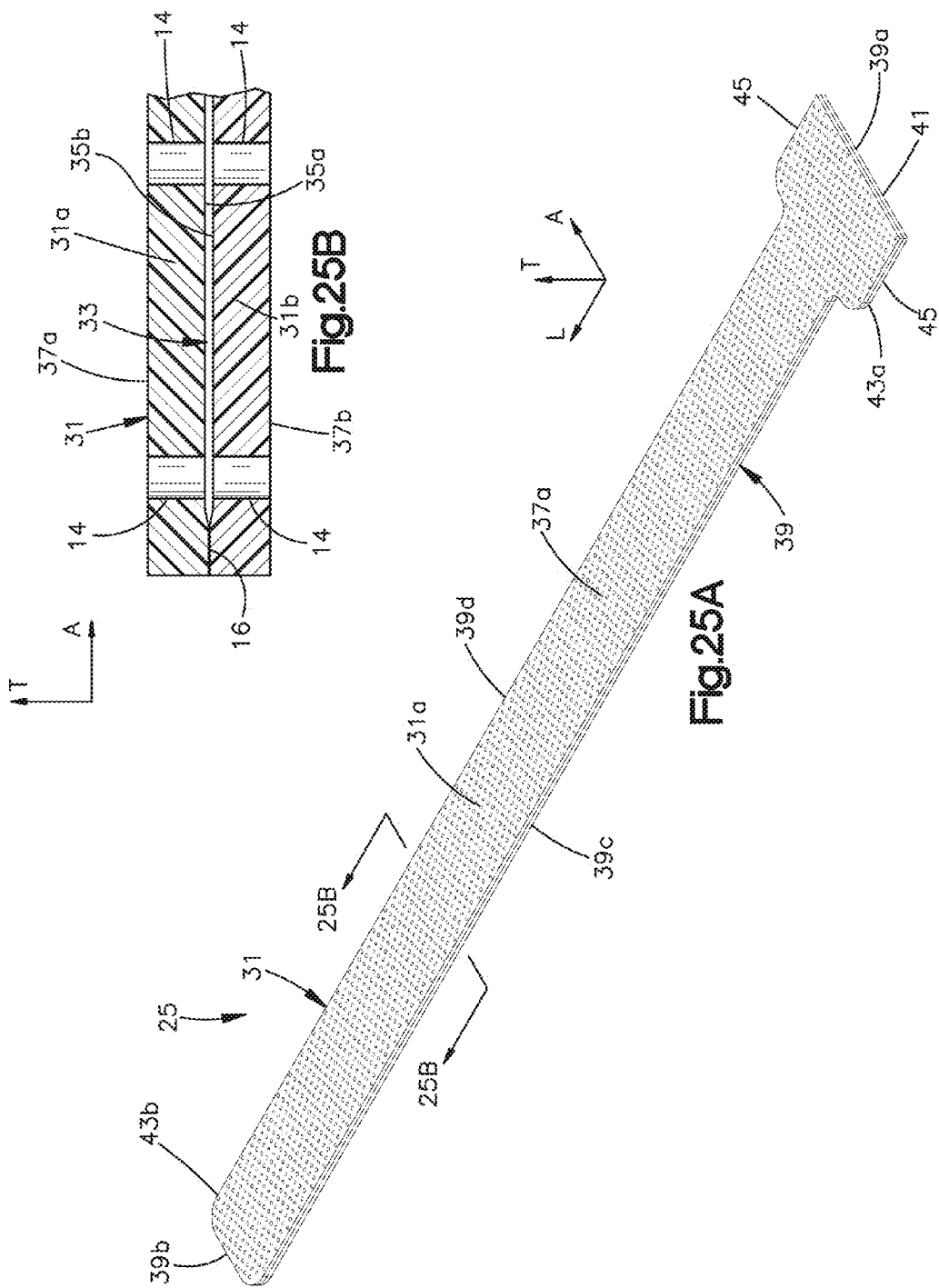

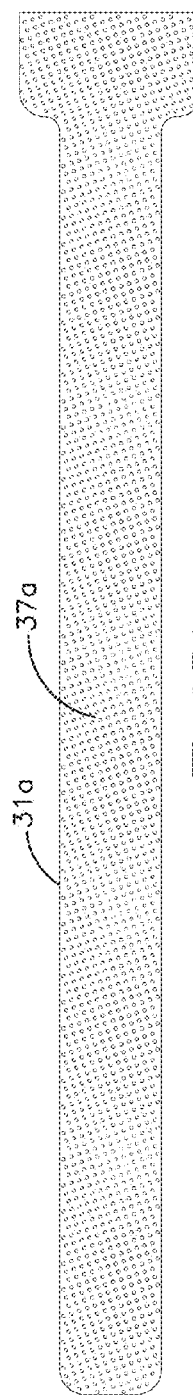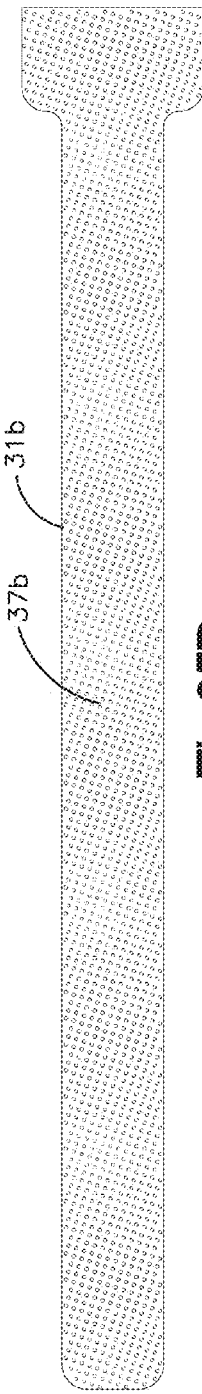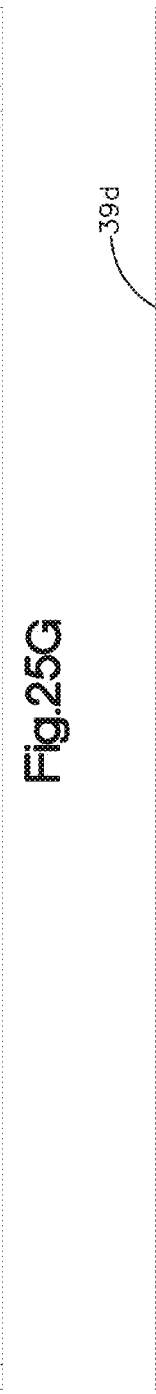

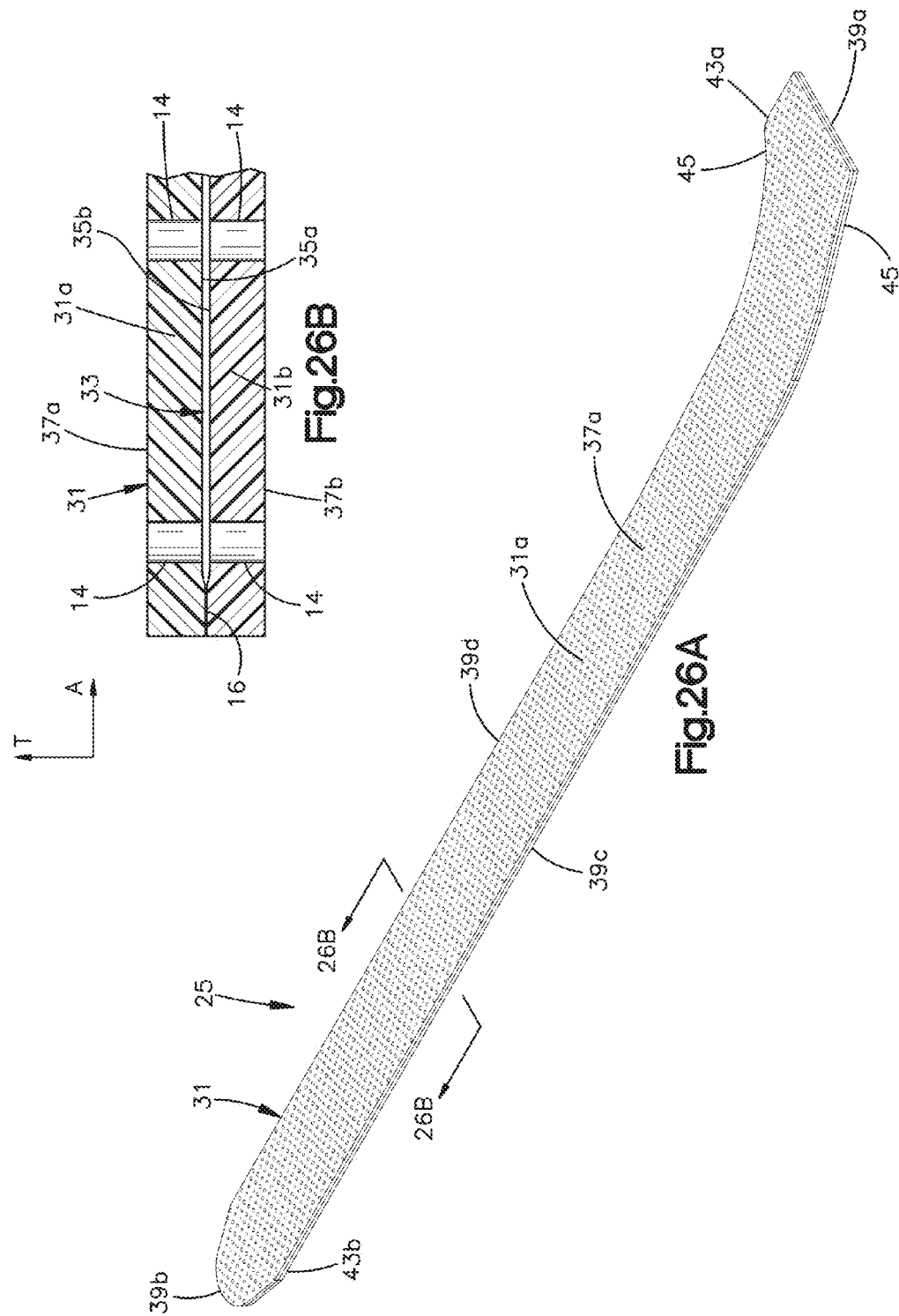

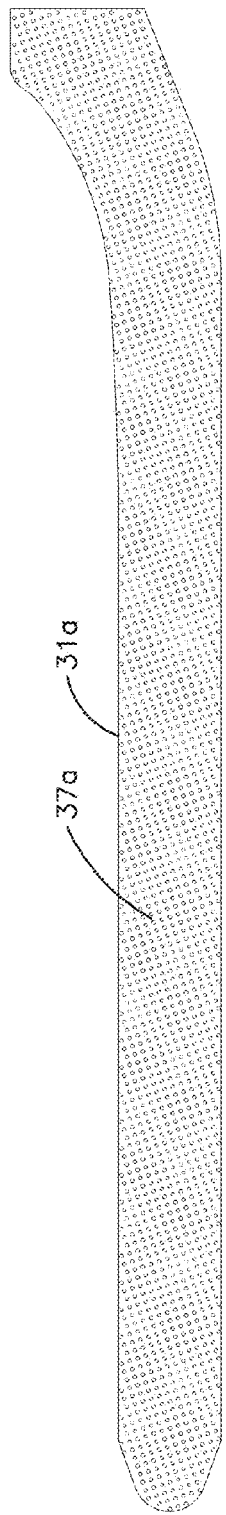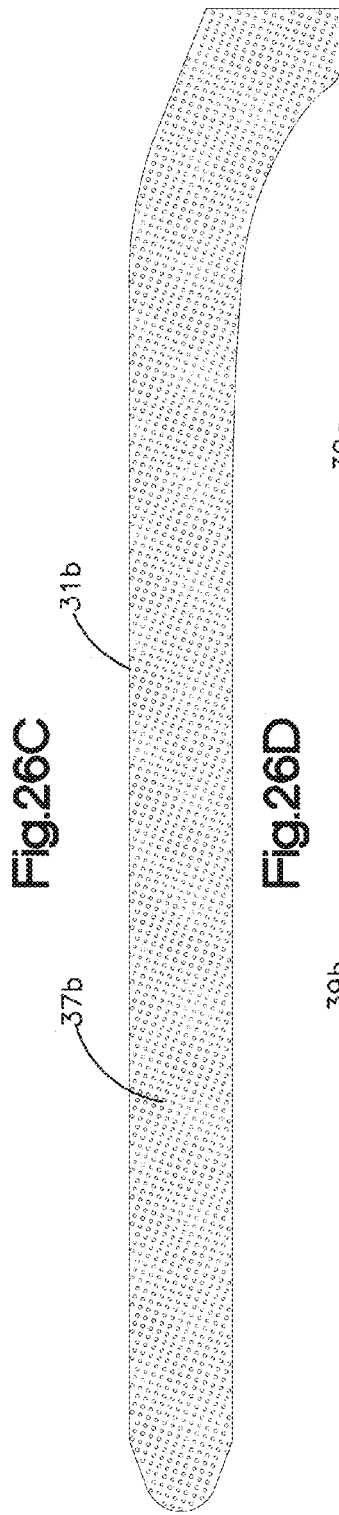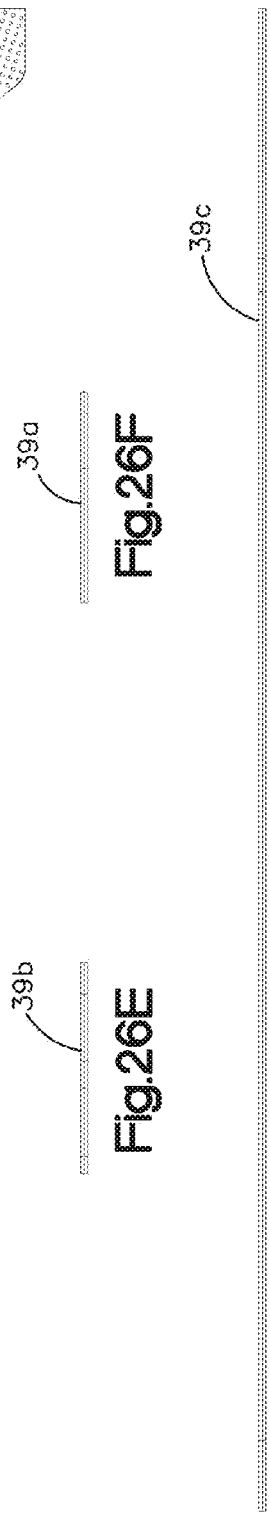
Fig.26C  Fig.26D  Fig.26E  Fig.26F  Fig.26G  Fig.26H

FILMS AND METHODS OF MANUFACTURE

CROSS-REFERENCE TO RELATED APPLICATIONS

This application is a divisional application of co-pending U.S. application Ser. No. 14/899,570, filed on Dec. 18, 2015, which is a National Stage Application filed under 35 U.S.C. 371 of International Application No. PCT/US2014/041662, filed Jun. 10, 2014, which claims the benefit of U.S. Provisional Patent Application No. 61/837,716, filed Jun. 21, 2013, all of which are hereby incorporated by reference in their entirety.

INCORPORATIONS BY REFERENCE

U.S. patent application Ser. No. 12/089,574, filed on Apr. 8, 2008, is a national stage application of PCT/US2006/040038, filed Oct. 12, 2006, and both applications are hereby incorporated by reference in their entirety. U.S. patent application Ser. No. 13/727,682, filed on Dec. 27, 2012, claims the benefit of U.S. Provisional Patent Application No. 61/580,679 filed Dec. 28, 2011 entitled "Films and Methods of Manufacture," and both applications are hereby incorporated by reference in their entirety.

FIELD OF THE DISCLOSURE

The present disclosure generally relates to films (e.g., polymer films) and methods of manufacture, and in at least some embodiments, perforated films and methods of medical use.

BACKGROUND

High-energy lower extremity fractures have been associated with surgical site infection (SSI) and osteomyelitis rates ranging from approximately 14% to 60% in both military and civilian settings. The current standard for treatment of such fractures typically includes using metal implants (plates and screws or nails) for fracture fixation, which have the potential disadvantage of placing metal within a fracture site. These metal implants can serve as sites for bacterial adhesion and formation of a bacterial biofilm, where bacteria can remain sequestered from the body's immune system, resulting in surgical site infections.

Although the use of intravenous (IV) antibiotics as a prophylaxis against wound infection has become standard, infection rates in certain types of orthopedic trauma remain high. Systemic antibiotics may not reach the implant surface in sufficient concentration due to locally impaired circulation at the wound site, and bacterial biofilm formation can be very rapid. Biofilm based infections are not only resistant to systemic antibiotic therapy and the host immune system, they typically require additional surgery to remove the infected implant.

Locally delivered antibiotics hold promise for reducing SSIs, particularly those associated with high-energy fractures, as they can be used to deliver high concentrations of antibiotics where needed and prevent the development of biofilms on the implant surface. Multiple studies in animals have demonstrated that if an implant surface can be protected from colonization by bacteria for a period of time immediately after surgery, the rate of subsequent infection can be significantly reduced.

Surgeons have used a variety of products for local delivery of antibiotics, typically aminoglycosides and/or vancomycin, including polymethyl methacrylate (PMMA) cements, beads, gels, and collagen sponges. However, in certain situations, these antibiotic treatments are not practical, for example where they take up space at the site making wound closure difficult, and in other situations may also require a separate surgery for their removal.

Infections represent a major challenge in orthopedic or trauma surgery. Despite prophylactic measures like asepsis and antisepsis, the surgery site is still a site of access for local pathogens to become virulent and cause infections.

Coating an implantable device with a drug, such as an antibiotic, has been effective to reduce infection. However, given the large number, sizes, and shapes of implants and other medical devices, the regulatory, financial, and logistical burden of providing a coating for each device is enormous. The problem is amplified if one considers additional drugs to use in coatings such as analgesics, antineoplastic agents and growth promoting substances.

SUMMARY

Embodiments of the present disclosure are directed to polymer films, and in some embodiments, perforated polymer films and novel casting methods of making the same. In some embodiments, the films are for use with implantable medical devices though the films may be used in any application.

Commercial methods of forming a perforated film currently existing generally involve forming a solid film as a first step, then punching or cutting holes into the film as a second step. An advantage of at least some of the embodiments described herein is that the holes or apertures of the film are formed at the same time that the film is formed. This may be useful when the polymer film to be formed is very thin and at risk for damage due to subsequent handling or processing or when the thickness and/or strength of the film makes it difficult to punch or cut by traditional methods without damaging the film. Such a process may also be advantageous when the polymer solution contains an active agent that may be damaged by subsequent hole-punching steps. The active agent may be a drug, such as an antimicrobial agent, including one or more of an anti-bacterial agent, an anti-viral agent, and anti-parasitic agent of the type known to one having ordinary skill in the art, or any suitable alternative active agent, such as an anti-inflammatory, a steroid, an analgesic, an opioid, a growth factor, or the like, Embodiments of the present disclosure may also be useful for making quantities of cast film such as those which are considered too small to make economically by traditional methods which are typically continuous processes designed for high volume production. An additional advantage of at least some embodiments of the present disclosure is that apertures (or perforations) formed in the cast sheet can have complex shapes. A further advantage of certain embodiments of the disclosure is that at least one side of the film may be formed to have a non-planar surface which in some embodiments increases (or reduces) friction and gives an improved tactile feel. These advantages of the present disclosure, as well as others, are described in further detail below.

In one embodiment there is a flexible body comprising a film (e.g., a polymer film) having a first surface and an opposing second surface, the film having a plurality of apertures extending from the first surface to the second surface and a plurality of raised lips protruding from the first surface such that each of the plurality of apertures is surrounded by a one of the plurality of raised lips. In a preferred embodiment, the film is comprised of a polymeric material (i.e., a polymer film). In one embodiment, the film comprises a single layer, and in another embodiment, the film can comprise a plurality of layers, for example, two or more layers, such as two layers, three layers, four layers, up to and including seven layers. In certain embodiments, the film can comprise an adhesive layer, for example, the first surface or the second surface of the film, or both, can comprise an adhesive layer. In another embodiment, one or more of the layers may be a drug containing layer and/or a rate controlling layer for drug release (with or without a drug contained therein).

In one embodiment, the polymer material comprises a bioresorbable polymer. In one embodiment, the bioresorbable polymer comprises a polyester or blend of polyesters (collectively "polyesters") and their co-polymers and derivatives. In certain preferred embodiments the polyester(s) is hydrolyzable. Suitable polyesters can include, for example, polyglycolic acid, polylactic acid and polycaprolactone. In one embodiment, the bioresorbable polymer is a copolymer of glycolide, trimethylene carbonate, lactide and caprolactone.

In one embodiment, the first surface includes a contiguous planar portion extending between the plurality of raised protruding lips. In one embodiment, the plurality of raised protruding lips each have an outer edge that is raised above the contiguous planar portion by approximately 0.1 mm to approximately 1.0 mm. In one embodiment, the polymer film comprises a plurality of discrete eluting drug components and wherein the polymer film is configured to elute the plurality of discrete drug components at different time periods following implantation of the flexible body. In a further embodiment, the flexible body comprises at least one attachment configured to form the polymer film into a sleeve. In one embodiment, the polymer film has a first tensile strength in a first planar direction and a second tensile strength in a second planar direction that is perpendicular to the first planar direction, wherein the first tensile strength is substantially equal to the second tensile strength. In one embodiment, the polymer film has a nominal thickness of no greater than 0.06 mm. In one embodiment, the first surface has a first tactile feel that is different from a second tactile feel of the second surface.

In another embodiment there is a method of producing a polymer film comprising: placing a polymer solution into a one sided mold having a plurality of protrusions extending from a bottom of the mold. In certain embodiments, the polymer solution is characterized by a viscosity that inhibits the unaided flow of the polymer throughout the mold. The process further includes urging the polymer solution around each of the plurality of protrusions; and solidifying the polymer solution. In one embodiment, the mold includes a perimeter form extending to an elevation that is substantially equal to an elevation of each of the plurality of protrusions. In one embodiment, the urging comprises drawing an urging instrument such as a blade, bar, squeegee or roller across the perimeter form and the plurality of protrusions to force the polymer solution to flow around the plurality of protrusions and throughout the mold such that the polymer solution has a substantially uniform thickness. In one embodiment, at least a portion of an outer surface of a protrusion, for example an upper portion of a protrusion, is substantially free of polymer solution after the drawing. In one embodiment, the placing step includes depositing the polymer solution in the mold such that a portion of the polymer solution is above the elevation of the perimeter form and the protrusions. In a still further embodiment, one or more of the method steps can be repeated such that a film comprising a plurality of layers may be produced, for example, two or more layers, such as two layers, three layers, four layers, up to and including seven layers. In certain embodiments, the method additionally includes the steps of placing one or more additional polymer solutions in the mold over a first polymer solution, and urging the one or more polymer solutions around each of the plurality of protrusions. These steps can occur prior to, during, or after the step of solidifying the polymer solution. Thus, according to one embodiment of the method, each of the one or more polymer solutions placed in the mold can solidify prior to, during, or after, the step of placing the next or subsequent additional polymer solution into the mold. According to one embodiment, the one or more polymer solutions comprises a polymer solution that can solidify into an adhesive layer, and according to another embodiment, the one or more polymer solutions comprises a rate controlling layer for drug release.

In one embodiment, solidifying the polymer solution includes reducing a thickness of the polymer solution. In one embodiment, solidifying the polymer solution includes forming a meniscus of solidified polymer around each of the plurality of protrusions. In one embodiment, distance from the bottom of the mold to a top of each of the plurality of protrusions is less than approximately 0.3 mm. In one embodiment, the polymer solution contains a drug. In one embodiment, the polymer solution is formed by combining a solvent, a polymer, and the drug at a temperature below 90° C. In one embodiment, the perimeter form defines a total mold area and the plurality of protrusions defines an area that is at least about 15% of the total mold area. In a further embodiment, the method comprises peeling, or otherwise removing, the drug eluting film from the mold.

In one embodiment, the polymer solution comprises a cross-linkable pre-polymer solution. In one embodiment, the solidifying step includes cross-linking the polymer by applying UV radiation, temperature change, polymerization catalysts, soluble crosslinking agents or combinations thereof to the polymer solution. In one embodiment, the polymer solution includes discrete drug units. In one embodiment, the polymer solution comprises a first solvent and a polymer and the solidifying step includes exposing the polymer solution to a second solvent in which the first solvent is soluble and in which the polymer and the drug are not soluble such that the first solvent is at least substantially removed from the polymer solution and the polymer solidifies to contain the drug.

The polymer films disclosed herein may be used to inhibit microbial infection at a surgical site, including bacterial colonization of a medical implant implanted at the surgical site. Typically, the methods comprise identifying a surgical site in need of microbial inhibition and contacting the surgical site with a polymer film comprising an active agent (e.g., drug). The methods may also involve identifying a zone at a surgical site or on a medical implant needing microbial inhibition, contacting the medical implant with the polymer film, e.g., by affixing the polymer film to the implant, and implanting the medical implant at the surgical site. Because the contacting of the polymer film and the medical implant are done at or near the time of surgery, i.e., intraoperatively, the surgeon can match the polymer film with the medical implant to be contacted based on the size and shape of the medical implant and the drug requirements for the subject patient.

BRIEF DESCRIPTION OF THE DRAWINGS

The foregoing summary, as well as the following detailed description of embodiments of the polymer films and methods of manufacture, will be better understood when read in conjunction with the appended drawings of exemplary embodiments. It should be understood, however, that the invention is not limited to the precise arrangements and instrumentalities shown.

In the drawings:

FIG. 5 is a perspective view of an automated casting apparatus in accordance with an exemplary embodiment of the present disclosure;

FIG. 11A is a top plan view of a sleeve that comprises at least one polymer film of the type illustrated in FIG. 1 shown in one configuration;

FIG. 11B is a top plan view of a sleeve that comprises at least one polymer film of the type illustrated in FIG. 1 shown in another configuration;

FIG. 11C is a top plan view of a sleeve that comprises at least one polymer film of the type illustrated in FIG. 1, shown in another configuration;

FIG. 11G is a top plan view of a sleeve that comprises at least one polymer film of the type illustrated in FIG. 1, shown in another configuration;

FIG. 11H is a top plan view of a sleeve that comprises at least one polymer film of the type illustrated in FIG. 1, shown in another configuration;

FIG. 11I is a top plan view of a sleeve that comprises at least one polymer film of the type illustrated in FIG. 1, shown in another configuration;

FIG. 11J is a top plan view of a sleeve that comprises at least one polymer film of the type illustrated in FIG. 1, shown in another configuration;

FIG. 11K is an enlarged perspective view of a portion of the film of each of the sleeves as illustrated in FIGS. 11A-J in accordance with one embodiment;

FIG. 17A is a top, front, right perspective view of the sleeve illustrated in FIG. 11A, including a pair of films shown in a closed configuration;

FIG. 17B is a sectional elevation view of a portion of the sleeve illustrated in FIG. 17A taken at line 17B-17B of FIG. 17A, showing the sleeve in an open configuration whereby the films are partially separated from each other;

FIG. 17C is a top plan view of the sleeve illustrated in FIG. 17A;

FIG. 17D is a bottom plan view of the sleeve illustrated in FIG. 17A;

FIG. 17E is a rear elevation view of the sleeve illustrated in FIG. 17A;

FIG. 17F is a front elevation view of the sleeve illustrated in FIG. 17A;

FIG. 17G is a right side elevation view of the sleeve illustrated in FIG. 17A;

FIG. 17H is a left side elevation view of the sleeve illustrated in FIG. 17A;

FIG. 18A is a top, front, right perspective view of the sleeve illustrated in FIG. 11B, including a pair of films shown in a closed configuration;

FIG. 18B is a sectional elevation view of a portion of the sleeve illustrated in FIG. 18A taken at line 18B-18B of FIG. 18A, showing the sleeve in an open configuration whereby the films are partially separated from each other;

FIG. 18C is a top plan view of the sleeve illustrated in FIG. 18A;

FIG. 18D is a bottom plan view of the sleeve illustrated in FIG. 18A;

FIG. 18E is a rear elevation view of the sleeve illustrated in FIG. 18A;

FIG. 18F is a front elevation view of the sleeve illustrated in FIG. 18A;

FIG. 18G is a right side elevation view of the sleeve illustrated in FIG. 18A;

FIG. 18H is a left side elevation view of the sleeve illustrated in FIG. 18A;

FIG. 19A is a top, front, right perspective view of the sleeve illustrated in FIG. 11C, including a pair of films shown in a closed configuration;

FIG. 19B is a sectional elevation view of a portion of the sleeve illustrated in FIG. 19A taken at line 19B-19B of FIG. 19A, showing the sleeve in an open configuration whereby the films are partially separated from each other;

FIG. 19C is a top plan view of the sleeve illustrated in FIG. 19A;

FIG. 19D is a bottom plan view of the sleeve illustrated in FIG. 19A;

FIG. 19E is a rear elevation view of the sleeve illustrated in FIG. 19A;

FIG. 19F is a front elevation view of the sleeve illustrated in FIG. 19A;

FIG. 19G is a right side elevation view of the sleeve illustrated in FIG. 19A;

FIG. 19H is a left side elevation view of the sleeve illustrated in FIG. 19A;

FIG. 20A is a top, front, right perspective view of the sleeve illustrated in FIG. 11D, including a pair of films shown in a closed configuration;

FIG. 20B is a sectional elevation view of a portion of the sleeve illustrated in FIG. 20A taken at line 20B-20B of FIG. 20A, showing the sleeve in an open configuration whereby the films are partially separated from each other;

FIG. 20C is a top plan view of the sleeve illustrated in FIG. 20A;

FIG. 20D is a bottom plan view of the sleeve illustrated in FIG. 20A;

FIG. 20E is a rear elevation view of the sleeve illustrated in FIG. 20A;

FIG. 20F is a front elevation view of the sleeve illustrated in FIG. 20A;

FIG. 20G is a right side elevation view of the sleeve illustrated in FIG. 20A;

FIG. 20H is a left side elevation view of the sleeve illustrated in FIG. 20A;

FIG. 21A is a top, front, right perspective view of the sleeve illustrated in FIG. 11E, including a pair of films shown in a closed configuration;

FIG. 21B is a sectional elevation view of a portion of the sleeve illustrated in FIG. 21A taken at line 21B-21B of FIG. 21A, showing the sleeve in an open configuration whereby the films are partially separated from each other;

FIG. 22A is a top, front, right perspective view of the sleeve illustrated in FIG. 11F, including a pair of films shown in a closed configuration;

FIG. 22B is a sectional elevation view of a portion of the sleeve illustrated in FIG. 22A taken at line 22B-22B of FIG. 22A, showing the sleeve in an open configuration whereby the films are partially separated from each other;

FIG. 22C is a top plan view of the sleeve illustrated in FIG. 22A;

FIG. 22D is a bottom plan view of the sleeve illustrated in FIG. 22A;

FIG. 22E is a rear elevation view of the sleeve illustrated in FIG. 22A;

FIG. 22F is a front elevation view of the sleeve illustrated in FIG. 22A;

FIG. 22G is a right side elevation view of the sleeve illustrated in FIG. 22A;

FIG. 22H is a left side elevation view of the sleeve illustrated in FIG. 22A;

FIG. 23A is a top, front, right perspective view of the sleeve illustrated in FIG. 11G, including a pair of films shown in a closed configuration;

FIG. 23B is a sectional elevation view of a portion of the sleeve illustrated in FIG. 23A taken at line 23B-23B of FIG. 23A, showing the sleeve in an open configuration whereby the films are partially separated from each other;

FIG. 23C is a top plan view of the sleeve illustrated in FIG. 23A;

FIG. 23D is a bottom plan view of the sleeve illustrated in FIG. 23A;

FIG. 23E is a rear elevation view of the sleeve illustrated in FIG. 23A;

FIG. 23F is a front elevation view of the sleeve illustrated in FIG. 23A;

FIG. 23G is a right side elevation view of the sleeve illustrated in FIG. 23A;

FIG. 23H is a left side elevation view of the sleeve illustrated in FIG. 23A;

FIG. 24A is a top, front, right perspective view of a portion of the sleeve illustrated in FIG. 11H, including a pair of films shown in a closed configuration;

FIG. 24B is a sectional elevation view of the sleeve illustrated in FIG. 23A taken at line 24B-24B of FIG. 24A, showing the sleeve in an open configuration whereby the films are partially separated from each other;

FIG. 24C is a top plan view of the sleeve illustrated in FIG. 24A;

FIG. 24D is a bottom plan view of the sleeve illustrated in FIG. 24A;

FIG. 24E is a rear elevation view of the sleeve illustrated in FIG. 24A;

FIG. 24F is a front elevation view of the sleeve illustrated in FIG. 24A;

FIG. 24G is a right side elevation view of the sleeve illustrated in FIG. 24A;

FIG. 24H is a left side elevation view of the sleeve illustrated in FIG. 24A;

FIG. 25A is a top, front, right perspective view of the sleeve illustrated in FIG. 11I, including a pair of films shown in a closed configuration;

FIG. 25B is a sectional elevation view of a portion of the sleeve illustrated in FIG. 25A taken at line 25B-25B of FIG. 25A, showing the sleeve in an open configuration whereby the films are partially separated from each other;

FIG. 25C is a top plan view of the sleeve illustrated in FIG. 25A;

FIG. 25D is a bottom plan view of the sleeve illustrated in FIG. 25A;

FIG. 25E is a rear elevation view of the sleeve illustrated in FIG. 25A;

FIG. 25F is a front elevation view of the sleeve illustrated in FIG. 25A;

FIG. 25G is a right side elevation view of the sleeve illustrated in FIG. 25A;

FIG. 25H is a left side elevation view of the sleeve illustrated in FIG. 25A;

FIG. 26A is a top, front, right perspective view of the sleeve illustrated in FIG. 11J, including a pair of films shown in a closed configuration;

FIG. 26B is a sectional elevation view of a portion of the sleeve illustrated in FIG. 26A taken at line 26B-26B of FIG. 26A, showing the sleeve in an open configuration whereby the films are partially separated from each other;

FIG. 26C is a top plan view of the sleeve illustrated in FIG. 26A;

FIG. 26D is a bottom plan view of the sleeve illustrated in FIG. 26A;

FIG. 26E is a rear elevation view of the sleeve illustrated in FIG. 26A;

FIG. 26F is a front elevation view of the sleeve illustrated in FIG. 26A;

FIG. 26G is a right side elevation view of the sleeve illustrated in FIG. 26A; and FIG. 26H is a left side elevation view of the sleeve illustrated in FIG. 26A;

FIG. 27 is graph showing a log reduction in CFUs for a variety of bacteria in the presence of a drug-containing polymer film according to one embodiment of the present disclosure;

FIG. 28 is a graph showing a minimum effective concentration and zone of inhibition in the presence of drug-containing polymer films according to embodiments of the present disclosure; and;

FIG. 29 is a graph showing a zone of inhibition against several bacteria in the presence of a drug-containing polymer film according to an embodiment of the present disclosure.

DETAILED DESCRIPTION OF ILLUSTRATIVE EMBODIMENTS

Figure 1A:
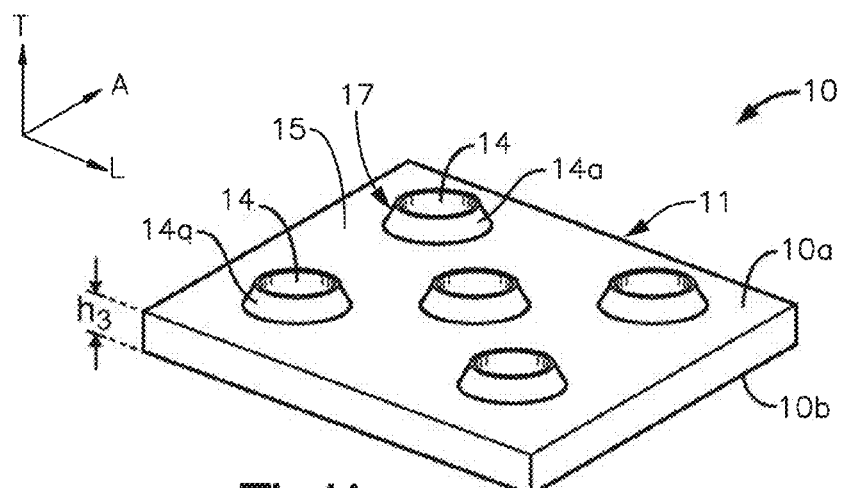
FIG. 1A is an enlarged perspective schematic view of a portion of a film (in this instance a polymer film) in accordance with an exemplary embodiment of the present disclosure.
Figure 3A:
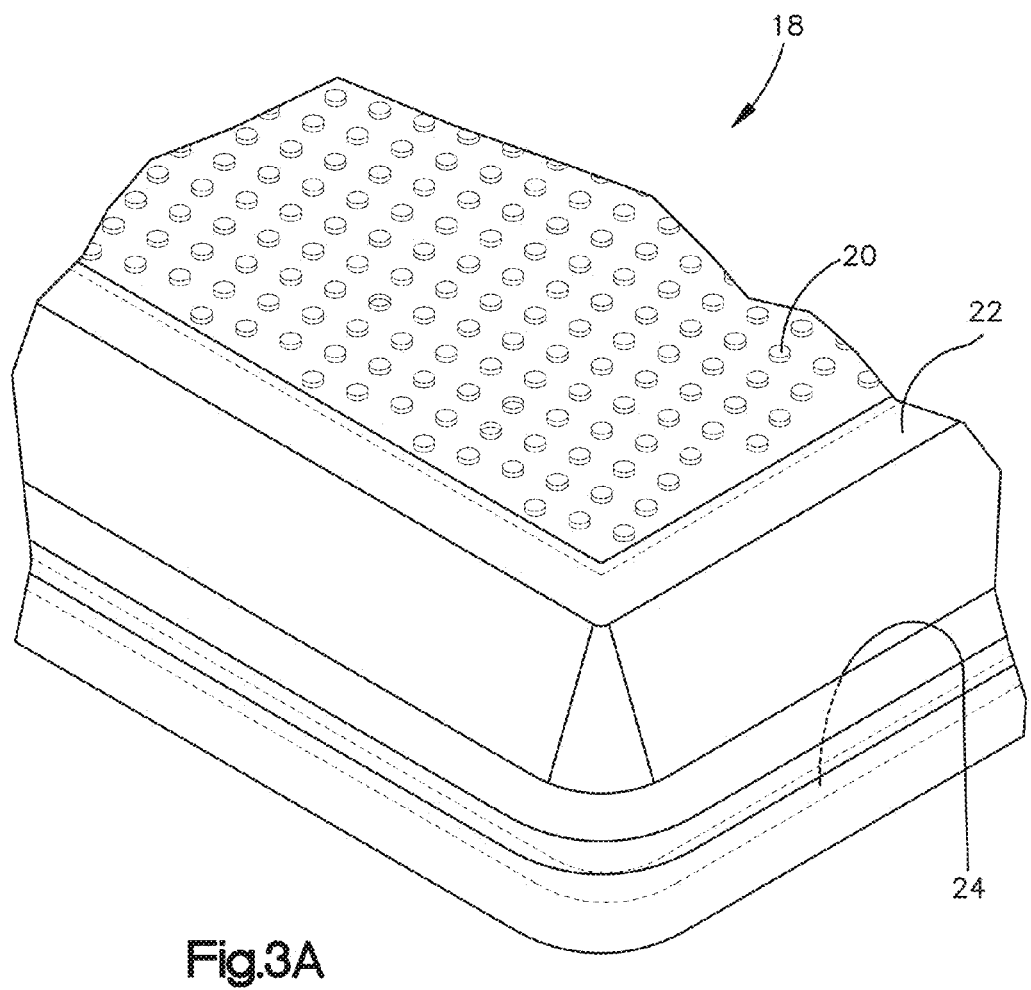
FIG. 3A is a perspective view of a portion of a mold in accordance with an exemplary embodiment of the present disclosure.
Figure 3B:
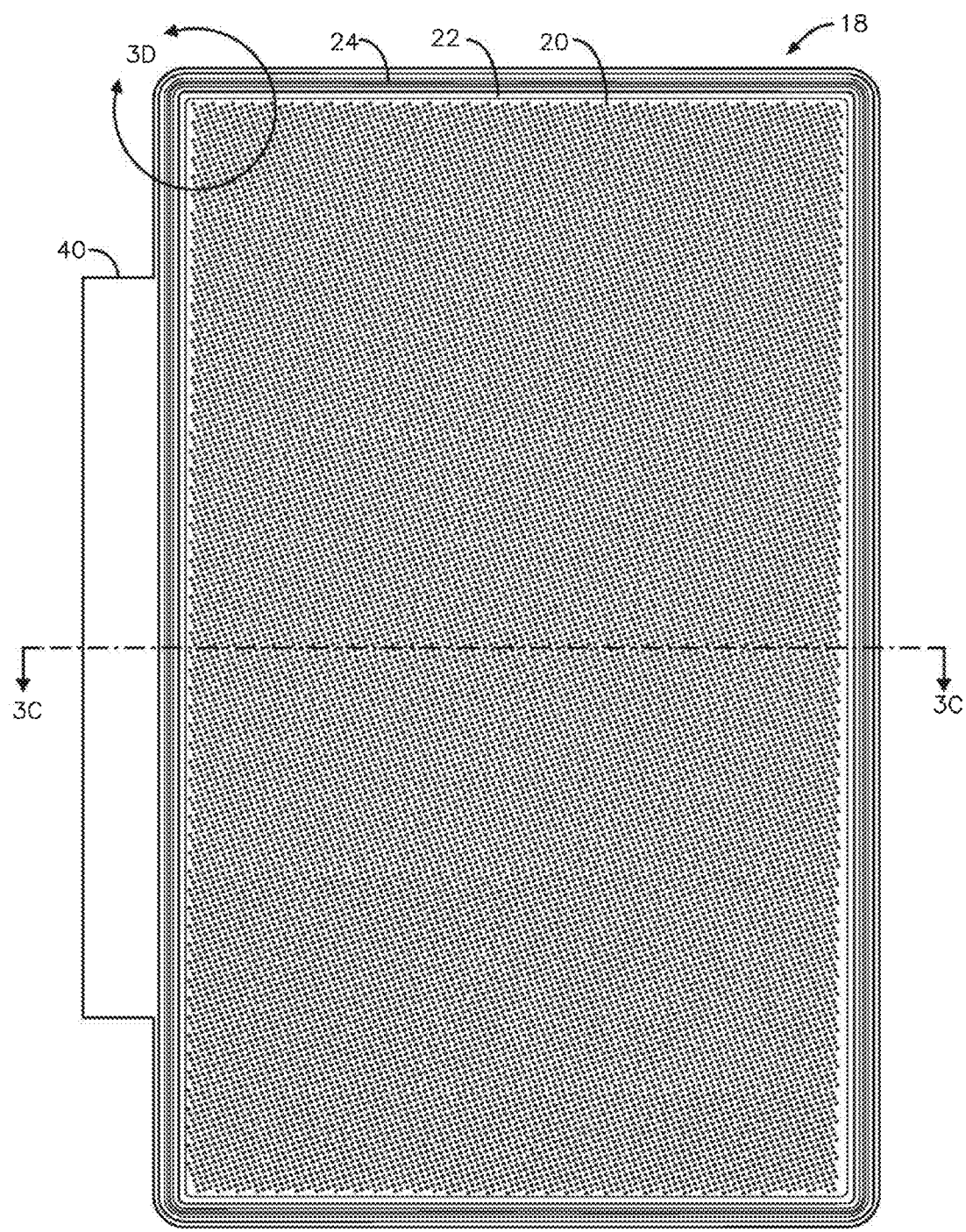
FIG. 3B is a top plan view of the mold of FIG. 3A.
Figure 3C:
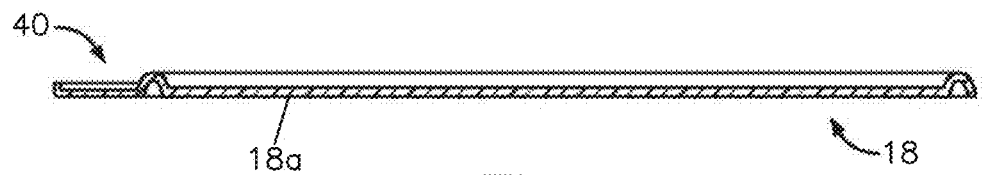
FIG. 3C is a cross-sectional side view of the mold of FIG. 3B taken about line C-C in FIG. 3B.
Figure 3D:
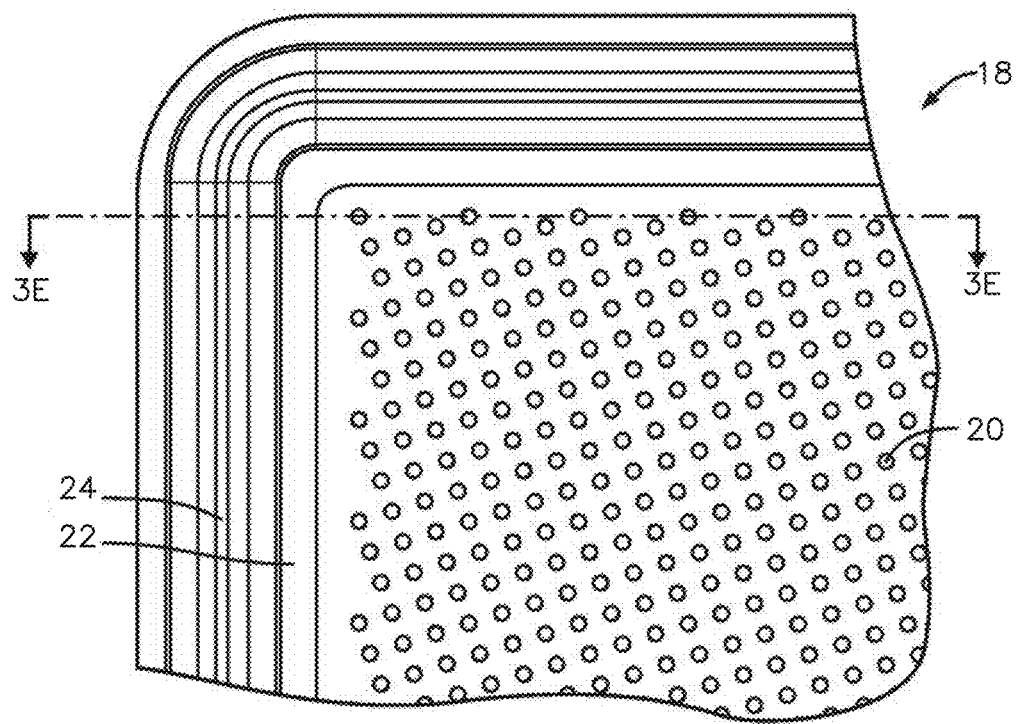
FIG. 3D is an enlarged corner section of the mold shown in FIG. 3B.
Figure 3E:
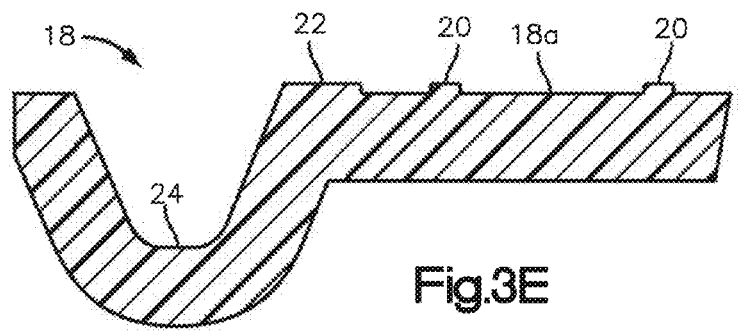
FIG. 3E is an enlarged cross section of the mold shown in FIG. 3D taken along line 3E-3E.
Figure 3F:
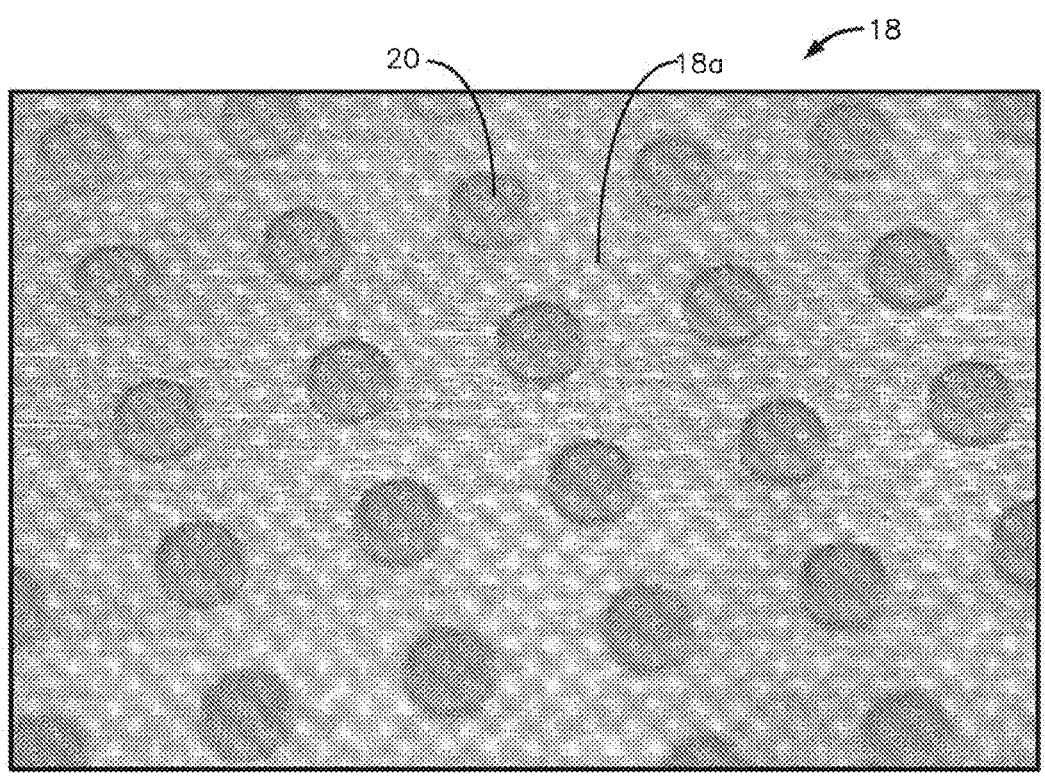
FIG. 3F is an enlarged perspective photograph of a section of the mold of FIG. 3A.
Figure 3G:
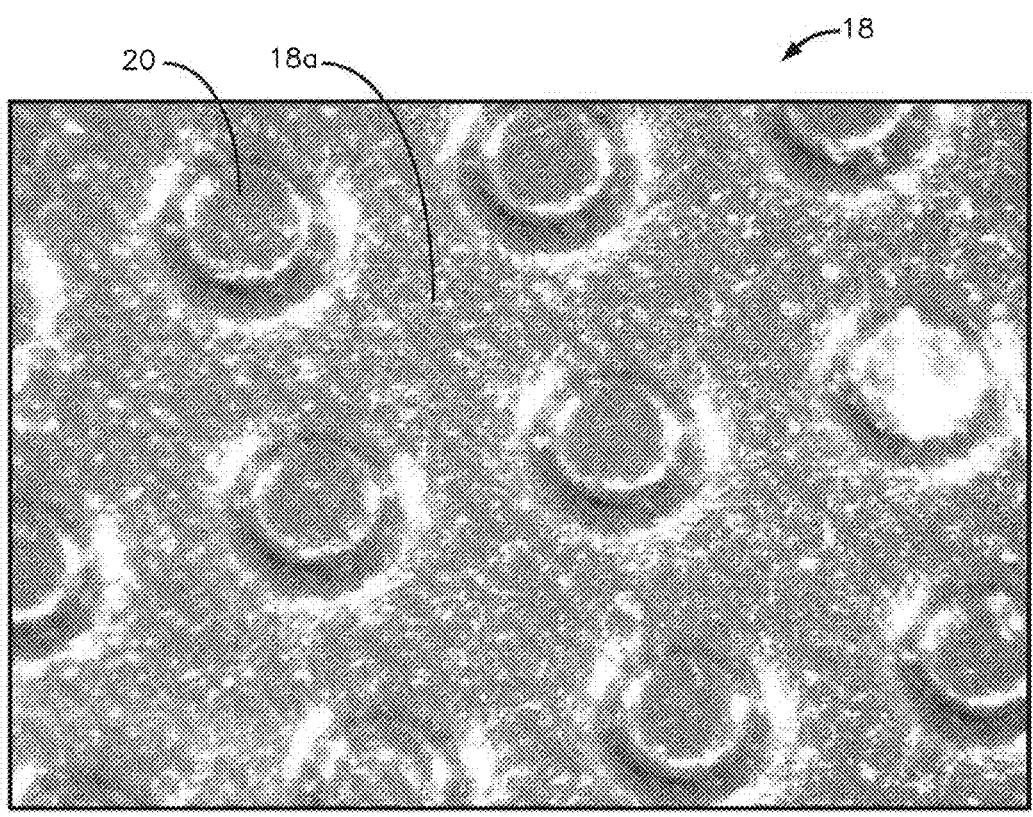
FIG. 3G is an enlarged perspective photograph of a section of the mold in accordance with another exemplary embodiment of the present disclosure.

Referring to the drawings in detail, wherein like reference numerals indicate like elements throughout, there is shown in FIGS. 1A and 3A polymer films, generally designated 10, and molds, generally designated 18, in accordance with exemplary embodiments of the present disclosure.

Figure 2:
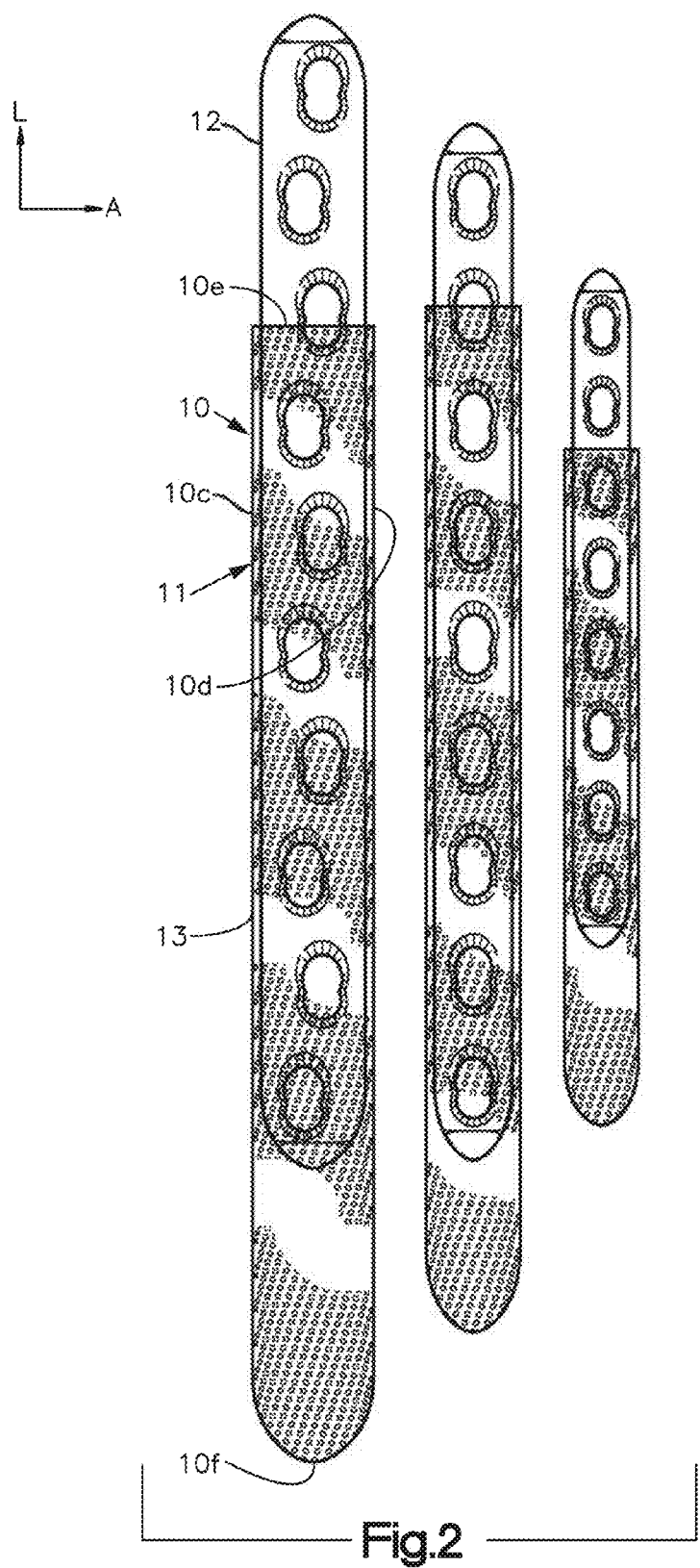
FIG. 2 is a top view of three exemplary sleeves formed from the polymer film of FIG. 1B in combination with a respective implantable medical device.

Referring to the embodiment of FIG. 1A, the film 10 (e.g., a polymer film) is a flexible body 11 having a first surface 10a and a second surface 10b that is opposite the first surface 10a along a transverse direction T. As also illustrated in FIG. 2, the flexible body 11, and thus the film 10, defines first and second opposed sides 10c and 10d that are spaced from each other along a lateral direction A that is perpendicular to the transverse direction T, and first and second opposed ends 10e and 10f that are spaced from each other along a longitudinal direction L that is perpendicular to both the transverse direction T and the lateral direction A. In accordance with one embodiment, the film 10 is elongate along the longitudinal direction L so as to define a length along the longitudinal direction L, defines a thickness along the transverse direction T, and defines a width along the lateral direction A. The sides 10c and 10d and the ends 10e and 10f can define edges, and in combination can define an outer periphery 13 of the film 10.

The film may define at least one layer of a biologically compatible material. such as a polymeric material. In one embodiment, the film 10 may be formed from a single thin layer of a biologically compatible material. In one embodiment, film 10 is comprised of two or more layers of biologically compatible material, such as two layers, three layers, four layers, up to and including seven layers. In certain embodiments, the film 10 can comprise an adhesive layer. For example, the first surface 10a or the second 10b surface of the film 10, or both the first surface 10a and the second surface 10b, can comprise an adhesive layer, such that the adhesive layer defines one or both of the first surface 10a and the second surface 10b. For instance, when the film 10 is formed from a single layer, the single layer of the film 10 can have adhesive properties, such that the layer of adhesive is defined by the single layer of the film 10 and one or both of the first and second surfaces can comprise an adhesive layer. Alternatively, when the film 10 comprises a plurality (e.g., at least two) layers, at least one of the two or more layers of film 10 can include a layer of adhesive that is applied to one or both of the first and second surfaces 10a and 10b of the film. In certain embodiments, one or more of the layers of the film 10 may be a drug containing layer and/or a rate controlling layer for drug release (with or without a drug contained therein). Unless otherwise indicated, reference herein to one or more layers of the film 10 includes both embodiments where the film 10 is formed of a single layer, and embodiments where the film comprises a plurality of layers.

In a preferred embodiment, the biologically-compatible material is a polymeric material and in a further preferred embodiment, the polymeric material is bioresorbable. In embodiments used with a medical device, such as a bone plate 12 (see FIG. 2), for instance where the film covers at least a portion of the bone plate 12, the film 10, in some embodiments, will dissolve away over time when implanted in vivo and be absorbed into a patient, leaving only the bone plate 12 behind (such as if bone plate 12 is not also made of a bioresorbable material). The bone plate 12 may also be made of a bioresorbable material in other embodiments in which case both the bone plate 12 and the film 10 will eventually dissolve. In some embodiments, the film 10 may be configured to absorb at a different rate from an absorbable bone plate 12 (e.g., a faster or a slower rate). It should be appreciated in certain embodiments that the first surface 10a of the film 10 can face the bone plate 12 and the second surface 10b can face away from the bone plate 12 during use, and in other embodiments the second surface 10b of the film 10 can face the bone plate 12 and the first surface 10a can face away from the bone plate 12 during use. While reference is made herein to a bone plate 12, it should be appreciated that the film 10 is configured for use in combination with any suitable medical implants as desired, such as any suitable orthopedic implant used in musculoskeletal repair, and that unless otherwise indicated herein, reference to a bone plate 12 applies with equal weight to other medical implants.

In some embodiments, a bioresorbable film 10 has advantages over non-resorbable meshes which, for example, can become encased with or embedded in dense fibrous tissue or present other issues associated with long term foreign body exposure. In some embodiments, the film 10 is only partially bioresorbable.

A bioresorbable polymer may be used in order to provide a controlled release of a drug such as an antibiotic, with a definite end point. Continuous, long term presence of an antibiotic is often undesirable, since this can create conditions for development of antibiotic resistant bacteria. In one embodiment, complete degradation of the film 10 ensures that the drug will be completely released in a pre-determined and/or selectable time. In one embodiment, the drug release can be completely released or substantially completely released even where the film 10 is not fully absorbed.

The absorption of the film 10 may also impact and/or control the release of the antibiotic in the continuous release phase. As the film 10 degrades, for example, the permeability of the film may increase, and more drugs may be released. In some embodiments, the polymer defines a film that is flexible, has a sufficiently high tensile strength, and can be processed by solution casting.

One particular class of preferred bioresorbable polymers are those containing aliphatic polyesters. Examples of such polyesters include polyglycolic acid (PGA), polylactic acid (PLA), polycaprolactone (PCL), polydioxanone, poly(trimethylene carbonate) (TMC), polyhydroxyalkanoates, and copolymers, derivatives, and blends of the same. Bioresorbable polymer materials can differ in their molecular weight, polydispersity, crystallinity, glass transition temperatures, and degradation rates, which can ultimately alter the mechanical properties of the film.

Particularly preferred bioresorbable polymers include co-polymer compositions containing PGA, PLA and PCL. According to one embodiment, film 10 is comprised of co-polymer having about 40% to about 95% glycolide content by weight; for example about 60% to about 75%, about 60% to about 70%, about 65% to about 75%, and about 68% to about 72%. According to another embodiment, film 10 is comprised of co-polymer having about less than 1% (including 0%) to about 50% caprolactone content by weight; for example about 5% percent to about 30%, about 10% to about 40%, about 10% to about 22%, about 14% to about 18%, and about 30% to about 40%. According to a further embodiment, film 10 is comprised of about less than 1% (including 0%) to about 15% lactide content by weight; for example less than about 1% to about 10%, less than about 1% to about 7.5%, about 3% to about 7.5%, about less than 1% to about 5%, and about 4% to about 7%.

In one embodiment, the film 10 is comprised of a co-polymer that includes one or more of four monomers; glycolide, lactide, caprolactone, and trimethylene carbonate. Glycolide may be included and may have the effect of speeding up degradation of the film 10. Lactide may also be included and may have the effect of increasing mechanical strength of film 10. Caprolactone and trimethylene carbonate may be used and may have the effect of increasing flexibility of film 10.

In one embodiment, the bioresorbable polymer includes one or more of PLA, PGA, PCL, polydioxanone, TMC and copolymers of these. In one embodiment, the bioresorbable polymer is produced from a copolymer of glycolic acid, caprolactone, lactic acid, and trimethylene carbonate. In one embodiment, the bioresorbable polymer is produced from a copolymer of approximately 60-70% glycolic acid, approximately 17-20% caprolactone, approximately 5-10% lactic acid and approximately 8-10% trimethylene carbonate. In one embodiment, the bioresorbable polymer contains repeat units selected from the group consisting of: L-lactic acid, D-lactic acid, L-lactide, D-lactide, D,L-lactide, glycolide, a lactone, a lactam, trimethylene carbonate, a cyclic carbonate, a cyclic ether, para-dioxanone, beta-hydroxybutyric acid, beta-hydroxypropionic acid, beta-hydroxyvaleric acid, and a combination thereof. In one embodiment, the bioresorbable polymer contains repeat units selected from the group consisting of: L-lactic acid, D-lactic acid, L-lactide; D-lactide, D,L-lactide, ε-caprolactone, trimethylene carbonate, para-dioxanone, and a combination thereof. Film 10 may also or alternatively include natural biopolymers such as alginate, chitosan, collagen, gelatin, hyaluronate, zein and others.

Figure 1B:
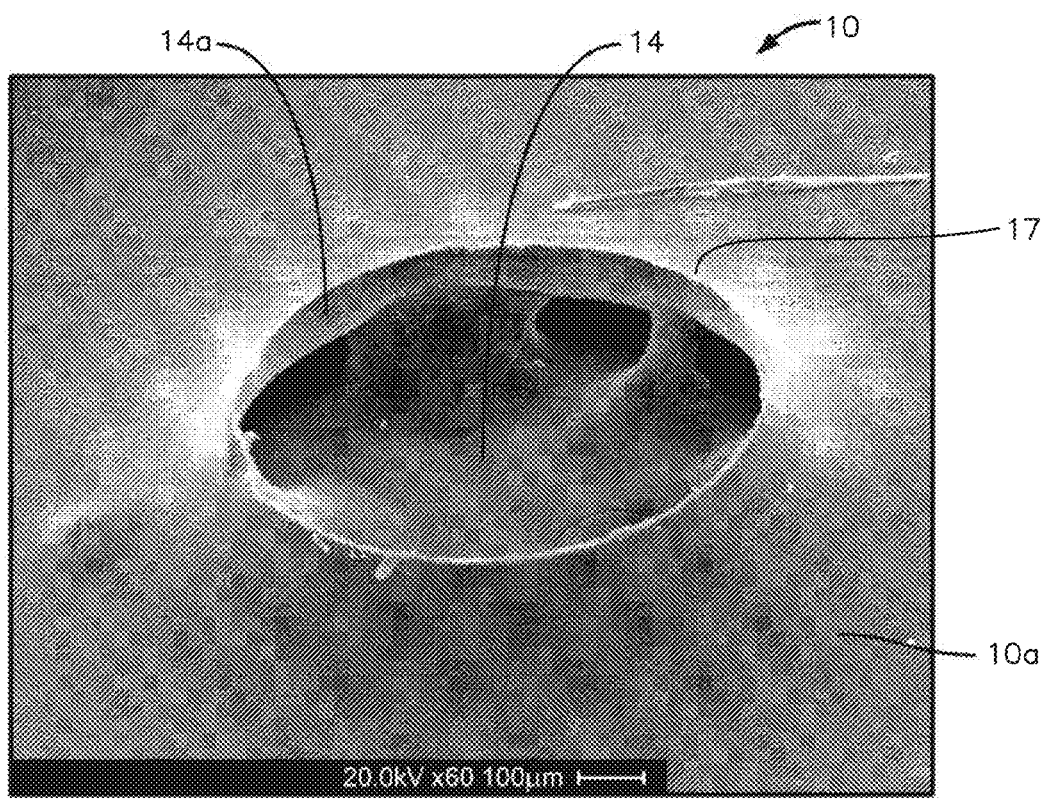
FIG. 1B is a 60× magnified photo of an aperture of a polymer film in accordance with an exemplary embodiment of the present disclosure.

Still referring to FIG. 1A, the film 10 may be configured to have any preferred dimensions including a thickness $h_3$ measured along the transverse direction T between first surface 10a and second surface 10b not inclusive of the raised lips 14a that are illustrated in FIGS. 1A and 1B as surrounding apertures 14. In one embodiment, film 10 is sufficiently thin such that it does not interfere with the mechanical interlocking between the bone plate 12 and the screws that are driven through the film 10 and the bone plate 12 and into an underlying bone during fixation (such as where if the film is trapped between the plate and screw). In some embodiments, thickness $h_3$ is minimized as much as possible. In one embodiment, the thickness of film 10 is selected such that degradation of film 10 does not cause significant loosening of a connection to bone plate 12 such as a plate-screw construct.

In some embodiments, the thickness $h_3$ of film 10 is approximately 0.05 mm. In some embodiments, the thickness $h_3$ of film 10 is approximately no greater than 0.05 mm. In some embodiments, thickness $h_3$ of film 10 is less than approximately 0.05 mm, for example approximately 0.04 mm. In some embodiments, thickness $h_3$ of film 10 is approximately 0.06 mm. In some embodiments, thickness $h_3$ of film 10 is approximately 0.07 mm. In some embodiments, thickness $h_3$ of film 10 is approximately 0.08 mm. In some embodiments, thickness $h_3$ of film 10 is approximately 0.09 mm. In some embodiments, thickness $h_3$ of film 10 is approximately 0.1 mm. In some embodiments, thickness $h_3$ of film 10 is approximately 0.2 mm. In some embodiments, thickness $h_3$ of film 10 is approximately 0.3 mm. In some embodiments, thickness $h_3$ of film 10 is approximately 0.4 mm. In some embodiments, thickness $h_3$ of film 10 is approximately 0.5 mm.

In one embodiment, the thickness $h_3$ of the film 10 is approximately uniform throughout film body 11. In some embodiments, the film 10 is tapered toward one or more edges along the outer periphery 13. In some embodiments, thickness $h_3$ of film 10 differs in two or more sections of the film body 11 to control strength or drug delivery of each area.

In some embodiments, the film 10 is of sufficient strength to withstand mechanical forces such as implantation, drilling and screw placement. In other embodiments, the film 10 has tensile properties that permit a region of the film to tear upon penetration of a screw or other fixation element through that region. This has the advantage of preventing the film from becoming entangled with or otherwise wrapped around the fixation element, which can potentially cause damage to the film and inhibit the correct placement of the fixation element. In one embodiment, film 10 has a first tensile strength in a first planar direction and a second tensile strength in a second planar direction that is perpendicular to the first planar direction, where the first tensile strength is substantially equal to the second tensile strength. In one embodiment, film 10 has the strength characteristics as listed in tables 1-3 below. Each of the six samples listed in the Tables below were films comprised of a copolymer containing approximately 70% glycolide, 17% caprolactone, 8% trimethylene carbonate, and 5% lactide by weight.

TABLE 1

| Film Sample | Start Date | Specimen label | Length (mm) | Width (mm) | Thickness (mm) | Tensile strain at Yield (Offset 0.2%) (%) |
|---|---|---|---|---|---|---|
| 1 | Jul. 2, 2009 9:02AM | Day 0 Sample 1 | 50.00 | 10.510 | 0.059 | 2.44051 |
| 2 | Jul. 2, 2009 9:05AM | Day 0 Sample 2 | 50.00 | 11.160 | 0.063 | 3.43452 |
| 3 | Jul. 2, 2009 9:07AM | Day 0 Sample 3 | 50.00 | 11.230 | 0.062 | 2.04468 |
| 4 | Jul. 2, 2009 9:09AM | Day 0 Sample 4 | 50.00 | 10.740 | 0.057 | 2.81023 |
| 5 | Jul. 2, 2009 9:13AM | Day 0 Sample 5 | 50.00 | 11.180 | 0.066 | 3.06678 |
| 6 | Jul. 2, 2009 9:15AM | Day 0 Sample 6 | 50.00 | 10.920 | 0.058 | 3.65944 |
| Mean | | | 50.00 | 10.957 | 0.061 | 2.90936 |
| Standard Deviation | | | 0.000 | 0.288 | 0.003 | 0.607 |
| Coefficient of Variation | | | 0.000 | 2.625 | 5.639 | 20.854 |

TABLE 2

| Film Sample | Tensile stress at Yield (Offset 0.2%) (MPa) | Tensile strain at Maximum Load (%) | Tensile stress at Maximum Load (MPa) | Tensile strain at Break (Standard) (%) |
|---|---|---|---|---|
| 1 | 13.75364 | 22.50031 | 26.31165 | 31.66499 |
| 2 | 14.00508 | 31.66468 | 27.57964 | 49.99874 |
| 3 | 9.25147 | 32.49843 | 26.60082 | 149.99967 |
| 4 | 12.82553 | 26.66562 | 28.46340 | 55.83280 |
| 5 | 13.53060 | 23.33406 | 26.59371 | 36.66562 |
| 6 | 12.60631 | 35.83187 | 26.79990 | 212.49840 |
| Mean | 12.66211 | 28.74916 | 27.05819 | 89.44337 |
| Standard Deviation | 1.756 | 5.393 | 0.812 | 74.322 |
| Coefficient of Variation | 13.865 | 18.760 | 3.000 | 83.094 |

TABLE 3

| Film Sample | Tensile stress at Break (Standard) (MPa) | Modulus (Automatic Young's) (MPa) |
|---|---|---|
| 1 | 15.20147 | 749.15765 |
| 2 | 21.71590 | 504.50877 |
| 3 | 19.08817 | 657.83084 |
| 4 | 18.08469 | 574.31825 |
| 5 | 18.71550 | 618.69300 |
| 6 | 21.75346 | 436.82724 |
| Mean | 19.09320 | 590.22262 |
| Standard Deviation | 2.460 | 111.150 |
| Coefficient of Variation | 12.885 | 18.832 |

In one embodiment, film 10 has a tensile strain at yield (Offset 0.2%) of approximately 2% to approximately 4% and/or a mean tensile strain of approximately 3%. In one embodiment, film 10 has a tensile stress at yield (Offset 0.2%) of approximately 9 MPa to approximately 14 MPa, and/or a mean tensile stress at yield of approximately 12.5 MPa. In one embodiment, film 10 has a tensile stress at maximum load of approximately 25 MPa to approximately 30 MPa, and/or a mean tensile stress at maximum load of approximately 27 MPa. In one embodiment, film 10 has a tensile strain at break (standard) of approximately 30% to approximately 215%, and/or a mean tensile strain at break of approximately 89%. In one embodiment, film 10 has an automatic Young's modulus of approximately 430 MPa to approximately 750 MPa, and/or a mean automatic Young's modulus of approximately 590 MPa. Film 10 may be characterized by combination of one or more of the foregoing properties.

Referring to FIGS. 1A, 1B, 2, 11K and 11L, in some embodiments, film 10 includes a plurality of apertures or apertures 14. In one embodiment, the apertures 14 allow the passage or transport of fluids through film 10 (e.g., when implanted near living tissue). In some embodiments, it may be important to allow for fluid flow from one side of the sleeve to the other (inside to outside) in order, for example, to avoid creating a "dead space" between the film 10 and the bone plate 12. Additionally, the apertures 14 may advantageously provide more even distribution of the drug or biological agent to adjacent tissue and bone as the material leaches out of the polymer than a sleeve without such apertures.

The apertures 14 may be configured to be any size and shape, including variations within the same polymer film. In one embodiment, apertures 14 are defined by substantially cylindrical sidewalls. In some embodiments, apertures 14 have sidewalls that have segments that are inwardly facing convex surfaces. In some embodiments, the inwardly facing convex surface is substantially parabolic. Apertures 14 need not be perfectly round in cross section, and in some embodiments, may be ovoid, elliptical, star or diamond in shape. In some embodiments, apertures 14 extend to one or more apexes. In one embodiment, such apexes promote tears in film 10 during use (e.g., where a zone of weakness is created by the aperture). In one embodiment, apertures 14 extend completely through sheet 12 from the first surface 10a to the second surface 10b (see FIG. 4C). In one embodiment, one or more of the apertures 14 can extend only partially through film 10, for instance from the second surface 10b toward but not to the first surface 10a, to control drug release or increase the initial strength of the film 10. In certain embodiments, the film 10 may have a first one or more regions having the apertures 14 and a second one or more regions devoid of the apertures 14. A film region can be defined as any single contiguous area, substantially either elliptical or quadrangular, of at least 10% of the total surface area of film surface 10a or 10b. According to one embodiment, one or more regions having apertures 14 can be separated by one or more regions having no apertures 14. According to another embodiment, a region having apertures is contiguous, and in a further embodiment a region having no apertures is contiguous. For example the periphery of the film 10 can have apertures while the remainder of the film is devoid of apertures, or alternatively a periphery of film 10 can be devoid of apertures while the remainder of the film has apertures. It should be appreciated that the distribution pattern can be configured as desired to include more or less apertures in any one region of the film, as well as permitting an even or regular distribution of apertures throughout the film.

The apertures 14 may be configured to allow for any desired porosity of film 10. In one embodiment, the porosity of the film 10 is the range of approximately 1% to approximately 30%, in another embodiment approximately 5% to about 25%, in another embodiment approximately 10% to about 20%, and in a preferred embodiment is approximately 15%. In one embodiment, the porosity of film 10 is greater than approximately 1%. In one embodiment, the porosity of film 10 is greater than approximately 2%. In one embodiment, the porosity of film 10 is greater than approximately 3%. In one embodiment, the porosity of film 10 is greater than approximately 4%. In one embodiment, the porosity of film 10 is greater than approximately 5%. In one embodiment, the porosity of film 10 is greater than approximately 6%. In one embodiment, the porosity of film 10 is greater than approximately 7%. In one embodiment, the porosity of film 10 is greater than approximately 8%. In one embodiment, the porosity of film 10 is greater than approximately 9%. In one embodiment, the porosity of film 10 is greater than approximately 10%. In one embodiment, the porosity of film 10 is greater than approximately 11%. In one embodiment, the porosity of film 10 is greater than approximately 12%. In one embodiment, the porosity of film 10 is greater than approximately 13%. In one embodiment, the porosity of film 10 is greater than approximately 14%. In one embodiment, the porosity of film 10 is greater than approximately 15%. In one embodiment, the porosity of film 10 is greater than approximately 16%. In one embodiment, the porosity of film 10 is greater than approximately 17%. In one embodiment, the porosity of film 10 is greater than approximately 18%. In one embodiment, the porosity of film 10 is greater than approximately 19%. In one embodiment, the porosity of film 10 is greater than approximately 20%.

Figure 11D:
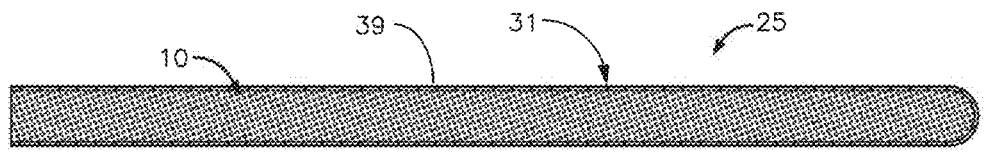
FIG. 11D is a top plan view of a sleeve that comprises at least one polymer film of the type illustrated in FIG. 1, shown in another configuration.
Figure 11E:
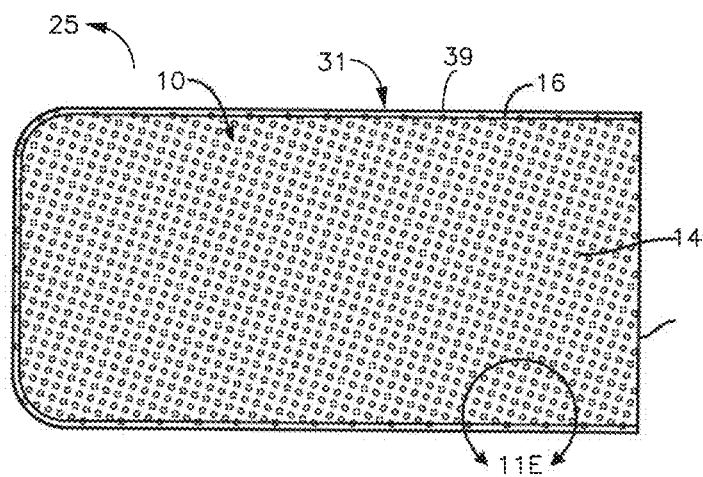
FIG. 11E is a top plan view of a sleeve that comprises at least one polymer film of the type illustrated in FIG. 1, shown in another configuration.
Figure 11F:
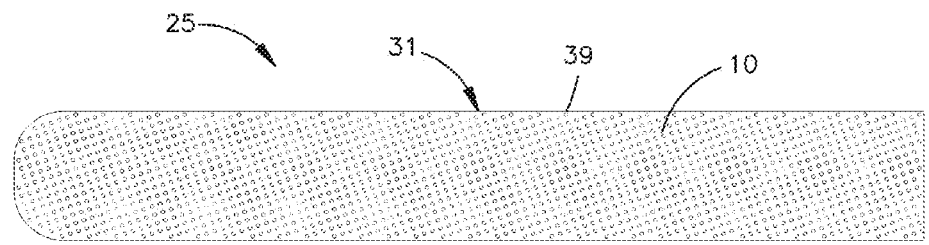
FIG. 11F is a top plan view of a sleeve that comprises at least one polymer film of the type illustrated in FIG. 1, shown in another configuration.
Figure 11L:
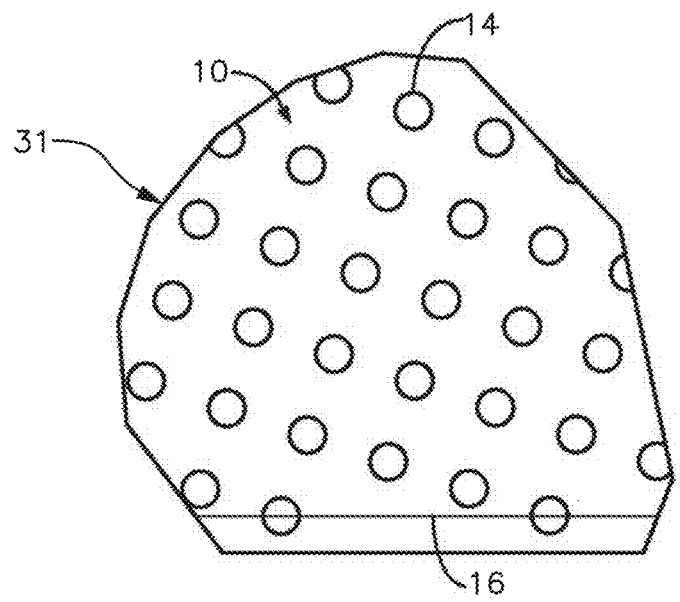
FIG. 11L is an enlarged top plan view of a portion of each of the sleeves as illustrated in FIGS. 11A-J, such as a top plan view of the area within region 11E in FIG. 11E.
Figure 11M:
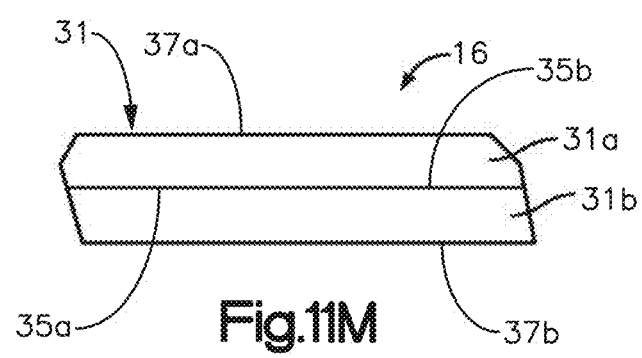
FIG. 11M is an enlarged view of a seam of a sleeve such as those shown in FIGS. 11A-11J.

Referring to FIG. 11L, in one embodiment, the apertures 14 have an average maximum cross-sectional length (e.g., diameter) in the range of approximately 0.1 mm to approximately 1.5 mm, such as approximately 0.1 mm to 1.0 mm, 0.1 mm to 0.5 mm, 0.5 mm to 1.5 mm, 0.5 mm to 1.0 mm, 0.1 mm to 0.75 mm, 0.5 mm to 0.75 mm, 0.75 mm to 1.0 mm, and 0.75 mm to 1.5 mm. In a preferred embodiment apertures 14 have an average maximum cross-sectional length (e.g., diameter) of about 0.75 mm. In one embodiment, apertures are spaced apart from adjoining apertures in the range of approximately 0.5 mm to about 5 mm. such as approximately 0.5 mm to approximately 2.5 mm, 2.5 mm to 5.0 mm, 1.0 mm to 2.0 mm, 1.5 mm to 2.0 mm, 0.5 mm to 1.0 mm, 0.5 mm to 1.75 mm, and 1.0 mm to 1.75 mm. In a particularly preferred embodiment, apertures have an average maximum cross-sectional length of 0.75 mm and a spaced apart approximately 1.75 mm. In a preferred embodiment, apertures 14 are spaced apart approximately 1.75 mm. In one embodiment, the apertures 14 are arranged in a regular array (e.g., aligned rows and columns as illustrated in FIG. 11K). In one embodiment, the apertures 14 are arranged in an irregular array. Thus, the apertures 14 can generally be configured such that a diameter of the threaded shaft of the bone screw that is driven through the film 10, an aligned bone fixation hole of the bone implant, and the underlying bone, is greater than both the cross-sectional dimensions of the apertures 14 and the gap between adjacent apertures 14, such that a given screw shaft is configured to be driven through a region of the film 10 that includes more than one aperture 14. It should be appreciated that the shaft of the bone fixation screw can be driven through at least one of the apertures 14, such as a plurality of the apertures 14, through the aligned bone implant hole, and into the underlying bone. The step of driving the screw shaft through at least one or more of the apertures 14 can decrease random unpredictable tearing of the film compared to a step of driving the screw shaft through a region of the film 10 that is devoid of apertures 14.

Figure 4A:
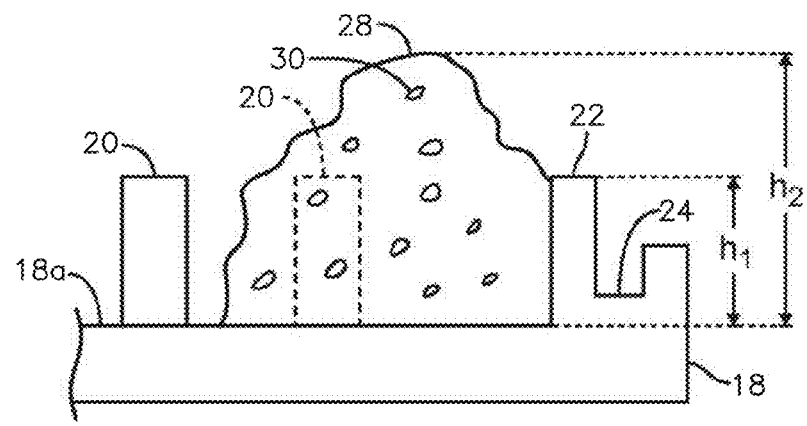
FIG. 4A is a schematic side cross-sectional view of the mold of FIG. 3A with the polymer added.
Figure 4B:
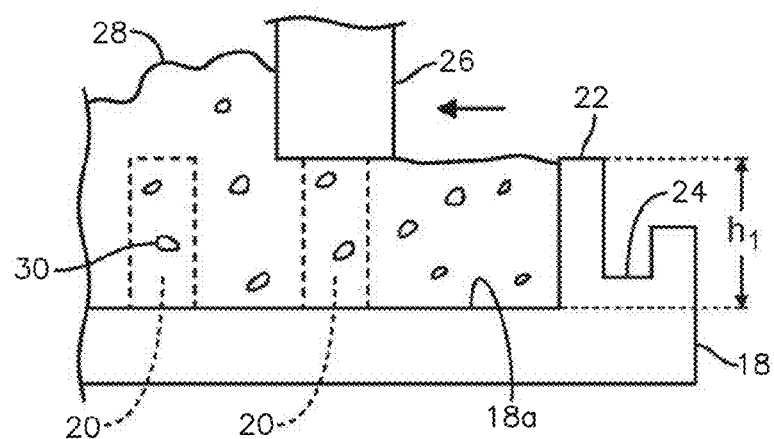
FIG. 4B is a schematic side cross-sectional view of the mold shown in FIG. 4A showing the drawing device drawing the polymer across the mold.
Figure 4C:
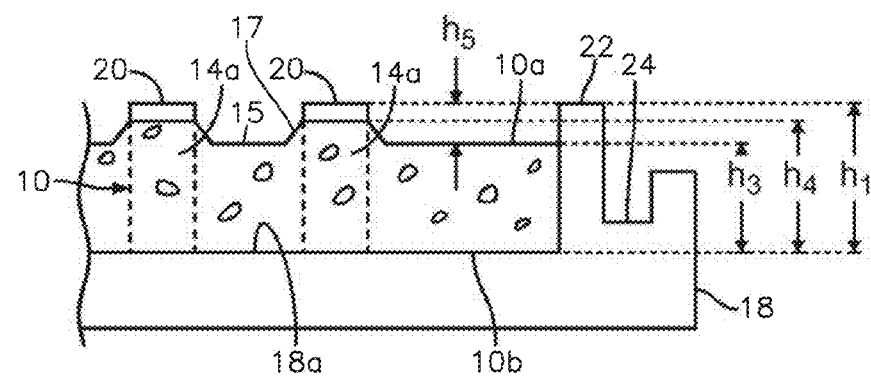
FIG. 4C is a schematic side cross-sectional view of the mold shown in FIG. 4A showing the polymer after being drawn across the mold and solidified to form a polymer film.

Referring to FIGS. 1A, 1B and 4C, in some embodiments, the first surface 10a can define a contiguous planar portion 15 and interfaces, which can be configured as solidified meniscuses 17 as described below, that adjoin the contiguous planar portion 15 and one or more interior surfaces that define a respective one of the apertures 14. In accordance with one embodiment, one or more of the meniscuses 17 can be configured as a raised lip 14a that extends out with respect to the contiguous planar portion 15 (e.g., along a direction from the second surface 10b toward the first surface 10a) along the transverse direction T, and thus extends out from the first surface 10a. A benefit of the raised lip 14a around each aperture 14 may include providing a reinforcement or grommet to each aperture 14, effectively increasing the mechanical strength of the film 10 relative to a similar perforated film that is devoid of raised lips 14a. A further benefit of the raised lips 14a may include a texture on the first surface 10a. Such a texture may be an advantage for tactile feel or for the purpose of increasing (or reducing) friction of the first surface 10a of the film 10 when, for example, the first surface 10a is in contact with another surface. In one embodiment, the raised lips 14a decrease the tendency of the film 10 to adhere to a surface such as the metal surface of an implant, making it easier to slide a sleeve made from the film 10 onto the bone plate 12. In one embodiment, the lips 14a provide stand-off between the bone plate 12 and the film 10, thereby reducing the surface area of the film 10 that is in contact with the bone plate 12.

In one embodiment, the contiguous planar portion 15 extends between the plurality of raised protruding lips 14a, for instance from each of the raised lips 14a to others of the raised lips 14a. In one embodiment, the raised lips 14a are substantially in the shape of the outer surface of an impact crater. In one embodiment, the raised lips 14a define a continuous concave outer surface. In one embodiment, the concave outer surface is a parabolic concave surface. In one embodiment, one or more of lips 14a (or, in some embodiments, each lip 14a) has a concave outer surface and an opposed convex inner surface, either or both of which are parabolic in shape. In one embodiment, the lips 14a can each have an edge that is raised above the contiguous planar portion 15 of first surface 10a by approximately 0.1 mm to approximately 1.0 mm. In one embodiment, lips 14a each have an edge that is raised above the contiguous planar portion 15 of first surface 10a by approximately 0.1 mm. In one embodiment, lips 14a each have an edge that is raised above the contiguous planar portion 15 of first surface 10a by approximately 0.2 mm. In one embodiment, lips 14a each have an edge that is raised above the contiguous planar portion 15 of first surface 10a by approximately 0.3 mm. In one embodiment, lips 14a each have an edge that is raised above the contiguous planar portion 15 of first surface 10a by approximately 0.4 mm. In one embodiment, lips 14a each have an edge that is raised above the contiguous planar portion 15 of first surface 10a by approximately 0.5 mm. In one embodiment, lips 14a each have an edge that is raised above the contiguous planar portion 15 of first surface 10a by approximately 0.6 mm. In one embodiment, lips 14a each have an edge that is raised above the contiguous planar portion 15 of first surface 10a by approximately 0.7 mm. In one embodiment, lips 14a each have an edge that is raised above the contiguous planar portion 15 of first surface 10a by approximately 0.8 mm. In one embodiment, lips 14a each have an edge that is raised above the contiguous planar portion 15 of first surface 10a by approximately 0.9 mm. In one embodiment, lips 14a each have an edge that is raised above the contiguous planar portion 15 of first surface 10a by approximately 1.0 mm.

In one embodiment, the lips 14a impart a first tactile feel to the first surface 10a that is different (e.g., distinguishable by a surgeon wearing a surgical glove) from a second tactile feel of second surface 10b that is devoid of the lips 14a. In one embodiment, apertures 14 in one or more areas on first surface 10a each are bounded by a raised lip 14a and apertures 14 in one or more other areas on first surface 10a are not so bounded. In one embodiment, the solidified meniscus 17 can define a height $h_4$ (see FIG. 4C) from the second surface 10b to the outermost end of the raised lips 14a. The height $h_4$ can be defined by the raised lips 14a, and can be uniform across the first surface 10a in accordance with one embodiment. In one embodiment, at least one of the raised lips 14a has a height $h_4$ that is different than the height $h_4$ of at least one other of the raised lips 14a. In one embodiment, one or more apertures 14 are bounded by a lip 14a on one or both first surface 10a and second surface 10b. An embodiment such as the one illustrated in FIG. 1A, may include a single continuous lip 14a that surrounds each aperture 14. The continuous lip may be substantially uniform in thickness and/or substantially uniform in height relative to any one aperture, or from aperture 14 to aperture 14. The apertures 14 may be evenly spaced apart across all or at least a portion of the film 10. In other embodiments, at least a portion of the film 10 is characterized by apertures 14 that are spaced apart in at least two different spacing configurations, so as to define two different patterns of apertures 14.

In some embodiments, the film 10 includes one or more drugs or other substance for delivery in the body. Such drugs include, but are not limited to, antimicrobial agents, anti-fibrotic agents, anesthetics and anti-inflammatory agents as well as other classes of drugs, including biological agents such as proteins, growth inhibitors and the like. In further embodiments, the film 10 can include one or more biocompatible particles. The particles, according to one embodiment, can assist in bone remodeling and regrowth. For example, in certain embodiments, particles are calcium-containing salt particles, such as calcium phosphate or calcium sulfate particles. These calcium salts are well known for use at bone remodeling and regrowth sites. Other potential biocompatible particles can include salts or oxides containing, for example, silicon, magnesium, strontium, and zinc. In certain embodiments, the particles are at least partially insoluble and can be substantially insoluble in the polymer film. In embodiments where the particles are insoluble in the film, the particles provide heterogeneous nucleation sites in the polymer film. Such nucleation sites can increase the rate of crystallization of the film as well as increasing the overall crystallinity of the film as compared to the film without such nucleation sites. Altering the crystallinity properties of a polymer film can be desired where a decrease in elastic behavior is preferred. For example, FIGS. 12 and 13 (and explained more fully below) show the decrease in elongation and yield properties of a plain polymer film upon the incorporation of insoluble biocompatible particles (in this case, 5% and 10% addition of insoluble gentamicin sulfate particles). Additionally, an increase in crystallinity can be a factor that potentially slows the degradation rate of a biodegradable polymer film.

In one embodiment, the film 10 includes an active agent, such as a drug or drugs. The active agent may be an anti-microbial agent, for instance an antibiotic, anti-viral agent, or anti-parasitic agent, though as previously mentioned, it should be appreciated that other active agents typically used in conjunction with orthopedic surgery are also contemplated within the scope of this disclosure, including, for example, anti-inflammatory drugs, steroids, analgesics, opioids, growth factors, and the like. In embodiments including an antibiotic, the antibiotic selected may be active against the majority of bacteria found in orthopedic implant related infections. These include primarily staphylococci, and Gram negative bacilli.

In one embodiment, the drug selected is stable during the manufacturing process that fabricates the film. Depending upon the manufacturing processes utilized, the polymer formulation of the film, the preferred drug, and the pharmaceutical formulation of the preferred drug (e.g., the particular pharmaceutical salt utilized) the drug can either be soluble or insoluble with the polymer formulation. In embodiments where the drug is at least partially—including being substantially—insoluble in the polymer, the film can physically entrap the drug particles. In embodiments where the drug is at least partially—including being substantially—soluble with the polymer, the film can chemically bond with and to the drug. In certain embodiments, the film can both physically entrap and chemically bond with and to the drug In one embodiment, film 10 includes gentamicin sulfate. Gentamicin sulfate is thermally stable above 100° C., and is stable to organic solvents including DMSO, which is used in the manufacturing process in some embodiments. Gentamicin sulfate is active against many bacteria commonly associated with orthopedic infection, such as *Staphylococcus aureus* including MRSA, coagulase negative staphylococci, and Gram negative rods such as *Pseudomonas* and *Enterobacter* species. Without being bound by any particular theory, it is believed that local delivery of gentamicin to a fracture site containing a metallic implant may be effective in preventing infection by some bacteria which are intermediate or resistant to systemic levels of gentamicin because of the locally higher concentrations of gentamicin at the fracture site.

Referring to FIGS. 4A-4C, in one embodiment, film 10 comprises a drug that is at least partially insoluble and can be substantially insoluble in the film, such that the drug can serve as a biocompatible particle that provides a heterogeneous nucleation site as previously mentioned. In a further embodiment, film 10 comprises a plurality of discrete eluting drug components 30. In one embodiment, film 10 is configured to elute the plurality of discrete drug components 30 at different time periods following implantation. In one embodiment, the elution of drug components 30 (e.g., an antibiotic such as gentamicin) in vivo is a two-phase process, with a burst release occurring as soon as film 10 contacts water or body fluid, and a second phase which is controlled by the degradation rate of the polymer. In some embodiments, it is desirable to have an initial burst release of gentamicin to reduce bacterial contamination of the wound site on initial implantation, then a lower level release of gentamicin for a period of days to weeks afterward, to prevent growth and/or biofilm formation of any surviving bacteria. In one embodiment, film 10 is configured to elute up to approximately 20 percent of the drug within the first hour after implantation. In another embodiment, film 10 is configured to elute up to approximately 60 percent of the drug contained within film 10 approximately 1 week after film 10 has been implanted in contact with living tissue. In another embodiment, film 10 is configured to elute up to approximately 100% of the drug within 10 days after implantation. In one embodiment, the combination of particle size and polymer degradation rate control the drug release profile, and create the desired 2-phase release. In one embodiment, the drug is released over a 2 to 3 week time period. In other embodiments, the drug is released over a shorter or longer time frame.

In one embodiment, where the drug is insoluble with the film, the relative amounts of drug released during these two phases are controlled by the particle size of the drug in the film. In one embodiment, drug components 30 are evenly distributed throughout film 10, and any drug components 30 in contact with a surface of film 10 are dissolved more rapidly than a drug component 30 that is not in contact with a surface of film 10. In one embodiment, a quantity of drug components 30 that are in contact with a surface of film 10 upon implantation are configured to release in a burst upon implantation. In one embodiment, the larger the size of drug components 30, the higher the proportion of drug components 30 in contact with the surface, and the greater the burst release. For this reason, the size of drug components 30, in one embodiment, is kept under 10 microns in diameter which reduces the burst release to approximately 20 to 35% of the total drug content. In one embodiment, drug components 30 are under 20 microns in diameter.

In one embodiment, film 10 is configured to deliver multiple drugs from one or more independent layers, some of which may contain no drug. In certain embodiments, one or more of the layers may be a drug containing layer and/or a rate controlling layer for drug release (with or without a drug contained therein). In another embodiment, film 10 may include a plurality of drug components each being characterized by a different release rate from film 10 such that a first drug is associated with a first release profile that is different from a second release profile of a second drug.

Where the film contains one or more antibiotics that can release from the film into the surgical site environment over a period a time, a Zone of Inhibition (ZOI) can be formed around the film where certain bacterial growth cannot occur due to the presence of the antibiotic containing film. Where the film defines a central axis or center point, the ZOI is defined as the radial distance extending in three dimensions from the central axis or center point where bacteria will not colonize. According to one embodiment, the film has a ZOI of at least 12 mm. According to one embodiment, where the film includes the antibiotic gentamicin (13% by weight), the film has a ZOI of at least 20 mm where the bacteria are selected from *S. aureus, S. epidermidis, Pseudomonas aeruginosa,* or *Enterobacter cloacae,* or combinations thereof Accordingly, when the film 10 defines a cover suitable for use in combination with a medical implant, the cover does not have to overlay the entire surface area of an implant to be effective, and can thus overlay at least a portion of the surface area of one or both sides (e.g., the bone-facing side and the side opposite the bone-facing side) of the implant up to an entirety of the surface area of one or both sides of the implant. For example, in those cases where at least one film 10 defines a cover configured as a polymer film sleeve 31 (see, e.g., FIGS. 11A-J) designed to completely cover an implant, such as the bone plate 12, the film 10 may be torn or damaged during fracture reduction and plating, or otherwise does not cover the entire surface of the implant. Alternatively, the sleeve can be designed to cover only a portion of the implant. In this manner, a surgeon can determine an appropriate zone of inhibition needed for a particular surgical site and/or medical implant, and utilize the polymer film accordingly, e.g., utilize the appropriate length and/or quantity of polymer film.

Referring to FIGS. 3A-10, there are shown devices used in a method of manufacturing films 10 in accordance with exemplary embodiments of the present disclosure.

In one embodiment, a manufacturing method creates polymer films 10 for drug delivery. In one embodiment, the film 10 is solvent cast. In some embodiments, solvent casting methods are advantageous in the fabrication of films 10 that contain a drug component 30 that could be potentially damaged by the heat and shear of melt processes such as blown film extrusion. Producing films 10 using a punch press (e.g., with many hundreds or thousands of holes or holes with complicated geometry) may also be time consuming and expensive.

In some embodiments, methods described herein can create the thin films 10 and the apertures 14 in a single step. In some embodiments, methods described herein create the film 10 and thousands of apertures 14 within the periphery of the film with accurate predetermined control of geometry and placement of the apertures 14 and accurate predetermined control of the thickness of the film 10.

Referring to FIGS. 3A-3G, in some embodiments, the film 10 is cast in a mold 18. In one embodiment, mold 18 includes a plurality of protrusions or posts 20 extending from a bottom 18a of mold 18. When polymeric solution is deposited in the mold 18, the posts 20 occupy space that defines the apertures 14 when the polymeric solution solidifies into film 10. In one embodiment, the mold 18 is comprised of injection molded polypropylene. The mold 18 may be manufactured from other materials, including polymers (see FIG. 3F), glass, metals (see FIG. 3G) or ceramics. In one embodiment, the mold 18 is comprised of two or more materials. For example, the bottom 18a of the mold 18 may be made from metal with a polymer coating to reduce adhesion of the cast film to the mold and/or to form posts 20. The cavity in the mold may be formed by a casting process, a compressing molding process, an injection molding process, a chemical etching process or a machining process.

In one embodiment, the mold 18 includes a cavity depth of approximately 0.25 mm. In one embodiment, a distance from the bottom of the mold 18 to a top of each of the plurality of the posts 20 is equal to the cavity depth (i.e., the height of peripheral wall 22) or vice versa. In one embodiment, the posts 20 are longer than the desired thickness of the film 10. In one embodiment, the posts 20 extend 0.3 mm from the bottom 18a of the mold 18. In one embodiment, posts 20 extend 0.2 mm from the bottom 18a of the mold 18. In one embodiment, the posts 20 extend 0.25 mm from the bottom 18a of the mold 18. In one embodiment, the posts 20 extend 0.3 mm from the bottom 18a of the mold 18. In one embodiment, the posts 20 extend 0.35 mm from the bottom 18a of the mold 18. In one embodiment, the posts 20 extend 0.4 mm from the bottom 18a of the mold 18. In one embodiment, the posts 20 extend 0.45 mm from the bottom 18a of the mold 18. In one embodiment, the posts 20 extend 0.5 mm from the bottom 18a of the mold 18.

In one embodiment, the posts 20 are arranged to produce a predetermined selected size, shape, pattern, and arrangement of the apertures 14 described above. In one embodiment, a perimeter form or peripheral wall 22 of the mold 18 defines a total mold area, and the plurality of posts 20 define an area that is substantially equal to or corresponding to the ultimate porosity of the film 10.

In one embodiment, the mold 18 includes a trough 24 that extends at least partially around the peripheral wall 22 of mold 18. In one embodiment, the trough 24 extends around the entire peripheral wall 22 of mold 18. In some embodiments, the trough 24 retains any excess polymer that flows or is urged from the cavity of the mold over the peripheral wall 22. In one embodiment, the mold 18 includes an extension 40, which can define a handle that extends out from at least one outer edge of the mold 18. In one embodiment, the extension 40 is provided for grasping and manipulating the mold 18 without contacting the polymer solution that is disposed within the mold 18.

According to the present disclosure, there is a method of producing a polymer film comprising: placing a polymer solution into a mold having a plurality of protrusions extending from a bottom of the mold. In certain embodiments, the polymer solution is characterized by a viscosity that inhibits the unaided flow of the polymer throughout the mold. The process further includes urging the polymer solution around each of the plurality of protrusions; and solidifying the polymer solution. In one embodiment, the mold includes a perimeter form extending to an elevation that is substantially equal to an elevation of each of the plurality of protrusions. In one embodiment, the urging comprises drawing an urging instrument such as a blade, bar, squeegee or roller across the perimeter form and the plurality of protrusions to force the polymer solution to flow around the plurality of protrusions and throughout the mold such that the polymer solution has a substantially uniform thickness. In one embodiment, at least a portion of an outer surface of a protrusion, for example an upper portion of a protrusion, is substantially free of polymer solution after the drawing. In one embodiment, the placing step includes depositing the polymer solution in the mold such that a portion of the polymer solution is above the elevation of the perimeter form and the protrusions. In still further embodiments, one or more of the method steps can be repeated such that the method can produce a film comprising a plurality of layers, for example, two or more layers, such as two layers, three layers, four layers, up to and including seven layers. In certain embodiments the method additionally includes the steps of placing one or more additional polymer solutions (for example, placing an additional polymer solution, placing a second additional polymer solution, placing a third additional polymer solution, up to and including placing a sixth additional polymer solution) in the mold over a first polymer solution, and urging the one or more polymer solutions around each of the plurality of protrusions. The step of placing one or more polymer solutions in the mold can occur prior to, during, or after the step of solidifying the polymer solution. Thus, according to one embodiment of the method, each of the one or more polymer solutions placed in the mold can solidify prior to, during, or after, the step of placing the next or subsequent additional polymer solution into the mold (e.g., placing a third additional polymer solution into the mold prior to, during, or after, solidifying the second additional solution; or placing an additional polymer solution into the mold prior to, during, or after solidifying a first polymer solution). According to another embodiment, all of the polymer solutions placed into the mold can solidify substantially simultaneously. According to one embodiment, the one or more polymer solutions comprise a polymer solution that can solidify into an adhesive layer, and according to another embodiment, the one or more polymer solutions comprise a rate controlling layer for drug release.

In one embodiment, a polymer solution 28 is formed. The polymer solution 28 is placed in the cavity of the mold 18 so as to create the film 10. In some embodiments where the drug is insoluble in the polymer, a solvent and drug component 30 are first mixed to form a well distributed suspension, and then polymer is added and dissolved in the solvent/drug suspension. In other embodiments, the polymer is dissolved in the solvent and then the insoluble drug is added to the solution at the desired amount. In still other embodiments, the drug is soluble in the polymer/solvent solution. In embodiments where aliphatic polyesters comprise the polymer formulation, typically a polar solvent will be used. Suitable polar solvents can include dimethyl sulfoxide (DMSO), tetrahydrofuran (THF), alcohols, acetone, ethyl acetate, acetonitrile, dimethylformamide (DMF), and formic acid. In one embodiment, a polymer material is dissolved at a 4:1 solvent to polymer ratio in dimethyl sulfoxide (DMSO) at elevated temperature and the drug gentamicin sulfate is added at 13% by weight. In one embodiment, polymer solution 28 is formed by introducing drug units 30 to a polymer/solvent blend at a temperature below 90° C. In one embodiment, polymer solution 28 comprises a cross-linkable pre-polymer such as polyurethanes, polyfumarates, polymethacrylates, etc.

Figure 6:
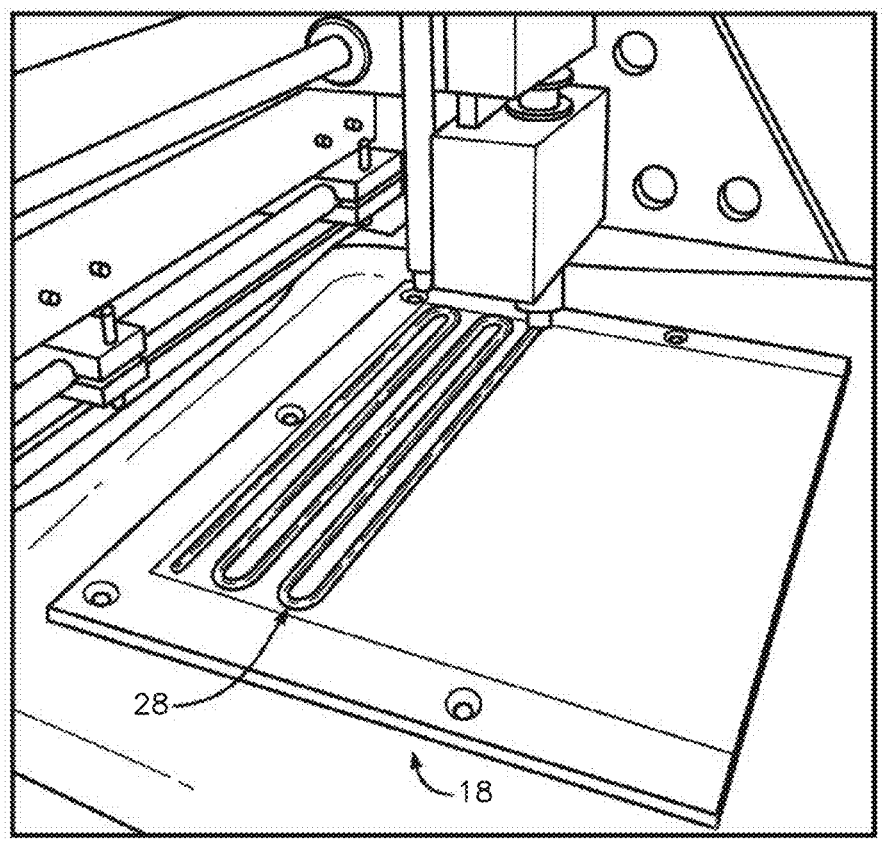
FIG. 6 is a perspective view of the automated casting apparatus of FIG. 5 showing the polymer being added to the mold.
Figure 8:
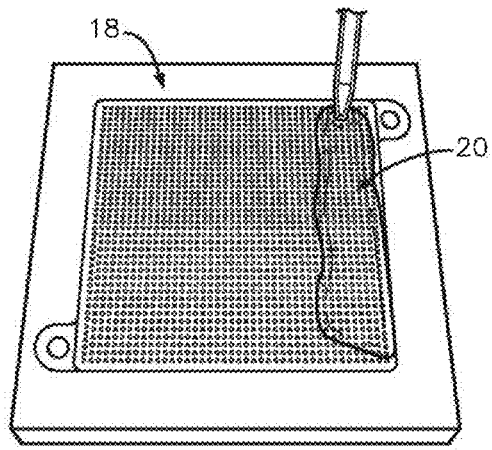
FIG. 8 is a perspective view of polymer being added to a mold in accordance with another exemplary embodiment of the present disclosure.

Referring to FIGS. 4A, 6 and 8, once the polymer solution 28 is prepared, polymer solution 28 is placed into the mold 18, which can be a one sided mold as illustrated. In some embodiments, the viscosity of polymer solution 28 and/or the density of posts 20 substantially inhibits the unaided flow of the polymer 28 throughout the mold 18. In one embodiment, after adding polymer solution 28 to mold 18, the top surface of polymer solution 28 is a height $h_2$ above the base 18a of mold 18 which is greater than a height $h_1$ of the mold cavity and posts 20.

Figure 7:
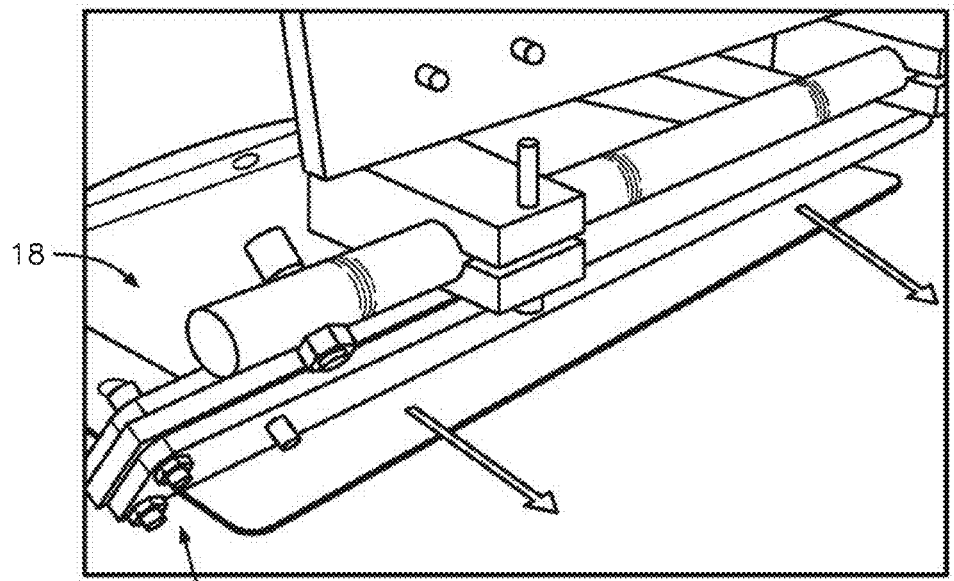
FIG. 7 is a perspective view of the automated casting apparatus of FIG. 5 showing the drawing device drawing the polymer across the mold.
Figure 9:
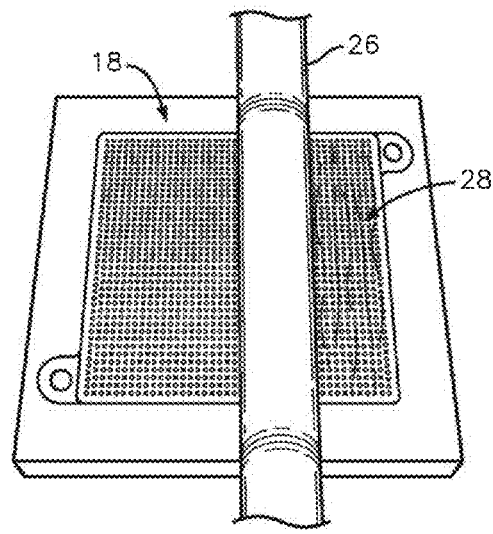
FIG. 9 is a perspective view of the mold of FIG. 8 showing the drawing device drawing the polymer across the mold.

Referring to FIGS. 4B, 7 and 9, after the polymer solution 28 has been added to the mold 18, in one embodiment, the polymer solution 28 can be urged around each of the plurality of posts 20 in the cavity of the mold 18. For instance, any suitable urging instrument 26 can urge the polymer solution around each of the plurality of posts 20. In one embodiment, urging instrument 26 can be, for example, a blade, bar, squeegee or roller that slides, or the mold 18 is moved relative to urging instrument 26, across the perimeter wall 22 and over the posts 20 to force polymer solution 28 to flow around posts 20 and throughout mold 18 such that polymer solution 28 has a substantially uniform thickness. In one embodiment, drawing the urging instrument 26 across mold 18 causes the urging instrument 26 to remove excess polymeric film material from the top surface of posts 20. In one embodiment, an outer surface, such as an upper surface, of one or more posts 20 is substantially free of polymer solution 28 after the drawing.

Referring to FIG. 4C, once the polymer solution 28 is drawn or spread throughout mold 18, the polymer solution 28 is solidified to form the film 10. In one embodiment, the mold 18 can be placed into a solvent drying oven at an elevated temperature to remove the solvent, leaving behind a thin cast film. In one embodiment, the polymer solution 28 is solidified by cross-linking the polymer by applying UV radiation, temperature change, polymerization catalysts, soluble crosslinking agents or combinations thereof to the polymer solution 28. In one embodiment, the solidifying step includes exposing the mold 18 containing the polymer solution 28 to a second solvent. In one embodiment where, for example, the polymer solution 28 includes polymer, a drug and a first solvent, the first solvent is soluble in the second solvent, but the polymer and drug component are not soluble in the second solvent. Thus, by exposing the polymer solution 28 to the second solvent, the first solvent is removed from the polymer solution leaving the polymer and the drug product to solidify to form, for example, the film.

In one embodiment, solidifying the polymer solution reduces a thickness of the polymer solution from a first thickness $h_1$ to a second thickness $h_3$. In one embodiment, solidifying the polymer solution reduces a thickness of the polymer solution proximate to posts 20 from a first thickness $h_1$ to a second thickness $h_4$. In one embodiment, the thickness $h_4$ of the film 10 proximate the posts 20 is greater than the thickness $h_1$ of the film 10 between the posts 20. In one embodiment, the lips 14a can be created due to the polymer solution forming a meniscus around each of posts 20 during solidifying of the polymer solution 28 to form the film 10. In one embodiment, the meniscuses formed about the posts 20 define the lips 14a when the polymer solution 28 has solidified. In one embodiment, height $h_4$ of lips 14a may be controlled by careful selection of the material and geometry of the posts 20 or by coating the posts 20 with, for example, a lubricious material such as a fluoropolymer or silicone mold release. In one embodiment, the height $h_4$ of the lips 14a is controlled by the concentration of the polymer solution.

Figure 4D:
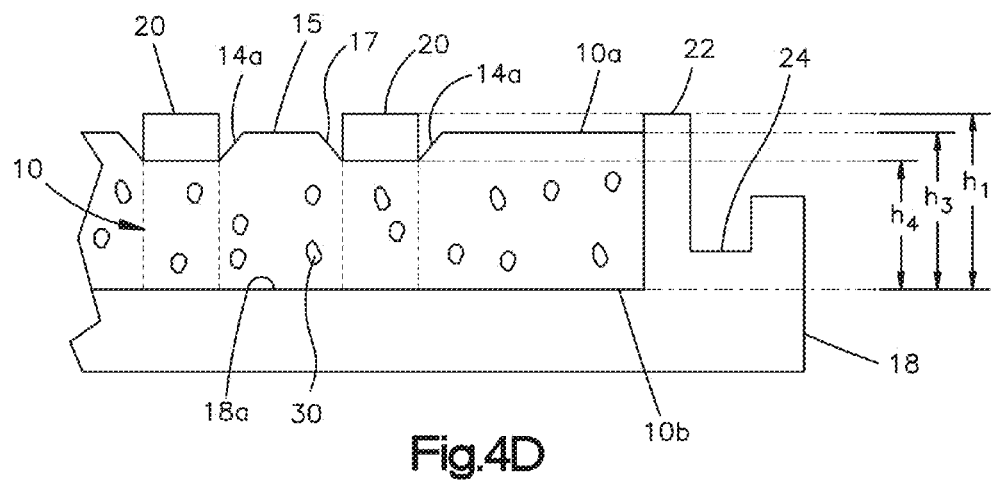
FIG. 4D is a schematic side cross-sectional view of the mold shown in FIG. 4C showing the polymer after being drawn across the mold and solidified to form a polymer film in accordance with another embodiment.
Figure 4E:
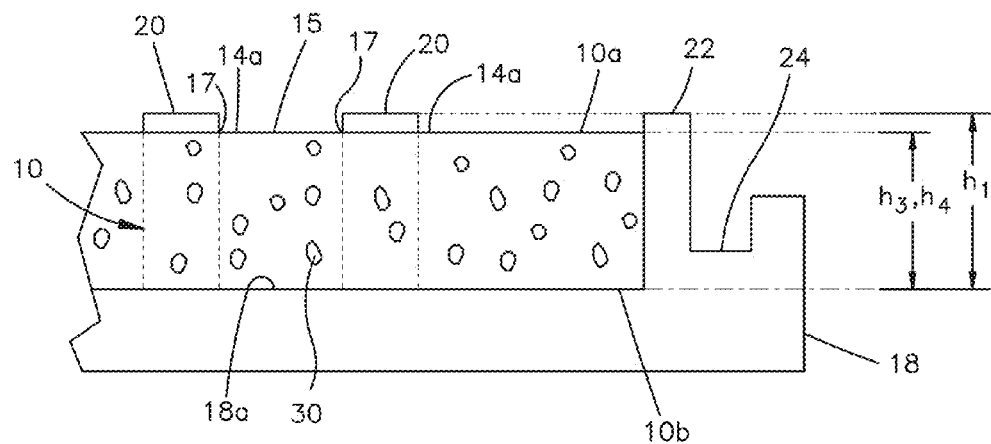
FIG. 4E is a schematic side cross-sectional view of the mold shown in FIG. 4C showing the polymer after being drawn across the mold and solidified to form a polymer film in accordance with yet another embodiment.

Referring to FIGS. 4C-4E, the material that forms the posts 20 can affect the configuration of the solidified meniscus 17 between the apertures 14 and the contiguous planar portion 15, such as the formation of lips 14a around apertures 14. The height of the lips 14a relative to the contiguous planar portion 15 is the difference between $h_4$ and $h_3$, and can be the result of a meniscus of the polymer solution 28 solidifying around posts 20. The meniscus can be defined by the curve in the upper surface of the polymer solution near the posts 20 and is caused by surface tension between the polymer solution 28 and the respective posts 20. The polymer solution 28 can have either a convex or concave meniscus at posts 20. A concave meniscus, which creates the raised lips 14a, can occur when the molecules of the polymer solution are attracted to the material of the posts 20 (commonly known as adhesion) such that the level of the polymer solution is higher around the posts 20 than the solution generally. According to one embodiment, as shown in FIG. 4C, the posts 20 comprise materials configured to cause a concave meniscus in polymer solution, where $h_4$ is greater than $h_3$. Conversely, a convex meniscus occurs when the molecules of the polymer solution have a stronger attraction to each other (commonly known as cohesion) than to the material of the posts 20. According to one embodiment, as shown in FIG. 4D, the posts 20 comprise materials configured to create a convex meniscus in polymer solution where $h_3$ is greater than $h_4$. Thus, it should be appreciated that the meniscuses 17 between the contiguous planar portion 15 and the apertures 14 can be configured as raised lips 14a that extend out from the second surface 10b in the manner described above, or can be configured as depressions that are recessed into the second surface 10b along a direction from the first surface 10a toward the second surface, from the contiguous planar portion 15 to respective ones of the apertures 14. According to a further embodiment as shown in FIG. 4E, the posts 20 comprise materials configured to cause minimal to no meniscus (e.g., substantially no meniscus) of the polymer solution, such that where $h_4$ is substantially equal to $h_3$ at the meniscus 17.

Figure 10:
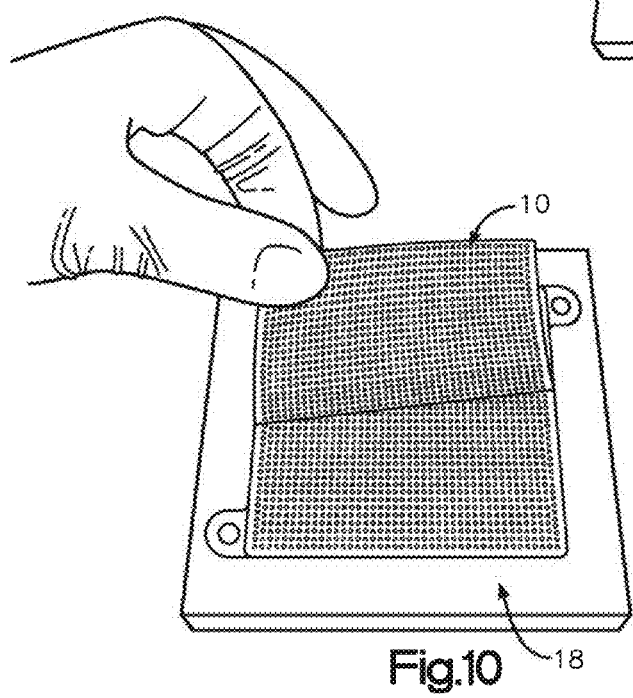
FIG. 10 is a perspective view of the mold of FIG. 8 showing the polymer film being removed from the mold.

Referring to FIG. 10, once the polymer solution 28 is solidified, the film 10 is peeled out of the mold 18, such that the meniscuses formed during the casting of the polymer solution 28 define the solidified meniscuses 17.

Referring to FIGS. 5-7, a method of producing film 10 may include an automated or partially automated casting machine 42. In one embodiment, the automated casting apparatus includes one or more computers 44 having one or more processors and memory (e.g., one or more nonvolatile storage devices). In some embodiments, memory or computer readable storage medium of memory stores programs, modules and data structures, or a subset thereof for a processor to control and run the various systems and methods disclosed herein. In one embodiment, a computer readable storage medium having stored thereon computer-executable instructions which, when executed by a processor, perform one or more of the methods disclosed herein.

The film 10 may be manufactured by alternative methods. In one embodiment, the polymer solution 28 can be cast onto perforated film material with a backing blotter layer, and then the perforated film is removed from the blotter layer, removing the cast solution where there were holes in the casting sheet. One difference with such a process from the above described processes is that, in some embodiments, it does not create a raised lip 14a and apertures 14.

In another embodiment, porous films 10 may also be formed by a lyophilization or freeze-drying method. In one embodiment, a thin solid film of polymer solution is cast in a mold, then the mold chilled to a temperature below the freezing point of the solution, then placed under vacuum to remove the solvent from the film. In some embodiments, this process will also produce fine pores which are much smaller than the apertures 14 described in some of the embodiments above.

In one embodiment, the polymer material used for film 10 can be a crosslinkable prepolymer liquid and urged or drawn to fill the mold and remove excess material in the manner described above, then crosslinked in place by UV radiation, temperature, a catalyst or other means. In one embodiment, this process could produce a very similar final product as described above, except that the final thickness of the cast film 10 can be substantially equal to the depth of the mold, and there would be little or no lip 14*a* around the apertures 14.

In another embodiment, the film 10 can be produced as a thin porous film in a screen printing process. In one embodiment, a layer of solution is screen printed in the final pattern, then dried. In one embodiment, this produces a much thinner layer, however multiple layers of polymer can be screen printed and dried one on top of the other to build up the desired thickness of film 10, which can define a multi-layered film.

In another embodiment, a similar casting process could be performed as described above using a glass plate with a pattern made from a hydrophobic polymer such as silicone, in the shape of the desired apertures. In one embodiment, when a thin layer of polymer solution is cast onto the plate, the surface tension differences between the glass and the patterned polymer cause the solution to concentrate on the glass surface, and pull away from the patterned hydrophobic polymer surface. In one embodiment, the solution is then dried to form a solid film with apertures in the same pattern as the silicone polymer. In one embodiment, this process could also be performed with a crosslinkable prepolymer liquid as described above.

In another embodiment, a thin porous polymer film is made using a two-sided mold, where the polymer solvent solution is injected into the mold, and chilled to solidify the solution. In one embodiment, the mold is then opened and one side removed, leaving the chilled solution in the cavity side. In one embodiment, the chilled solution side is placed into an oven to dry the polymer solution and form a film 10.

According to one embodiment of the disclosure, the film further comprises an adhesive layer, which is biocompatible, and capable of adhesively fixing at least one surface of the film to another surface (e.g. an outer surface of a medical device). In one embodiment, substantially all of the first or second surface of the film, or both has an adhesive layer. In another embodiment, only a portion of the first or second surface of the film, or both has an adhesive layer, for example along the periphery of the first or second surface or both. The adhesive layer can be formed integrally with the film during the solvent casting process. In such a process the adhesive can be applied to the mold and the polymer solution subsequently cast on top of the adhesive layer. Alternatively, the polymer solution can be cast in the mold first and the adhesive layer applied over the polymer. In certain embodiments, the polymer solution itself can comprise the adhesive layer. Of course, where it is desired to have the adhesive applied to both surfaces of the film, the adhesive layer can be applied in both manners. In still yet another embodiment, the film can be solution cast molded and separately have the adhesive layer applied after removal from the mold, for example by dipping, spraying, or coating the adhesive onto the film.

According to one embodiment where the film contains a surface adhesive layer as previously described, a film storage system, for the storage, packaging and/or shipment of the film can include 1) the film containing an surface adhesive layer, and 2) a non-adhesive backing material (e.g., a strip) that can be placed over the surface adhesive layer to protect and shield the adhesive layer until such time as it is desired to adhesively affix the film to the surface of another object, such as, for example, a surface of a medical device or a tissue such as bone. At such time, a user, preferably a surgeon or nurse, can remove the non-adhesive backing material and apply the film as desired. According to another embodiment where the film contains a surface adhesive layer, a film storage system, for the storage, packaging and/or shipment of the film can include 1) the film containing a surface adhesive layer, and 2) a collector where the film can be collected. For example, film 10 can be wound around a collector such as a cylinder and collected and stored in a rolled configuration until such time as it is desired to adhesively affix the film to the surface of a medical device or surface of a tissue. At such time, a user, preferably a surgeon or nurse, can unwind a length of film as identified and cut or otherwise separate the desired length of film from the cylinder and apply the film as desired.

In other embodiments, film 10 can be applied to a desired anatomical site and secured at the site without the use of an adhesive layer, or in conjunction with an adhesive layer. For example in certain embodiments, a film fixation system for film fixation at an anatomical site can include 1) a film and 2) a film fixation element where the fixation element securely affixes the film to the anatomical site, preferably securely affixes the film to a medical device at the anatomical site or to a tissue such as a bone or tendon at the anatomical site. According to one embodiment, the fixation element is a screw, pin, wire, suture, staple, glue, or combinations thereof. In addition, the polymer film (with or without an adhesive layer) may be wrapped around the medical device one or more times. It should be appreciated that in certain embodiments as described above, the adhesive layer of the film can function as the film fixation element. According to still another embodiment, the system for film fixation can be further combined with a medical device to provide a system for treatment, for example a system for fracture fixation including 1) an orthopedic medical device and 2) a film fixation system including a film and a film fixation element.

The different possibilities for affixing the polymer film to the medical device or tissue provides a user with flexibility. In certain of these embodiments, the user can size and shape the polymer as desired or needed and can cover all or part of the medical device surface or tissue with the polymer film. For example, one could selectively affix the polymer film to only a bone-facing surface of the implant.

Referring to FIGS. 2 and 11A-11J, after creating the film 10, the film 10 can be formed into an active biocompatible implant cover 25 configured for placement onto or over a surface of a medical implant. The biocompatible implant cover 25 can be referred to as active in that it includes one or more active agents of the type described herein, alone or in combination, such that when implanted, the active biocompatible implant cover 25 delivers the one or more active agents. The medical implant can be a bone implant, such as an intramedullary nail or a bone plate, or any alternative medical implant (such as an implant for use in orthopedic and/or musculoskeletal repair), the film 10 is shaped and fashioned to generally correspond to conform to the shape of at least a portion or substantially all of the bone plate 12. In some embodiments, at least one film 10 is shaped and fashioned into a cover 25 that can be configured as a sleeve 31 (see FIGS. 11A-11J and 17A-26H) that is configured to receive at least a portion or an entirety of the bone plate 12, or a strip that can be adhesively attached to one or more surfaces of the bone plate 12. It should be further appreciated that one or more surfaces of the sleeve 31 can have adhesive properties so as to adhesively attach to one or more surfaces of the bone plate 12.

Referring to FIGS. 11A-11J and 17A-26H in general, the sleeve 31 includes at least one film 10 that defines a first sleeve portion 31a and a second sleeve portion 31b that is spaced from the first sleeve portion 31a along the transverse direction T. The apertures 14 of the first sleeve portion 31a can be aligned with the apertures 14 of the second sleeve portion 31b, or at least one or more up to all of the apertures 14 of the first sleeve portion 31a can be offset with respect to all others of the apertures of the second sleeve portion 31b along either or both of the lateral and longitudinal directions. The first sleeve portion 31a defines an inner surface 35a and an outer surface 37a opposite the inner surface 35a. Similarly, the second sleeve portion 31b defines an inner surface 35b and an outer surface 37b opposite the inner surface 35b. The inner surfaces 35a and 35b face each other, and the outer surfaces 37a and 37b face opposite each other.

Either or both of the inner surfaces 35a and 35b can be defined by one of the first surface 10a or the second surface 10b, and either or both of the outer surfaces 37a and 37b can be defined by the other one of the first surface 10a or the second surface 10b. It should thus be appreciated that the meniscuses 17 (see, e.g., FIG. 1A) can be disposed at either the inner surface 35a or the outer surface 37a, and can further be disposed at the inner surface 35b or the outer surface 37b. In one embodiment, the first and second sleeve portions 31a and 31b are monolithic with each other, such that the meniscuses 17 are disposed on either both inner 35a and 35b or both outer surfaces 37a and 37b. Because the at least one film 10 of the sleeve 31 is flexible, the sleeve 31 can be iterated between a first closed configuration whereby the first and second sleeve portions 31a and 31b, and in particular the inner surfaces 35a and 35b, are immediately adjacent each other along the transverse direction T such that the sleeve 31 does not define an opening between the first and second sleeve portions 31a and 31b, and a second open configuration whereby the sleeve 31 defines an opening 33 between the first and second sleeve portions 31a and 31b, and in particular between the inner surfaces 35a and 35b. Thus, the inner surfaces 35a and 35b can be referred to as implant facing, or bone plate facing, surfaces.

The opening 33 defined between the first and second sleeve portions 31a and 31b. The opening 33 can be sized so as to define a height in the transverse direction T and a width in the lateral direction A that is at least equal to, and can be greater than, the respective height and width of the bone plate 12 that is received in the opening 33. The opening 33 can have a length along the longitudinal direction L that can be equal to, less than, or greater than, the length of the bone plate 12 such that the opening 33 is sized to receive at least a portion up to all of the bone plate 12. Accordingly, each of the sleeve portions 31a and 31b is configured to cover at least a portion, and up to all, of at least one surface of the bone plate 12.

The sleeve 31 can be configured in any manner as desired. For instance, the film 10 can be created in any manner described herein, and shaped so as to define a shaped film that can correspond to the shape of a preselected bone plate shape that is to be received in the resulting sleeve 31. After the film 10 has been molded, material of the resulting film 10 can be removed so as to define a first shaped film that can correspond to the shape of a preselected bone plate shape. A second shaped film substantially identical to the first shaped film can be created from the same film 10 that defined the first shaped film, or from a separate film 10. For instance, material can be removed from the respective film 10 so as to define the second shaped film. The first and second shaped films 10 can be positioned adjacent each other such that their respective outer peripheries are aligned along the transverse direction T. At least a portion of the outer peripheries of the first and second films can be attached to each other by any one of the attachment methods of the type described herein so as to define a closure 16, such as an attachment or an alternatively configured closure, such that the first shaped film defines the first sleeve portion 31a and the second shaped film defines the second sleeve portion 31b.

The closure 16 can extend about a portion of the periphery 39 of the sleeve 31. For instance, the sleeve 31 can define a front end 39a and a proximal portion 43a that is disposed proximate to the front end 39a, and a rear end that is spaced from the front end 39b along at least the longitudinal direction L (which includes embodiments in which at least a portion of the front and rear ends 39a and 39b can further be spaced from each other along the lateral direction A) and defines a distal end 43b disposed proximate to the rear end 39b. The sleeve 31 can further define first and second sides 39c and 39d, respectively, that are spaced from each other along at least the lateral direction A (which includes embodiments in which at least a portion of the first and second sides 39c and 39d can further be spaced from each other along the longitudinal direction L). The first and second sides 39c and 39d extend between the front and rear ends 39a and 39b, for instance from the front end 39a to the rear end 39b. The ends 39a and 39b in combination with the sides 39c and 39d can define the outer periphery 39 of the sleeve 31. The closure 16 can extend about a portion of the outer periphery 39 so as to define at least one opening 41 at the outer periphery 39 between the first sleeve portion 31a and the second sleeve portion 31b. For instance, the closure 16 can extend along a portion or an entirety of the rear end 39b, a portion or an entirety of one or both of the first and second sides 39c and 39d, and a portion or an entirety of the front end 39a, both alone or in combination. For instance, in one embodiment, the first and second sides 39c and 39d and the rear end 39b are attached, such that the sleeve 31 defines the opening 41 at the front end 39a. Alternatively or additionally, the sleeve 31 can define a second open end at the rear end 39b. Alternatively or additionally, the sleeve can define a third or fourth opening at one or both of the sides 39c and 39d, respectively. One or more of the first, second, third, and fourth openings can be continuous with each other.

When the sleeve 31 is in the open configuration, the opening 41 can be dimensioned such that the bone plate 12 can be inserted into, and removed from if desired, the opening 41 and into and out of the opening 33. Alternatively, the bone plate 12 can be placed between the first and second sleeve portions 31a and 31b, and a substantial entirety of the periphery of the sleeve 31 can define the closure 16, such that the bone plate 12 is disposed in the opening 33 and substantially encapsulated by the sleeve so as to be non-removable from the film, meaning that the sleeve 31 does not define an opening at the outer periphery 39 that is sized sufficiently for the bone plate 12 to be removed from the sleeve 31 without breaching either of the sleeve portions 31a and 31b or the closure 16. It should be appreciated that when the bone plate 12 is disposed in the opening, the first and second sleeve portions 31a and 31b cover at least a portion of respective opposed surfaces of the bone plate 12.

In accordance with one embodiment, either or both of the outer periphery 39 of the sleeve 31 and an outer periphery of the opening 33, such as can be defined by the inner periphery of the closure 16 or other closure, can extend parallel to an outer periphery of the bone plate 12, such that the sleeve 31 can define a sheath. Thus, it should be appreciated that the closure has an inner boundary that defines an outer periphery of the opening 33, and at least a portion up to all of the inner boundary can be parallel to the outer periphery 39 of the sleeve 31. It should be appreciated that the at least one film 10 can be shaped in any suitable manner as desired so as to define the sleeve 31. For instance, as described, two shaped films can be adjoined to define the first and second portions of the sleeve 31a and 31b. The first and second shaped films can be produced by cutting a respective one or two molded films 10. Alternatively, the cavity of the mold can be shaped so as to define the outer periphery 39 of the sleeve 31, and the as-molded film can be removed from the mold and thus define the shaped film. Alternatively still, the films 10 can be attached in the manner described herein such that the inner periphery of the closure 16 is sized and shaped such that the resulting opening 33 is sized to receive a plurality of differently shaped bone plates 12 and the inner periphery of the closure 16 does not extend parallel to the outer periphery of the bone plate 12.

As described above, the sleeve 31 can include a closure 16, such as an attachment or alternatively configured closure as desired. For instance, a single film 10, which can be shaped as desired, can be folded about itself along a fold, such that the film defines the first and second portions 31a and 31b of the sleeve 31 that are separated from each other by the fold. Thus, the fold can be said to define a closure at a portion of the outer periphery 39 of the sleeve 31. The fold can be disposed, for instance at a midline of the film 10, such that the film 10 defines two symmetrical regions separated from each other by the fold. The fold can define a fold line, or the film 10 may be shaped into a cylinder and the two opposed edges of the film that are opposite the fold can, in combination, define one of the sides of the sleeve 31. Resulting open portions of the outer periphery 39 of the sleeve 31 can be left open as desired, or closed, for instance attached in the manner disclosed above. Thus, the folded film 10 can be at least partially attached to itself. For instance, the free ends of the film 10 can be attached to each other so as to define an attachment at one of the first and second sides 31c and 31d of the sleeve 31, and the fold can define the other of the first and second sides 31c and 31d. Thus, the sleeve 31 can include a closure 16 at both the first and second sides 31c and 31d. In one embodiment, the second surface 10b overlaps the first surface 10a at the opposed edges of the film 10 such that the first surface 10a defines the inner sleeve surfaces 35a and 35b at the opposed edges of the film 10 so as to define at a least a region of the closure 16 when the opposed edges of the film 10 are attached to each other. Alternatively, the first surface 10a overlaps the second surface 10b at the opposed edges of the film 10 such that the second surface 10a defines the inner sleeve surfaces 35a and 35b at the opposed edges of the film 10 so as to define a least a region of the closure 16 when the opposed edges of the film 10 are attached to each other. The two symmetrical regions of the film 10 can be shaped so as to correspond to the preselected bone plate shape, for instance by removing material of the film 10 or by contouring the mold cavity in the manner described above.

It should be appreciated that in some embodiments, the closure 16, such as the attachment, can be visible through at least one of the first and second sleeve portions 31a and 31b as illustrated in FIGS. 11A, 11B, 11D, and 11E, or can be hidden by the first and second sleeve portions 31a and 31b, for instance as illustrated in FIGS. 11C and 11F-11J. Accordingly, those embodiments in which the closure 16, such as the attachment, is visible can be constructed such that the closure 16, such as the attachment, is hidden, and thus the outer periphery can be illustrated as shown in FIGS. 11C and 11F-11J. Conversely, those embodiments in which the closure 16, such as the attachment, is hidden can be constructed such that the closure, such as the attachment, is visible, and thus the outer periphery 39 can be illustrated as shown in FIGS. 11A, 11B, 11D, and 11E.

Referring now to FIGS. 11A-11J and FIGS. 17A-26H, the sleeve 31 can define any suitable size and shape as desired. For instance, the sleeve 31 can be constructed as any suitable sized and shaped sheath as desired that is configured to form fit the bone that is to be received in the respective opening (such that the inner periphery of the closure 16 is substantially parallel to the outer periphery of the bone plate 12). As illustrated in FIGS. 11A-11C and 17A-19H, the sleeve 31 can define a cross-sectional dimension at the proximal portion 43a along the lateral direction A that is greater than the cross-sectional dimension of the sleeve 31 at the distal portion 43b along the lateral direction A. For instance, at least one of the sides 31c and 31d can define a flared region 45 that extends laterally out from an adjacent region of the respective side as it extends along a direction from the rear end 39b toward the front end 39a, and thus is flared along the lateral direction A away from the opposed side with respect to the adjacent region of the respective side as it extends along a direction from the rear end 39b toward the front end 39a. The flared region 45 of one of the sides 31c and 31d can extend laterally out further or an equal amount (see FIGS. 11H, 11I and 24A-25H), with respect to the flared region 45 of the opposed side. Further, the flared region 45 of one of the sides 31c and 31d can define the same shape (see FIGS. 11H, 11I and 24A-25H) or a different shape with respect to the flared region 45 of the opposed side. In accordance with the illustrated embodiment at FIGS. 11A and 17A-H, the flared region 45 at the second side 39d extends laterally out further than the flared region at the first side 39c. Thus, it should be appreciated that a portion of the front end 39a is offset with respect to the rear end 39b along the lateral direction. Either or both of the front end 39a and the rear end 39b can be curved (e.g., convex as illustrated or concave as desired) or straight as desired in all embodiments, unless otherwise indicated. In accordance with the illustrated embodiment at FIGS. 11B, 11C, 18A-18H, and 19A-19H, the second side 39d includes the flared region 45 and the first side 39c is linear from the front end 39a to the rear end 39b. Referring now to FIGS. 11D-11G and 20A-23H, both the first and second sides 39c and 39d can extend linearly and parallel to each other from the front end 39a to the rear end 39b. The rear end 39b can be curved or straight as desired. The length of the sleeve 31 can be any dimension as desired from the front end 39a to the rear end 39b along the longitudinal direction L. Similarly, the width of the sleeve 31 can be any dimension as desired from the first side 39c to the second side 39d along the lateral direction A. Referring to FIGS. 11J and 26A-H, the flared region 45 at one of the sides 39c and 39d can extend laterally inward toward the other one of the sides 39c and 39d, and the flared region 45 at the other one of the sides 39 can extend laterally outward. For instance, as illustrated, the proximal end 43a of the first side 39c can extend laterally inward toward the second side along a direction from the rear end 39b toward the front end 39a. The proximal end 43a of the second side 39d can extend laterally outward away from the first side 39c along a direction from the rear end 39b toward the front end 39a. Moreover, the flared region 45 can extend to a location spaced from the front end 39a along a direction from the front end 39a toward the rear end 39b, such that a length of the proximal portion 43a that extends between the flared region 43 and the front end 39a extends parallel to an adjacent region of the respective side, such as side 39*d*, that is disposed adjacent the flared region 45.

As described above, the active biocompatible implant cover 25 can be configured as a sleeve, such as any sized or shaped sleeve 31 as desired, which can define a sheath, or the implant cover 25 can be alternatively configured as desired. For instance, the implant cover 25 can be configured as one or more strips of the film 10 that are configured to overlay at least a portion of one or more surfaces of the bone plate 12. The strips can be shaped as described above such that the outer periphery of the strips is substantially aligned with, or parallel to, the outer periphery of the bone plate 12, or can be sized greater than the bone plate 12 or less than the bone plate 12. Thus, the strips can define any size and shape as desired, for instance the shapes as illustrated in FIGS. 11A-11J and FIGS. 17A-26H with respect to the sleeve 31, or any alternative shape as desired. The strips can further be sized greater than the sizes of the sleeves 31 illustrated in FIGS. 11A-11J and FIGS. 17A-26H, or less than the sizes of the sleeves 31 as illustrated in FIGS. 11A-11J and FIGS. 17A-26H. Thus, one or more of the strips can be placed along a portion up to all of the bone facing surface of the bone plate 12, a portion up to all of the outer surface of the bone plate 12 that is opposite the bone facing surface, or both. The strip can define an inner surface that faces the bone plate 12, and an outer surface that faces away from the bone plate 12. The inner surface of the strip can be defined by the first surface 10*a* or the second surface 10*b*. Conversely, the outer surface of the strip can be defined by the first surface 10*a* or the second surface 10*b*.

In one embodiment, the strips can be sized so as to wrap around the bone plate 12, for instance at least one-half of a revolution about the bone plate 12 such that the strip overlays at least a portion of the bone facing and outer surfaces of the bone plate 12. The strip can be wrapped around the bone plate 12, as many full revolutions as desired until the strip overlays a sufficient area of one or both of the bone facing and outer surfaces of the bone plate 12 as desired. The strip can be dimensioned as desired, for instance by removing material from the as-molded film 10, or by contouring the mold cavity to define a desired size and shape of the strip.

As described herein, at least a portion of film 10 or films 10 can be attached to each other by attachment methods to define a closure 16, such as an attachment. In certain embodiments, the attachment can be defined by attachment components, such as a seam, glue, sutures, staples, pins, wires, screws, heat, ultraviolet light, or a combination thereof that attach a first region of film to a second region of film that overlaps the first region of film, for instance along the transverse direction T. Accordingly, two regions of the same film or two separate films may be attached to form a sleeve 31. For example, first and second films 10 can be positioned adjacent each other such that a first region of film, which can be defined by the first film 10, overlaps with a second region of film, which can be defined by the second film 10. The first and second regions of film can overlap along any direction as desired, such as the transverse direction T. The overlapping first and second regions of film can be attached to each other with one of the attachment components. Alternatively, a single film 10 can be formed into a sleeve by folding the film 10 so as to at least partially define a closure 16, and contouring the single film such that free ends overlap. Thus, the free ends of the single film 10 can define the first and second overlapping regions of film. The overlapping first and second regions of film, whether monolithic with each other and defined by the same film 10, or defined by different films 10, can be attached to each other by applying any of the above described attachment components to one or both of the first and second overlapping regions of film so as to at least partially define a closure 16. For instance, a glue can be applied along one or both surfaces of the overlapping first and second regions of film that face each other, and the surfaces can be brought against each other and/or the glue. In another embodiment, the attachment can be defined by applying heat and/or pressure to the first and second overlapping regions until the regions of film begin to soften (or melt) and integrate with one another, and subsequently allowing the portions to re-solidify. In addition, multi-film sleeves and strips may be prepared by attaching two separate films that are immediately adjacent each other, for instance in the transverse direction T.

In addition to sleeves 31, film 10 may be used, in some embodiments, for other medical applications such as hernia repair mesh, adhesion barrier, soft tissue augmentation, filtration membranes, drug delivery membranes, bone graft containment (e.g., for maintaining bone graft in place for example in a spinal fusion procedure, or segmental defect grafting in a long bone), or wound care products such as bandages.

The polymer film may be used at any surgical site susceptible to microbial infection. Such methods can be used with any polymer film embodiment and/or combination of embodiments disclosed herein. Typically, the methods comprise identifying a surgical site in need of microbial inhibition and contacting the surgical site with a polymer film comprising an active agent. The methods may also involve identifying a zone at a surgical site or on a medical implant needing microbial inhibition (zone of inhibition), contacting the medical implant with the polymer film, and implanting the medical implant at the surgical site. In certain embodiments, the polymer film is used in conjunction with medical implants comprised of material that is susceptible to bacterial colonization, for example, implants comprising metal.

The polymer film may be used in conjunction with metal bone plates to be implanted at fracture sites in the extremities, particularly the lower extremities, such as fractures associated with the femur, fibula, and tibia. Following implantation, the bacterial growth at the surgical site may be monitored to determine the effectiveness of the treatment.

The implant may be contacted with the film in any manner as described herein. For example, the film may be in the form of an implant cover configured for placement onto or over a surface of a medical implant. In the case of a sleeve, the polymer film is slipped over at least a portion of the implant. As described herein, the sleeve can include at least one open end, and in certain embodiments two open ends. Alternatively, the polymer film may be adhered or affixed to the implant via adhesive or fixation devices such as sutures, screws, or other types of fasteners. Typically, a doctor will select an implant with the proper contour, such as a bone plate, to treat the bone fracture at issue. In the case of percutaneous procedures, and before implant fixation, a cavity within the soft tissue may be prepared to reduce the stresses on the polymer film during implant insertion.

The contacting of the polymer film and implant is typically done at or near the time of surgery, i.e., intraoperatively, such that the surgeon can match the polymer film with the medical implant to be contacted based on size and shape and the drug requirements for the subject patient. If the implant is in the form of a sleeve, the sleeve may be applied by opening it and inserting the implant, such as a bone plate, until the anatomic portion of the plate is seated in the sleeve. The sleeve may cover the entire implant or a portion of the implant. For example, the sleeve may be trimmed and/or folded to conform to the implant as desired. Prior to instrumentation attachment or screw/fastener insertion of the medical implant at the surgical site, the polymer film may be pierced through the holes in the implant that will be used during final implant fixation. This will provide an unimpeded path for the screw/fastener through the polymer film. The implant may then be affixed using standard surgical procedures.

Total drug dosing of the polymer film is a function of the size of the implant as well as surgical need. In one embodiment, the polymer film contains approximately 0.6 mg of gentamicin sulfate per square centimeter of surface area. The total dose of drug delivered depends on the size of the polymer film and the implant it is designed to contact. In certain embodiments, a surgeon will determine the amount of antibiotic that is needed at a surgical site of a particular patient. The polymer film may then be manipulated to meet the delivery need. For example, if the patient requires more antibiotic than is available in a single polymer film, multiple polymer films may be used and/or longer or otherwise larger films may be selected. To the extent the polymer film is in the form of a sleeve, an implant may be fitted with multiple sleeves. If the patient requires less antibiotic, the polymer film may be reduced by, e.g., cutting or trimming. As indicated herein, the surgeon may determine an appropriate zone of inhibition that will prevent bacterial colonization on an implant even if the polymer film is not contacting the entire surface area of the implant, such that cutting or trimming the polymer film may reduce the overall drug load, but not reduce the effectiveness of the anti-microbial treatment.

In one embodiment, there is an initial release of 20% of the drug content in the film within one hour of implantation. This is followed by a sustained release of the remaining drug content for approximately 7 to 10 days. The polymer film itself is completely degraded by hydrolysis and absorbed by the body within 60-90 days of implantation.

In the case of gentamicin, gentamicin-related nephrotoxicity is related to duration of treatment, and is typically transient although full functional recovery may not occur for several months after therapy stops. Nephrotoxicity is also related to plasma gentamicin levels, with recommended trough levels not to exceed 2.0 µg/ml. Peak plasma gentamicin levels released from the polymer film have been found to be well below this level in sheep studies, including in the range of 0.1 ug/ml. Local administration of gentamicin may be particularly advantageous as compared to systemic antibiotic treatments. According to one embodiment, local delivery of gentamicin provides a higher concentration of antibiotic at a surgical site than a comparable standard of care amount of systemic antibiotic treatment, thus permitting a higher potential for eliminating bacterial growth at the site. According to another embodiment, local delivery of gentamicin provides a lower plasma concentration than a comparable standard of care amount of systemic antibiotic treatment, thus potentially reducing potential adverse effects, for example nephrotoxicity, that can result from systemic antibiotic treatments. Thus, local delivery provides an opportunity to deliver higher concentration of antibiotics with an overall smaller quantity than systemic treatments.

In one embodiment, the method of inhibiting microbial infection at a surgical site comprises contacting a medical implant with a polymer film of the present disclosure at or near the time of surgery, wherein the film comprises a drug component having a particle size of 10 microns or less, and implanting the medical implant at the surgical site. As described herein, with respect to bacteria, the polymer film is able to produce a 5 to 7-log reduction of colony forming units.

In more particular embodiments of the method, the polymer film is in the form of a sleeve and comprises a bioresorbable film comprising a copolymer of glycolide, trimethylene carbonate, lactide and caprolactone, the active agent is gentamicin sulfate, and the surgical site is a bone fracture site of the lower extremities, such as the tibia.

Example 1

Film preparation: Films were produced from a copolymer of approximately: 70% glycolic acid, 17% caprolactone, 5% lactic acid and 8% trimethylene carbonate (US Surgical, North Haven, Conn.). This copolymer was dissolved in dimethyl sulfoxide (DMSO) at a concentration of 20% by weight, and either cast as a thin film onto a 20 cm×20 cm glass plate, or mixed with 5% or 10% gentamicin sulfate and then cast. Cast films were dried in air at 60° C. for a minimum of 12 hours to remove solvent, then removed from the glass plate and stored under vacuum for further testing. Finished films had a thickness of 0.06±0.01 mm.

Figure 12:
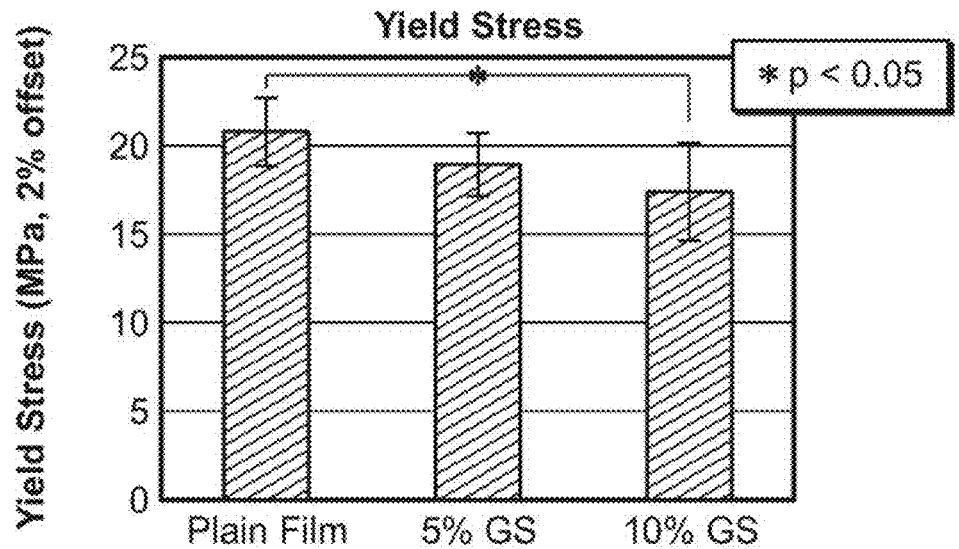
FIG. 12 is a yield stress graph of a polymer film in accordance with an exemplary embodiment of the present disclosure.
Figure 13:
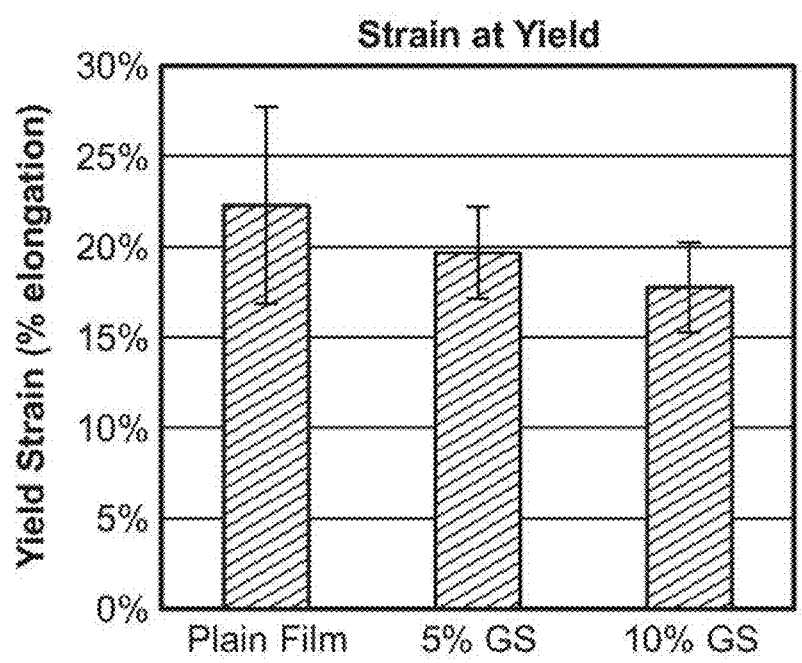
FIG. 13 is a strain at yield graph of a polymer film in accordance with an exemplary embodiment of the present disclosure.

Tensile testing: 10 mm×80 mm strips cut from the cast films were tested in tension to failure on an Instron test stand (model 3342) at 20 mm/sec, dry and at room temperature, per ASTM D882. Initial yield stress of the films tested at t=0 are shown in FIG. 12 and the elongation of the films at yield are shown in FIG. 13. Incorporation of gentamicin sulfate into the films results in a minor decrease in tensile strength and elasticity.

Figure 14:
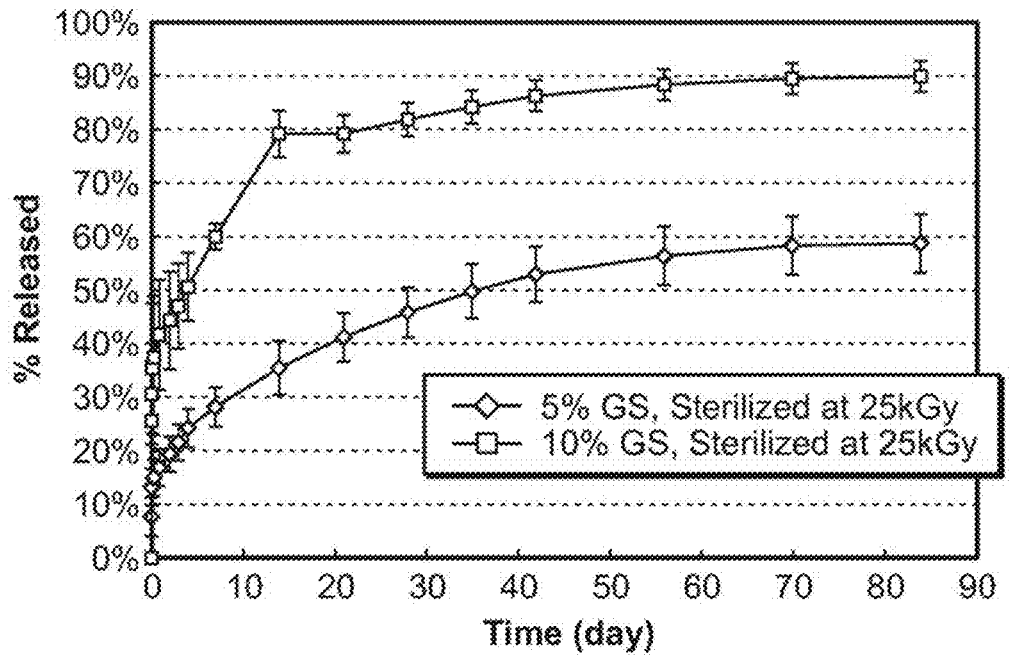
FIG. 14 is a graph illustrating the rate of drug release over time when a sleeve in accordance with an exemplary embodiment of the present disclosure is placed into saline solution.

Drug release testing: 19 mm diameter disk samples cut from cast films (5% & 10% gentamicin) were placed in PBS at 37° C. Concentration of gentamicin in solution was measured at 15 min, 30 min, 1 hr, 2 hr, 4 hr, 6 hr, 1 d, 2 d, 4 d, 7 d and weekly up to 12 weeks, using fluorescence polarization immunoassay technique (TDxFLx, Abbott Laboratories). Results are shown in FIG. 14.

Figure 15:
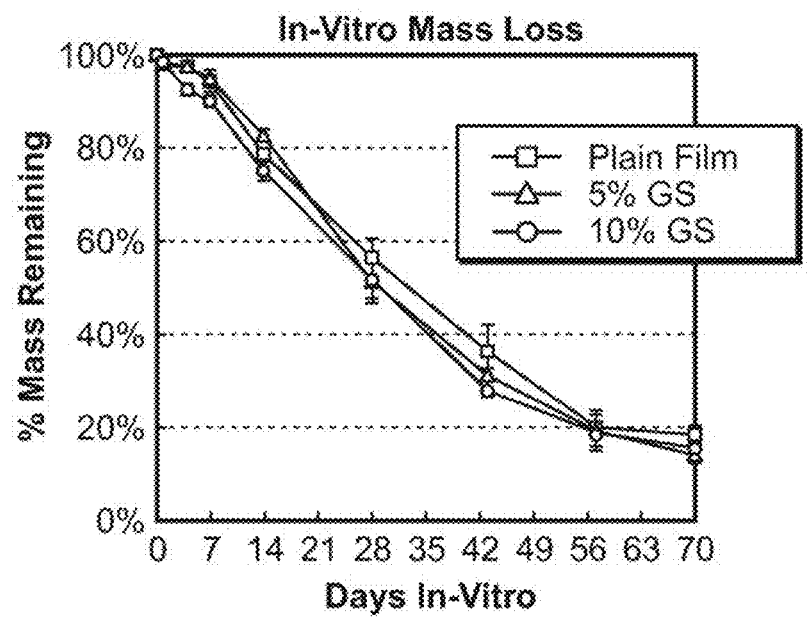
FIG. 15 is an in-vitro mass loss graph of a polymer film in accordance with an exemplary embodiment of the present disclosure.
Figure 16:
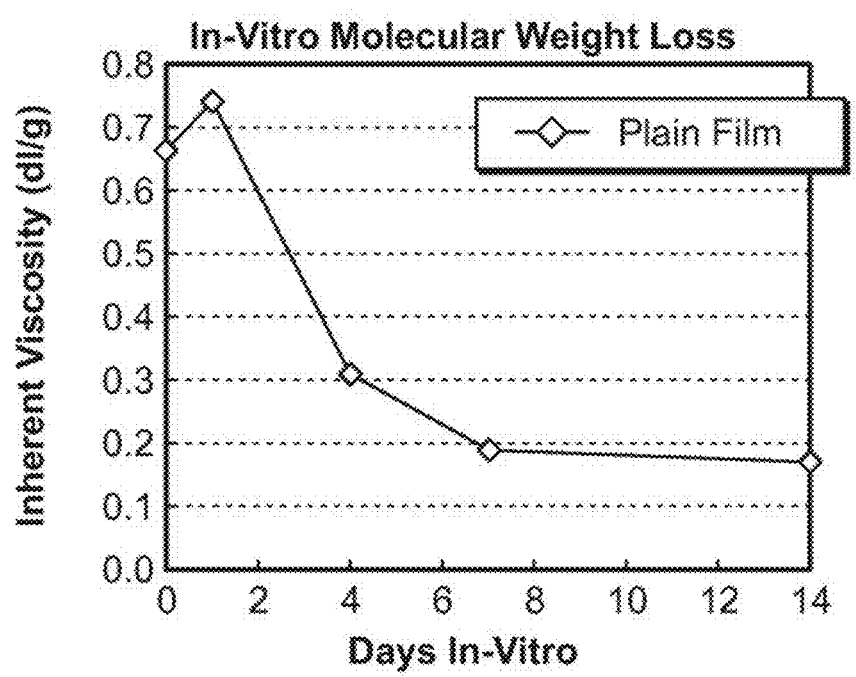
FIG. 16 is an in-vitro molecular weight loss graph of a polymer film in accordance with an exemplary embodiment of the present disclosure.
Figure 21C:
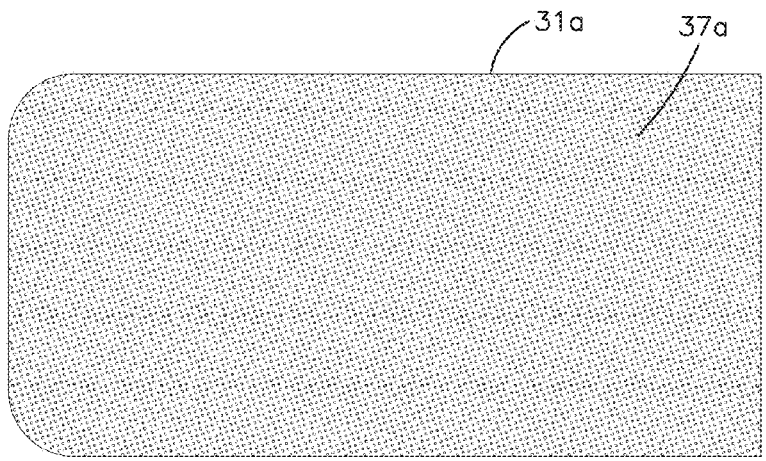
FIG. 21C is a top plan view of the sleeve illustrated in FIG. 21A.
Figure 21D:
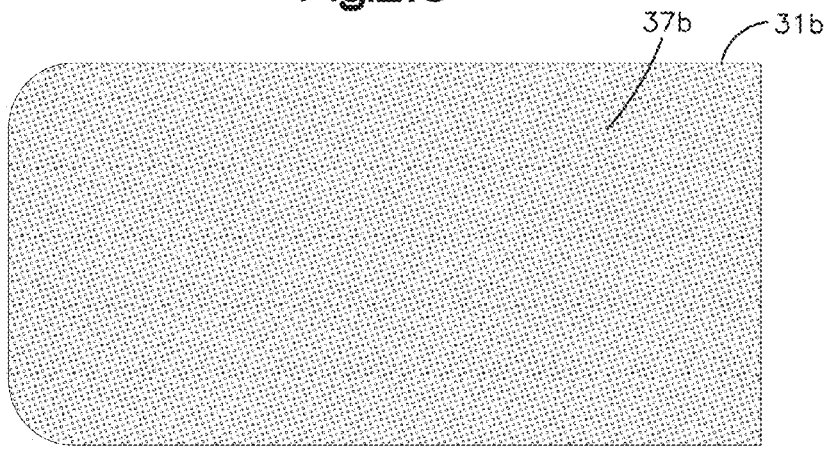
FIG. 21D is a bottom plan view of the sleeve illustrated in FIG. 21A.
Figure 21E:
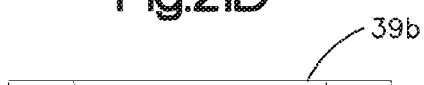
FIG. 21E is a rear elevation view of the sleeve illustrated in FIG. 21A.
Figure 21F:
FIG. 21F is a front elevation view of the sleeve illustrated in FIG. 21A.
Figure 21G:
FIG. 21G is a right side elevation view of the sleeve illustrated in FIG. 21A.
Figure 21H:
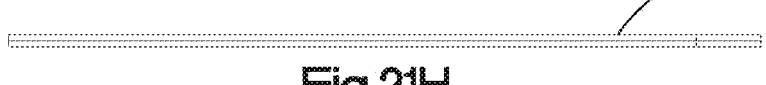
FIG. 21H is a left side elevation view of the sleeve illustrated in FIG. 21A.

In-vitro degradation: 19 mm diameter disk samples cut from cast films (plain, 5% gentamicin, 10% gentamicin) were weighed and placed into vials containing phosphate buffered saline solution (PBS) at 37° C. for 1 d, 4 d, 7 d and weekly up to 10 weeks. Fresh PBS was changed weekly and the pH was monitored. At test times, the samples were removed from the solution, freeze dried, and weighed. The inherent viscosity of each sample was also measured by dilute solution viscosity (Cannon-Ubbelhode semi micro viscometer, in HFIP at 25° C.). In-vitro degradation of all polymer films proceeded at a similar rate, regardless of the level of incorporated gentamicin, as shown in FIG. 15. Molecular weight of the polymer as measured by inherent viscosity dropped rapidly within the first 7 days in-vitro, then at a slower rate, as shown in FIG. 16.

Example 2

In one exemplary embodiment, implants were tested by implantation in sheep. The implants were metal plates with tubular, thin (0.05-0.08 mm), transparent polymer sleeves carefully slipped over the metal plates just before they were surgically inserted and attached to the bone. The sleeves had a tight fit, covered the metal plates completely over the entire length, although they were open at both ends of the plates. The sleeves were comprised of a synthetic copolyester (glycolide, caprolactone, trimethylenecarbonate, lactide) with aperture holes of 1.5 mm diameter equally spaced throughout. One group of sleeves contained triclosan (2,4,4'-trichloro-2'-hydroxydiphenyl ether) at a concentration of 1%, one group of sleeves contained gentamicin at a concentration of 10%, and one group of sleeves contained a combination of both triclosan (1%) and gentamicin (10%). The concentration of gentamicin and Triclosan were chosen based on in vitro testing to determine the therapeutic window for each compound.

The hydrophobic triclosan was in complete solution within the polymer, in contrast to the hydrophilic gentamicin, which remained suspended as 10-20 μm small particles. In vitro testing has shown that due to its poor water solubility, triclosan is released from these films only slowly over a to 3 weeks period, with minimal initial burst release.

Approximately 50% of the more water soluble gentamicin which is exposed to the surface of the sleeves was released into the adjacent tissue within 24 hours after insertion. The remaining gentamicin encapsulated in the depth of the polymer dissolves more slowly and was released over a 2 to 3 week period after implantation. The polymer was designed to degrade through hydrolysis within 60 days after surgery.

The sleeves with or without antimicrobial agents were proven biocompatible, with minimal effect on soft tissue and bone healing and not corrosive to the metallic implants. Additional details of the experiment can be found in Vet Surg. 2012 Jan. 12. *Biodegradable Sleeves for Metal Implants to Prevent Implant-Associated Infection: An Experimental In Vivo Study in Sheep.* von Plocki S C, Armbruster D, Klein K, Kampf K, Zlinszky K, Hilbe M, Kronen P, Gruskin E, von Rechenberg B., which is hereby incorporated by reference in its entirety.

Example 3

In one exemplary embodiment, film 10 is manufactured by the following method:

Determination of Gentamicin Moisture Content:

The moisture content of gentamicin sulfate powder is measured by a loss on drying method. Approximately 0.5 grams of gentamicin is weighed in a glass jar, then heated under vacuum to 110° C. for 3 hours and weighed a second time. The weight loss is recorded as the moisture content, which is used to calculate the percent moisture.

Solution Mixing:

14.69 grams of gentamicin sulfate powder is weighed, compensating for the percent moisture content as calculated above. This is mixed into 400 g of DMSO solvent in a 1 L vessel, using a paddle mixer. The mixture is stirred for 30 minutes until the gentamicin is uniformly distributed. 100 g of a copolymer containing glycolic acid, caprolactone, lactic acid, and trimethylene carbonate monomers is added to the suspension, and the mixing vessel is heated to 65° C. Mixing is continued for 2 hours until the polymer is completely dissolved into the solution, then the solution temperature is reduced to 55° C.

Film Casting & Solvent Drying:

A casting mold and drawing blade made from high density polyethylene are used to cast thin perforated films from the polymer solution. The casting mold and drawing blade are pre-cleaned using an alkaline detergent solution and loaded into an automated CNC casting fixture. 15 ml of the polymer solution are drawn up in a polypropylene syringe, which is loaded into the casting fixture. The casting fixture automatically dispenses the solution onto the casting mold, and draws the blade across the surface of the mold. The mold filled with polymer solution is placed into a solvent drying oven at 85° C. for approximately 90 minutes to dry the film. The molds are removed from the drying oven and the films are peeled from the molds within 2 minutes.

Sleeve Sealing:

An impulse heat sealing press with specially shaped dies is used to seal and cut the cast film into the shape of a sleeve. Two cast films are placed into the press, and the press is closed with a pressure of 80 psi and heated to 200° C. for 4 seconds. The sleeves are removed from the excess film material and cut to the appropriate length. Sealed sleeves can be dried under vacuum at 50° C. and sealed in moisture barrier packaging to prevent degradation of the bioresorbable polymer.

Example 4

In vitro studies have been conducted to evaluate the effectiveness of a gentamicin containing resorbable polymer film to prevent colonization of metal implants by common bacterial pathogens. Colonization assays using agar to simulate soft tissue coverage of stainless steel and titanium fracture fixation plates have shown that the film is effective in preventing bacterial colonization of the metallic implants by *Staphylococcus aureus, Staphylococcus epidermidis, Pseudomonas aeruginosa* and *Enterobacter cloacae*. These data represent at least a 5 to 6-log reduction in bacterial counts compared to metallic implants with no film (control).

Figure 27:
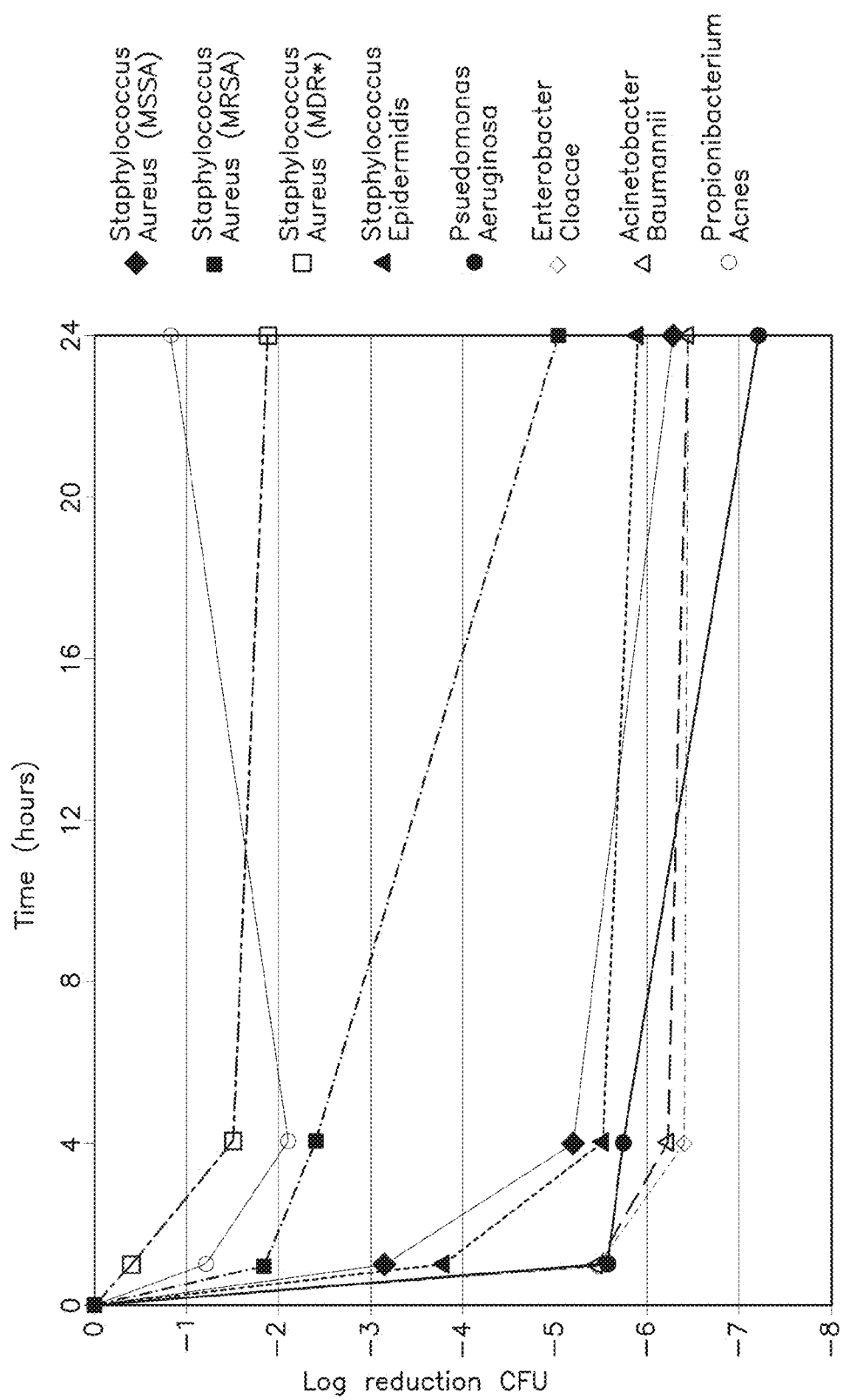

In time to kill assays, stainless steel plates were inoculated with bacteria. The gentamicin sulfate containing film was then placed on the plate and the number of surviving bacteria were measured at different time points. Time to kill data for target bacteria are shown below. The gentamicin film was effective to produce a 5 to 7-log reduction in bacterial colonization—measured as "colony forming units" (CFU)—by all Gram positive (shown in blue: *Staphylococcus aureus* (MSSA), *Staphylococcus aureus* (MRSA), *Staphylococcus aureus* (MDR) and *Staphylococcus epidermidis*) and Gram negative (shown in green: *Pseudomonas aeruginosa, Enterobacter cloacae*, and *Acinetobacter baumannii*) target bacteria, except for a multi-drug resistant strain of *S. aureus*, and the anaerobe *P. acnes*, both of which are typically gentamicin resistant. FIG. 27 illustrates the effectiveness of the gentamicin sulfate containing film in preventing colonization of stainless steel in vitro (various bacteria per ISO 22916)

Example 5

The objective was to measure the zone of inhibition of a gentamicin film. Testing was performed with 4 different species of bacteria.

Samples 6 mm punches of the gentamicin film (0.1%, 0.5%, 1.0%, 5.0%, and 13% gentamicin sulfate, anhydrous) (the 13% gentamicin film was tested separately from the other gentamicin films and the data was separately collected and produced)

Controls blank filter disk w/120 ug Gentamicin in 30 ul dPBS; blank filter disk in 30 ul dPBS Bacteria

*S. aureus* ATCC 25923; *S. epidermidis* ATCC 12228; *Pseudomonas aeruginosa* ATCC 10145; *Enterobacter cloacae* ATCC 29941

Materials & Instrument

Glass culture tubes (VWR #:89001-480); Blank Disks, 6.35 mm diameter (VWR#: 90002-114); 6 mm Disposable Biopsy Punches (VWR#: 21909-144); Mueller Hinton agar dishes (VWR #: 100219-188); 0.5 McFarland turbidity standard (VWR #: 29447-318); dPBS (VWR #: 12001-664); Cotton swabs; Incubator; Thermometer; Bacterial hood Experimental Method Add colonies from an agar dish which was incubated o/n at 36° C. to dPBS.

Adjust turbidity with dPBS to 0.5 McFarland Standard equivalent.

Within 15 minutes of adjusting turbidity, dip a sterile cotton swab into the dPBS. Swirl the swab in this tube and when removing the swab, press it into the side of the tube above the liquid.

Inoculate Mueller-Hinton agar plates by streaking once down the middle of the plate. Then streak the swab all over the plate; rotate 2×'s~60° each time. After streaking the entire plate, streak the swab around the rim of the plate.

Place filter disks/punches onto the dish.

Place in the 36° C. incubator within 15 minutes inoculating dish.

Incubate 16-18 hours.

Figure 28:
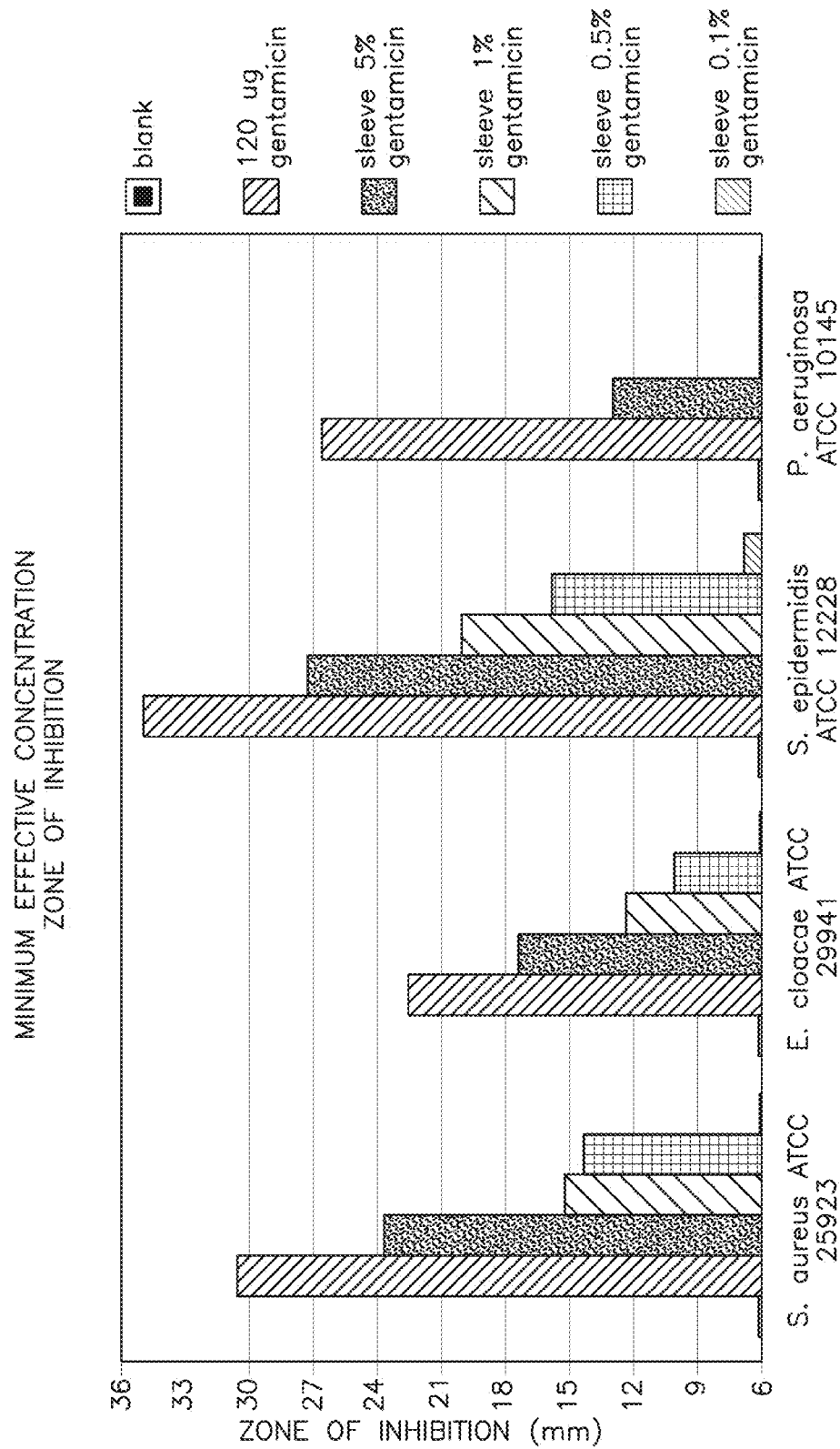

Measure ZOI in millimeters using slide caliper (ZOI was measured a linear distance measured through the center point of the disk). FIG. 28 illustrates the minimum effective concentration and measured ZOI.

| | Avg. ZOI (mm) | | | |
|---|---|---|---|---|
| | S. aureus | E. cloacae | S. epidermidis | P. aeruginosa |
| Blank | 0.00 | 0.00 | 0.00 | 0.00 |
| 120 ug gentamicin | 30.5 | 22.4 | 34.9 | 26.7 |
| 5% gentamicin | 21.2 | 17.4 | 27.2 | 12.9 |
| 1% gentamicin | 15.1 | 12.3 | 19.8 | 0.0 |
| 0.5% gentamicin | 13.4 | 10.0 | 15.7 | 0.0 |
| 0.1% gentamicin | 0.0 | 0.0 | 6.7 | 0.0 |

| | Avg. ZOI (mm) | | | |
|---|---|---|---|---|
| | S. aureus | E. cloacae | S. epidermidis | P. aeruginosa |
| Blank | 0.00 | 0.00 | 0.00 | 0.00 |
| 120 ug gentamicin | 28.73 | 25.27 | 31.37 | 24.90 |
| 13% gentamicin | 25.80 | 22.40 | 29.87 | 20.33 |

Example 6

Figure 29:
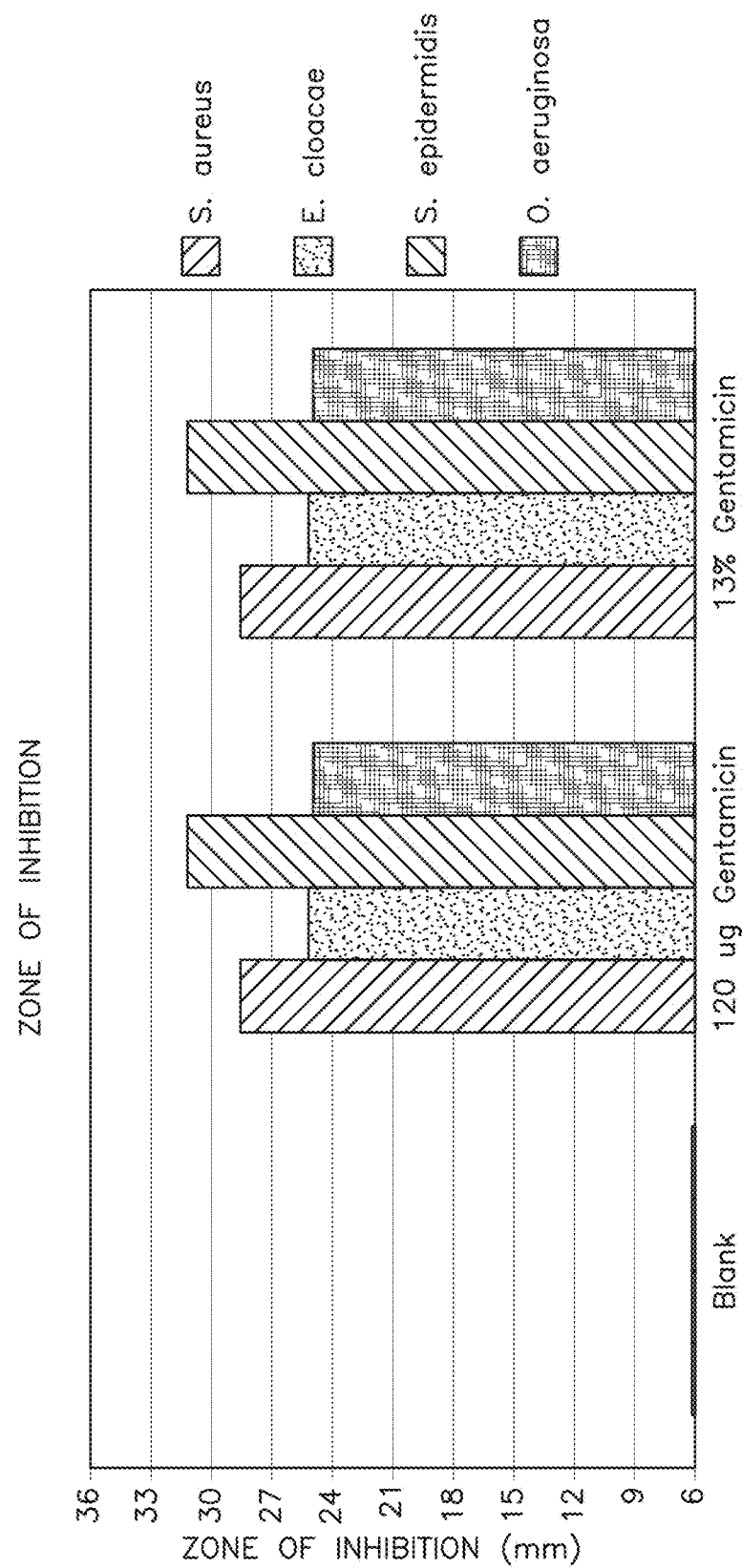

In order to evaluate the effectiveness of a gentamicin sulfate containing polymer film to prevent bacterial colonization, stainless steel fracture fixation plates were covered with gentamicin sulfate containing polymer films in the form of sleeves or sleeves that were too short to cover the full plate, i.e., only half of the plate (5.5 cm of the 11 cm long plate) was covered. These plates were inoculated with bacteria and evaluated for antimicrobial activity in a 3-dimensional agar assay which simulates soft tissue coverage Four common pathogens (*P. aeruginosa*, *S. aureus*, *E. cloacae*, and *S. epidermidis*) were evaluated, and the gentamicin sulfate containing polymer film (13% by weight gentamicin) effectively prevented colonization of the steel plates, even those surfaces of the plates not covered by the polymer film (5 to 6 log reduction in CFU relative to controls). FIG. 29 illustrates the measured zone of inhibition for the various bacteria.

It will be appreciated by those skilled in the art that changes could be made to the exemplary embodiments shown and described above without departing from the broad inventive concept thereof. It is understood, therefore, that this disclosure is not limited to the exemplary embodiments shown and described, but it is intended to cover modifications within the spirit and scope of the present disclosure as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the disclosure, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. Further, it should be appreciated that method steps of all embodiments can be incorporated into the method steps of any other embodiment described herein unless otherwise indicated, and structural features of all embodiments can be incorporated into all other embodiments unless otherwise indicated. The claims directed to the method of the present invention should not be limited to the performance of their steps in the order written, and one skilled in the art can readily appreciate that the steps may be varied and still remain within the spirit and scope of the present invention.

The invention claimed is:

1. A method of forming a biocompatible and implantable multi-layer film for drug delivery comprising:
    placing a first polymer solution comprising a biodegradable polymer into a mold having a plurality of protrusions extending from a bottom of the mold;
    urging the first polymer solution around each of the plurality of protrusions such that a meniscus of polymer solution is formed around the plurality of protrusions;
    placing one or more additional polymer solutions into the mold, the one or more additional polymer solutions comprising a biodegradable polymer, wherein at least one of the first polymer solution or the one or more additional polymer solutions further comprises a drug; and,
    solidifying the first polymer solution and the one or more additional polymer solutions so as to form a biocompatible and biodegradable multi-layer film configured for implantation, wherein the drug is incorporated within film;
    wherein the step of solidifying comprises solidifying the meniscus of polymer solution so as form a plurality of raised lips around the plurality of protrusions;
    wherein a plurality of apertures is formed in the multi-layer film from the protrusions, the plurality of apertures extending completely through the multi-layer film from a first surface to a second surface and wherein each of plurality of the raised lips surrounds a respective aperture of the plurality of apertures.

2. The method of claim 1, wherein the step of placing one or more additional polymer solutions into the mold occurs prior to the step of urging, such that urging the polymer solution includes urging the first polymer solution and the one or more polymer solutions.

3. The method of claim 1, wherein the step of solidifying the polymer solution occurs both prior to and after the step of placing one or more additional polymer solutions into the mold.

4. The method of claim 1, wherein at least one of the first polymer solution or the one or more additional polymer solutions comprises an adhesive layer when solidified.

5. The method of claim 1, wherein at least one of the first polymer solution, or the one or more additional polymer solutions comprises a rate controlling layer for drug release when solidified.

6. The method of claim 1, wherein the drug is dissolved within the multi-layer film.

7. The method of claim 1, wherein the drug is disposed as discrete units within the multi-layer film.

8. The method of claim 7, wherein the drug particles have an average particle diameter under 20 microns.

9. The method of claim 7, wherein the drug particles have an average particle diameter under 10 microns.

10. The method of claim 1, wherein the drug is contained within the first polymer solution.

11. The method of claim 10, wherein the one or more additional polymer solutions form an adhesive layer or a drug controlling layer of the multi-layer film.

12. The method of claim 1, wherein at least one of the first polymer solution or the one or more additional polymer solutions comprises a plurality of drugs.

13. The method of claim 12, wherein the first polymer solution includes a dissolved drug and insoluble drug particles.

14. The method of claim 1, wherein the drug concentration is between about 0.1% to about 13% by weight of the multi-layer film after solidifying.

15. The method of claim 1, wherein
the plurality of apertures provide porosity to the multi-layer film in the range of about 5% to about 25% of the total surface area of the multi-layer film; and,
wherein the drug comprises an antimicrobial agent.

* * * * *